(12) United States Patent
Frommer et al.

(10) Patent No.: US 9,176,143 B2
(45) Date of Patent: Nov. 3, 2015

(54) TRANSMEMBRANE PROTEIN AS BIOSENSORS

(71) Applicant: Carnegie Institution of Washington, Washington, DC (US)

(72) Inventors: Wolf B. Frommer, Washington, DC (US); Roberto De Michele, Washington, DC (US); Cindy Ast, Washington, DC (US)

(73) Assignee: Carnegie Institution of Washington, Washington, DC (US)

( * ) Notice: Subject to any disclaimer, the term of this patent is extended or adjusted under 35 U.S.C. 154(b) by 0 days.

(21) Appl. No.: 14/345,529

(22) PCT Filed: Sep. 18, 2012

(86) PCT No.: PCT/US2012/055875
§ 371 (c)(1),
(2) Date: Mar. 18, 2014

(87) PCT Pub. No.: WO2013/040604
PCT Pub. Date: Mar. 21, 2013

(65) Prior Publication Data
US 2014/0356896 A1    Dec. 4, 2014

Related U.S. Application Data

(60) Provisional application No. 61/536,005, filed on Sep. 18, 2011.

(51) Int. Cl.
*C07K 14/705* (2006.01)
*C07K 14/415* (2006.01)
*G01N 33/68* (2006.01)

(52) U.S. Cl.
CPC .......... *G01N 33/6872* (2013.01); *C07K 14/415* (2013.01); *C07K 14/705* (2013.01); *C07K 2319/21* (2013.01); *C07K 2319/23* (2013.01); *C07K 2319/43* (2013.01); *C07K 2319/60* (2013.01)

(58) Field of Classification Search
CPC ........................... C07K 14/705; C07K 14/415
See application file for complete search history.

(56) References Cited

U.S. PATENT DOCUMENTS

2005/0136488 A1    6/2005    Horecka et al.
2008/0227140 A1    9/2008    Kaper et al.
2011/0223657 A1    9/2011    Kaper et al.

OTHER PUBLICATIONS

Yoshihara et al., 2008, An Rh1-GFP Fusion Protein Is in the Cytoplasmic membrane of a White Mutant Strain of *Chlamydomonas reinhardtii*, Molecular Plant, 1(6): 1007-1020.*
International Patent Application No. PCT/US2012/055875; International Search Report mailed Nov. 20, 2012.
Forrest et al. (2009) The Rocking Bundle: A Mechanism for Ion-Coupled Solute Flux by Symmetrical Transporters, Physiology, 24:377-386.
Kaper et al. (2007) Nanosensor Detection of an Immunoregulatory Tryptophan Influx/Kynurenine Efflux Cycle, PLoS Biol., 5:2201-2210.
Khademi et al. (2004) Mechanism of Ammonia Transport by Amt/MEP/Rh: Structure of AmtB at 1.35 Angstrom, Science, 305:1587-1594.
Thomas et al. (2000) Membrane Topology of the Mep/Amt Family of Ammonium Transporters, Mol. Microbiol., 37:331-344.
Watanabe et al. (2010) The Mechanism of Sodium and Substrate Release from the Binding Pocket of vSGLT, Nature, 468:988-991.

* cited by examiner

*Primary Examiner* — Amber D Steele
(74) *Attorney, Agent, or Firm* — Morgan, Lewis & Bockius LLP

(57) ABSTRACT

The disclosure relates to engineered transport proteins comprising at last one fluorescent reporter covalently bound to the transporter protein, wherein the transporter proteins comprise a structural inverted repeat motif, with the motif comprising a first and second subunit that are structural inverted repeats of one another and that are joined to one another by a polypeptide loop.

14 Claims, 29 Drawing Sheets

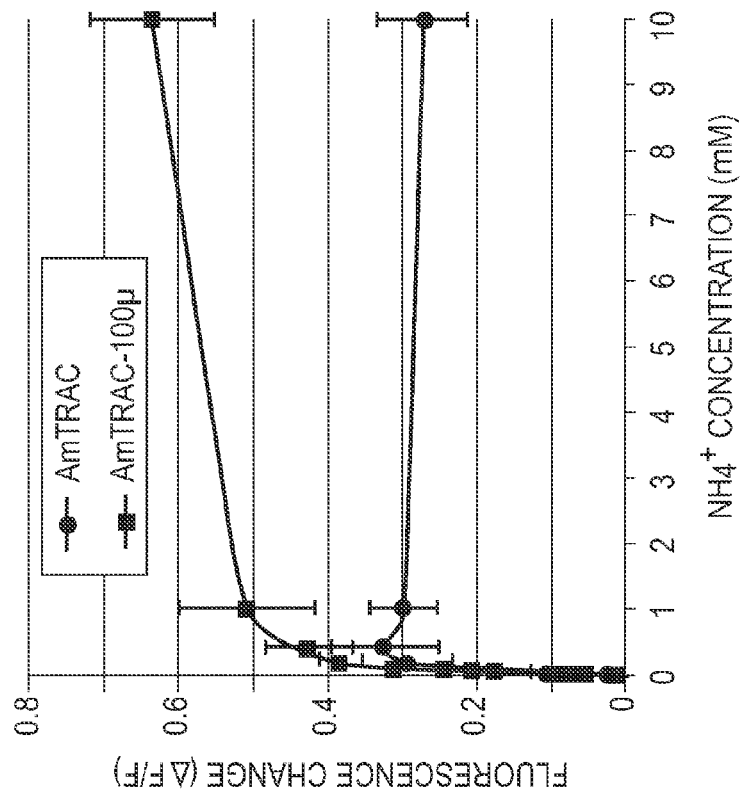
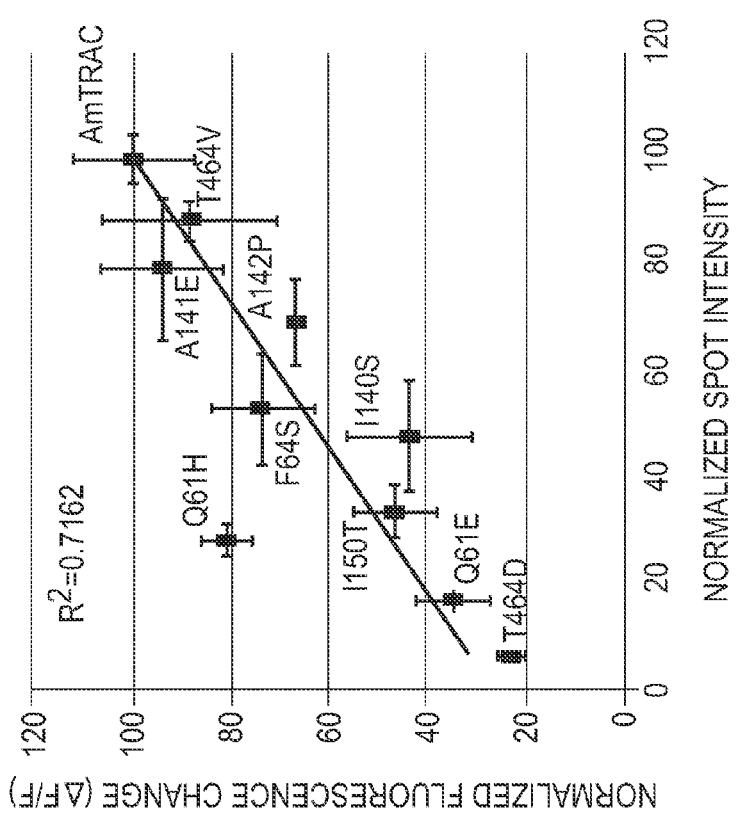
FIG. 2E
FIG. 2F

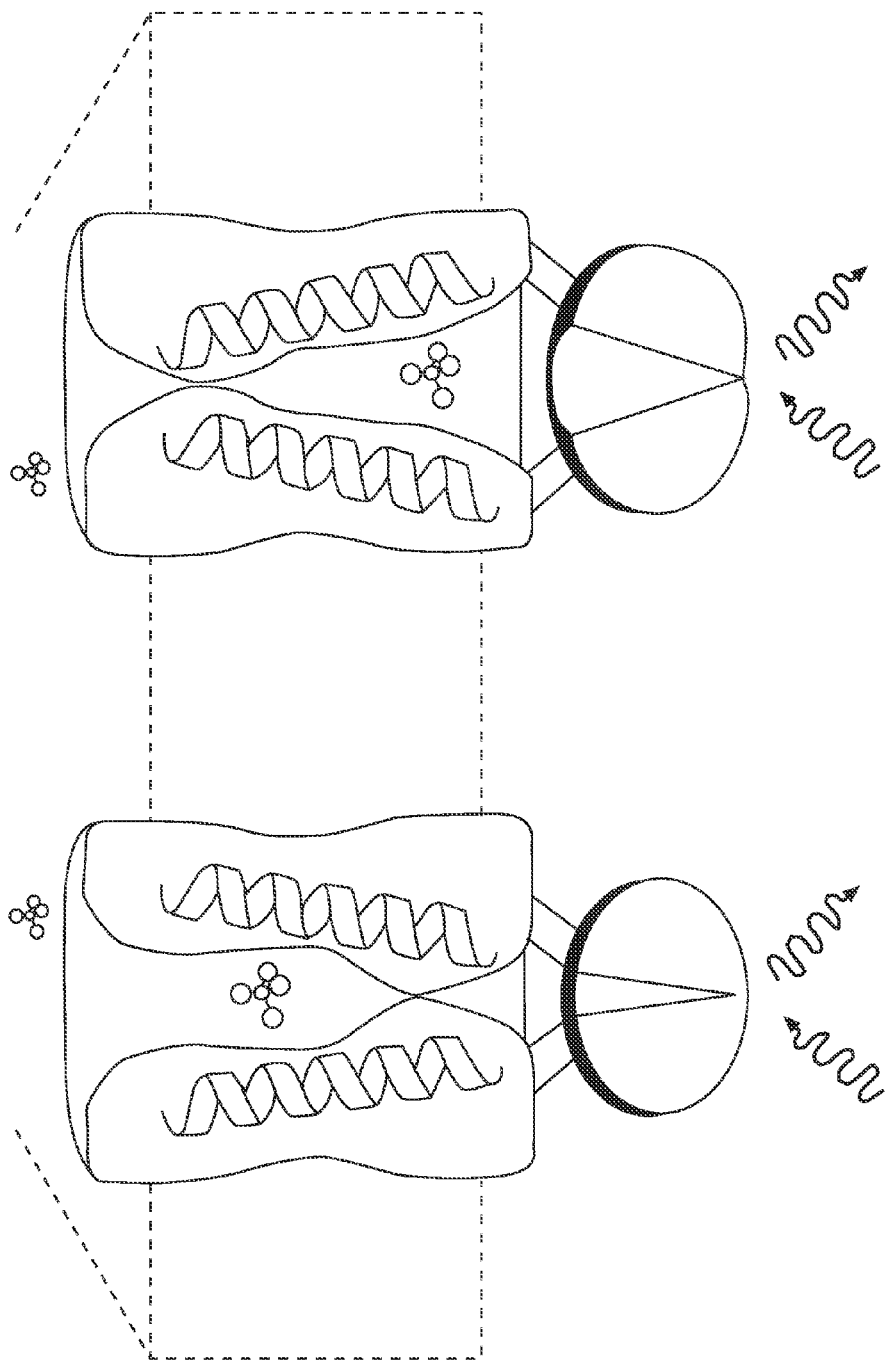

```
    M  S  G  A  I  T  C  S  A  A  D  L  A  T  L  L  G  P  N  A
1   atgtcaggagcaataacatgctctgcggccgatctcgccacccctacttggccccaacgcc   20
    T  A  A  A  D  Y  I  C  G  Q  L  G  T  V  N  N  K  F  T  D
21  acggcggcggccgactacatttgcggccaattaggcaccgttaacaacaagttcaccgat   40
    A  A  F  A  I  D  N  T  Y  L  L  F  S  A  Y  L  V  F  A  M
41  gcagccttcgccatagacaacacctacctcctcttctctgcctaccttgtcttcgccatg   60
    Q  L  G  F  A  M  L  C  A  G  S  V  R  A  K  N  T  M  N  I
61  cagctcggcttcgctatgctttgtgctggttctgttagagccaagaatacgatgaacatc   80
    M  L  T  N  V  L  D  A  A  A  G  G  L  F  Y  Y  L  F  G  Y
81  atgcttaccaatgtccttgacgctgcagccggaggactcttctactatctctttggttac   100
    A  F  A  F  G  G  S  S  E  G  F  I  G  R  H  N  F  A  L  R
101 gcctttgcctttggaggatcctccgaagggttcattggaagacacaactttgctcttaga   120
    D  F  P  T  P  T  A  D  Y  S  F  F  L  Y  Q  W  A  F  A  I
121 gactttccgactcccacagctgattactctttcttcctctaccaatgggcgttcgcaatc   140
    A  A  A  G  I  T  S  G  S  I  A  E  R  T  Q  F  V  A  Y  L
141 gcggccgctggaatcacaagtggttcgatcgcagagaggactcagttcgtggcttacttg   160
    I  Y  S  S  F  L  T  G  F  V  Y  P  V  V  S  H  W  F  W  S
161 atatactcttctttcttaaccggatttgtttacccggttgtctctcactggttttggtcc   180
    P  D  G  W  A  S  P  F  R  S  A  D  D  R  L  F  S  T  G  A
181 ccggatggatgggccagtcccttccgttcagcggatgatcgtttgtttagcaccggagcc   200
    I  D  F  A  G  S  G  V  V  H  M  V  G  G  I  A  G  L  W  G
201 attgactttgctggctccggtgttgttcacatggttggtggcatagcaggtttatggggt   220
    A  L  I  E  G  P  R  R  G  R  F  E  K  L  E  N  V  Y  I  K
221 gctcttattgaaggtcctcgtcgtggtcggttcgagaaactcgagaacgtctatatcaag
    A  D  K  Q  K  N  G  I  K  A  N  F  K  I  R  H  N  I  E  D
    gccgacaagcagaagaacggcatcaaggcgaacttcaagatccgccacaacatcgaggac
    G  G  V  Q  L  A  Y  H  Y  Q  Q  N  T  P  I  G  D  G  P  V
    ggcggcgtgcagctcgcctaccactaccagcagaacacccccatcggcgacggccccgtg
    L  L  P  D  N  H  Y  L  S  V  Q  S  K  L  S  K  D  P  N  E
    ctgctgcccgacaaccactacctgagcgtccagtccaagctgagcaaagaccccaacgag
    K  R  D  H  M  V  L  L  E  F  V  T  A  A  G  I  T  L  G  M
    aagcgcgatcacatggtcctgctggagttcgtgaccgccgccgggatcatcctcggcatg
    D  E  L  Y  K  G  G  T  G  G  S  M  V  S  K  G  E  E  L  F
    gacgagctgtacaagggtggtaccggtggatctatggtgagcaagggcgaggagctgttc
    T  G  V  V  P  I  L  V  E  L  D  G  D  V  N  G  H  K  F  S
    accggggtggtgcccatcctggtcgagctggacggcgacgtaaacggccacaagttcagc
    V  S  G  E  G  E  G  D  A  T  Y  G  K  L  T  L  K  F  I  C
    gtgtccggcgagggcgagggcgatgccacctacggcaagctgaccctgaagttcatctgc
    T  T  G  K  L  P  V  P  W  P  T  L  V  T  T  L  T  Y  G  V
    accaccggcaagctgcccgtgccctggcccaccctcgtgaccaccctgacctacggcgtg
```

*FIG. 8*

```
      Q  C  F  S  R  Y  P  D  H  M  K  Q  H  D  F  F  K  S  A  M
    cagtgcttcagccgctaccccgaccacatgaagcagcacgacttcttcaagtccgccatg
      P  E  G  Y  I  Q  E  R  T  I  F  F  K  D  D  G  N  Y  K  T
    cccgaaggctacatccaggagcgcaccatcttcttcaaggacgacggcaactacaagacc
      R  A  E  V  K  F  E  G  D  T  L  V  N  R  I  E  L  K  G  I
    cgcgccgaggtgaagttcgagggcgacaccctggtgaaccgcatcgagctgaagggcatc
      D  F  K  E  D  G  N  I  L  G  H  K  L  E  Y  N  F  N  G  G
    gacttcaaggaggacggcaacatcctggggcacaagctggagtacaacttt aat gtggt   235
         R  A  I  A  L  R  G  H  S  A  S  L  V  V  L  G  T  F  L  L
236  cgcgctattgctctgcgcggccactctgcctcgctagtagtcttaggaaccttcctccta   255
         W  F  G  W  Y  G  F  N  P  G  S  F  T  K  I  L  V  P  Y  N
256  tggtttggatggtatggtttcaaccccgttccttcactaagatactcgttccgtataat   275
         S  G  S  N  Y  G  Q  W  S  G  I  G  R  T  A  V  N  T  T  L
276  tctggttccaactacggccaatggagcggaatcggccgtacagcggttaacaccacactc   295
         S  G  C  T  A  A  L  T  T  L  F  G  K  R  L  L  S  G  H  W
296  tcaggatgcacagcagctctaaccacactctttggtaaacgtctcctatcaggccactgg   315
         N  V  T  D  V  C  N  G  L  L  G  G  F  A  A  I  T  A  G  C
316  aacgtaacggacgtttgcaacgggttactcggtgggtttgcggccataaccgcaggttgc   335
         S  V  V  E  P  W  A  A  I  V  C  G  F  M  A  S  V  V  L  I
336  tccgtcgtagagccatgggcagcgattgtgtgcggcttcatggcttctgtcgtccttatc   355
         G  C  N  K  L  A  E  L  V  Q  Y  D  D  P  L  E  A  A  Q  L
356  ggatgcaacaagctcgcggagcttgtacaatatgatgatccactcgaggcagcccaacta   375
         H  G  G  C  G  A  W  G  L  I  F  V  G  L  F  A  K  E  K  Y
376  catggagggtgtggcgcgtggggggttgatattcgtaggattgtttgccaaagagaagtat   395
         L  N  E  V  Y  G  A  T  P  G  R  P  Y  G  L  F  M  G  G  G
396  ctaaacgaggtttatggcgccaccccgggaaggccatatggactatttatgggcggagga   415
         G  K  L  L  G  A  Q  L  V  Q  I  L  V  I  V  G  W  V  S  A
416  gggaagctgttgggagcacaattggttcaaatacttgtgattgtaggatgggttagtgcc   435
         T  M  G  T  L  F  F  I  L  K  R  L  N  L  L  R  I  S  E  Q
436  acaatgggaacactcttcttcatcctcaaaagctcaatctgcttaggatctcggagcag   455
         H  E  M  Q  G  M  D  M  T  R  H  G  G  F  A  Y  I  Y  H  D
456  catgaaatgcaagggatggatatgacacgtcacggtggctttgcttatatctaccatgat   475
         N  D  D  E  S  H  R  V  D  P  G  S  P  F  P  R  S  A  T  P
476  aatgatgatgagtctcatagagtggatcctggatctcctttccctcgatcagctactcct   495
         P  R  V
496  cctcgcgtt
```

FIG. 8
(cont.)

G A L I E G P R R G R F E K G G R A I A L R G H S A S L V
220 221 222 223 224 225 226 227 228 229 230 231 232 233 234 235 236 237 238 239 240 241 242 243 244 245 246 247 248
*FIG. 9A*
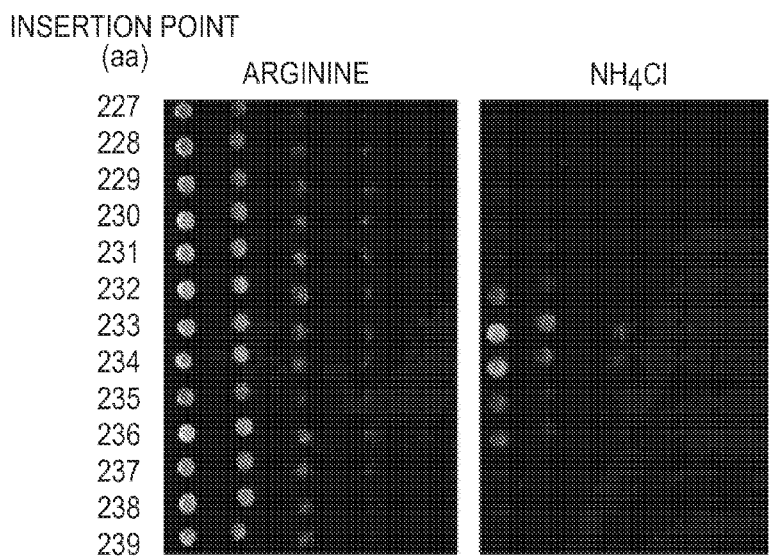
*FIG. 9B*
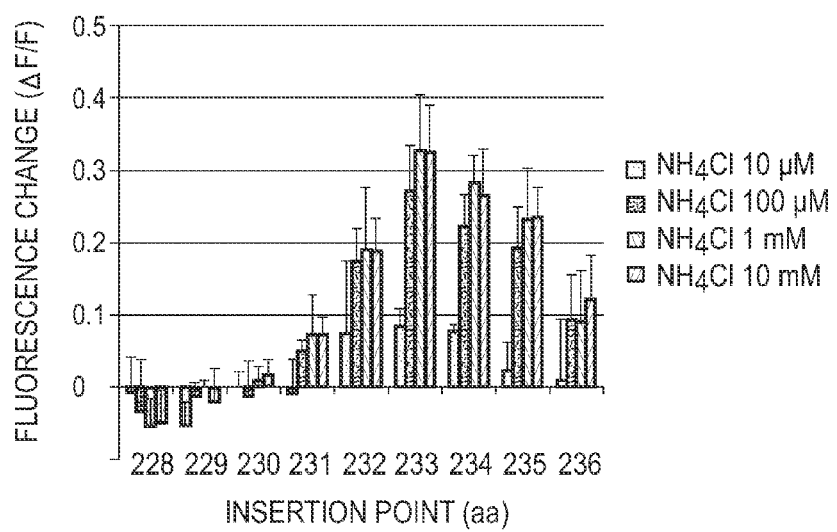
*FIG. 9C*

| INSERTION POINT (aa) | aa DELETED | RESPONSE |
|---|---|---|
| 230-232 | 2 | NO |
| 231-232 | 1 | NO |
| 232-234 | 2 | NO |
| 230-233 | 3 | NO |
| 231-233 | 2 | NO |
| 232-233 | 1 | NO |
| 233 | 0 | YES |
| 230-234 | 4 | NO |
| 231-234 | 3 | NO |
| 232 | 0 | YES |
| 233-234 | 1 | YES |
| 234 | 0 | YES |
| 230-235 | 5 | NO |
| 231-235 | 4 | NO |
| 232-235 | 3 | NO |
| 233-235 | 2 | YES |
| 234-235 | 1 | YES |
| 230-236 | 6 | NO |
| 231-236 | 5 | NO |
| 232-236 | 4 | NO |
| 233-236 | 3 | YES |
| 234-236 | 2 | NO |
| 230-237 | 7 | NO |
| 231-237 | 6 | NO |
| 232-237 | 5 | NO |
| 233-237 | 4 | NO |
| 234-237 | 3 | NO |

At-Amt1;3  MSGAITCSAADLATLLGPNATAAADYICGQLGTVNNKFTDAAFAIDNTYLLFSAYLVFAMQLGFAMLCAGSVRAKNTMNIMLTN 84
Af-Amt1    --------------------------------MSDGNVAWLLASTALVMLMVPGVGFEYAGMVRRKNAVNMIALS 43

At-Amt1;3  VLDAAAGLFYLFGYAFAFGGSSEGFIGRHNFALRDFPTPADYSFFLYQWAFAIAAAGITSGSIAERTQFVAYLIYSSFLTG 168
Af-Amt1    FISLITPVLLMIFYGYSVSFGNDISGIIGGLNYALLSG-VKGEDLLFMYQMMFAAVTIALLSAIAERAKVSSFILLSAIWLT 126

At-Amt1;3  FVYPVVSHMFWSPDGWASPERSADDRLFSTGAIDFAGSGVVHMVGGIAGLWGALIEGPRRGRFEKGGRAIALRGHSASLVLGT 252
Af-Amt1    ---------GGWLAKLGALDFAGGMVHISSGFAALAVAMTIGKRAG-----FEEYSIEPHSIPLTLFGA 194

At-Amt1;3  FLLWFGWYGFNPGSFTKILVPYNSGSNYGQWSGIGRTAVNTTLSGCTAALTTLFGKRLLSGHWNVTDVCNGLLGGFAAITAGCS 336
Af-Amt1    ALLLWFGFN-----------------GGSALAANDVAINAVVWINESAAVAGFWMWVIGWIKGPGSLGIVSGAIAGLAAITPAAG 265

At-Amt1;3  VVEPWAATVCGFMASVVLIGCNKLAELVQVDDPLEAAQLHGGCAWGLIFVGLFAKEKYLNEVYGATPGRPYGLFMGGGKLLG 420
Af-Amt1    FVDVKGAIVIGIWAGIVCYIAMDFRIKKKIDESILDAWAIRGIGGIWGSVAVGIWANPEVN----------GYAGLLFGNPQLLIV 339

At-Amt1;3  AQIVQILVIVGWVSATMGTLFFLIKRLNLLRISEQHEMQGMDMTRHGGFAYIYHDNDDESHRVDPGSPFPRSATPPRV 498
Af-Amt1    SQLIAVASTTAYAFLVTLILAKAVDAAVGLRVSSQEEYVGLDLSQHEEVAYT-------------------------- 391

*FIG. 13A*

TRANSMEMBRANE PROTEIN AS BIOSENSORS

CROSS-REFERENCE TO RELATED APPLICATIONS

The application claims priority to U.S. Provisional Application No. 61/536,005, filed 18 Sep. 2011.

STATEMENT REGARDING FEDERALLY SPONSORED RESEARCH OR DEVELOPMENT

Part of the work performed during development of this invention utilized U.S. Government funds from National Science Foundation Grant No. 1021677. The U.S. Government has certain rights in this invention.

SEQUENCE LISTING INFORMATION

A computer readable text file, entitled "056100-5085-WO-SequenceListing.txt," created on or about 12 Sep. 2012 with a file size of about 18 kb contains the sequence listing for this application and is hereby incorporated by reference in its entirety.

BACKGROUND OF THE INVENTION

1. Field of the Invention

The invention relates to engineered transporter proteins comprising at least one fluorescent reporter covalently bound to the transporter protein, wherein the transporter proteins of the present invention comprise a structural inverted repeat motif, with the motif comprising a first and second subunit that are structural inverted repeats of one another and that are joined to one another by a polypeptide loop.

2. Background of the Invention

Transporter proteins are membrane bound proteins that often utilize potential gradients to drive transport of molecules and ions into and out of cells. Traditionally, these proteins are classified based on the similarity of their amino acid sequence, i.e., the primary structure of the protein.

There is, however, an understanding of the three-dimensional structure of some of these transporters that is emerging. Indeed, some of these transporter proteins possess a structural inverted repeat, and transporters proteins with apparently disparate amino acid sequences have been shown to assume such a structure. It was not at all understood how this structural inverted repeat may affect the molecule or ion flux that is associated with these proteins.

Voltage sensors have been generated by others based on, for example, potassium channels, but these voltage sensors do not directly measure potassium transport. Instead these voltage sensors merely measure membrane potential using the voltage sensor of the transporter. To date, there has been no way to monitor or directly measure molecule or ion transport.

The present invention solves the problems by providing transport proteins that are capable of signaling a conformational change during the transport process. The invention thus provides sensors that are based on virtually any transporter with the required three-dimensional conformation, which, in turn, provides a new means of monitoring their activity or modifications by the regulatory machinery in real time in vivo.

SUMMARY OF THE INVENTION

The invention relates to engineered transporter proteins comprising at least one fluorescent reporter covalently bound to the transporter protein. The transporter proteins of the present invention comprise a structural inverted repeat motif, with the motif comprising a first and second subunit that are structural inverted repeats of one another and that are joined to one another by a polypeptide loop. The fluorescent reporter typically is covalently bound to the polypeptide loop that joins the two subunits of the structural inverted repeat.

The invention also relates to methods of using these engineered transporter proteins to monitor analyte movement across a membrane, such as a cell membrane.

The invention also relates to nucleic acids encoding the engineered transporter proteins.

BRIEF DESCRIPTION OF THE DRAWINGS

FIG. 3 depicts a model for AmTrac sensor and AMT transport. AMT switches between at least two distinct states during transport of ammonium: an outward, open state (a) and an inward, open state (b). The movement of TMH-V (left helix) and TMH-VI (right helix) is transmitted to the connecting loop, affecting the inserted mcpGFP and resulting in a change in fluorescence emission.

FIG. 8 depicts the sequence of AmTrac. Protein sequence of AmTrac. Underlined residues constitute synthetic linker segments. Bolded residues correspond to the mcpGFP moiety. Numbers indicate amino acid position in AtAMT1;3.

FIG. 9 depicts the Influence of the insertion position of mcpGFP in L5-6 of AtAMT1;3. To probe the tolerance of L5-6 of AMT1;3 to insertion, the insertion position was varied within the peptide loop. (a) Schematic representation of the L5-6 region of AtAMT1;3. Underlined residues correspond to TMH 5 (left) and TMH 6 (right). (b) Growth assay of the yeast Δmep1,2,3 mutant transformed with insertion mutants on solid media containing 2 mM $NH_4Cl$ or 1 mM arginine (growth control) as the sole nitrogen source for three days. Numbers indicate the insertion site within AtAMT1;3 (residue preceding the point of insertion of mcpGFP). The center of L5-6 (position 233) tolerated the insertion with minimal effects on growth. (c) Fluorescence response of the variants to addition of the indicated concentrations of $NH_4Cl$. Data were normalized to the water-treated control (0) (mean±s.d.; n=2). Variants with mcpGFP inserted into the central positions showed the strongest ammonium-induced response.

DETAILED DESCRIPTION OF THE INVENTION

Figures 1A, 1B:
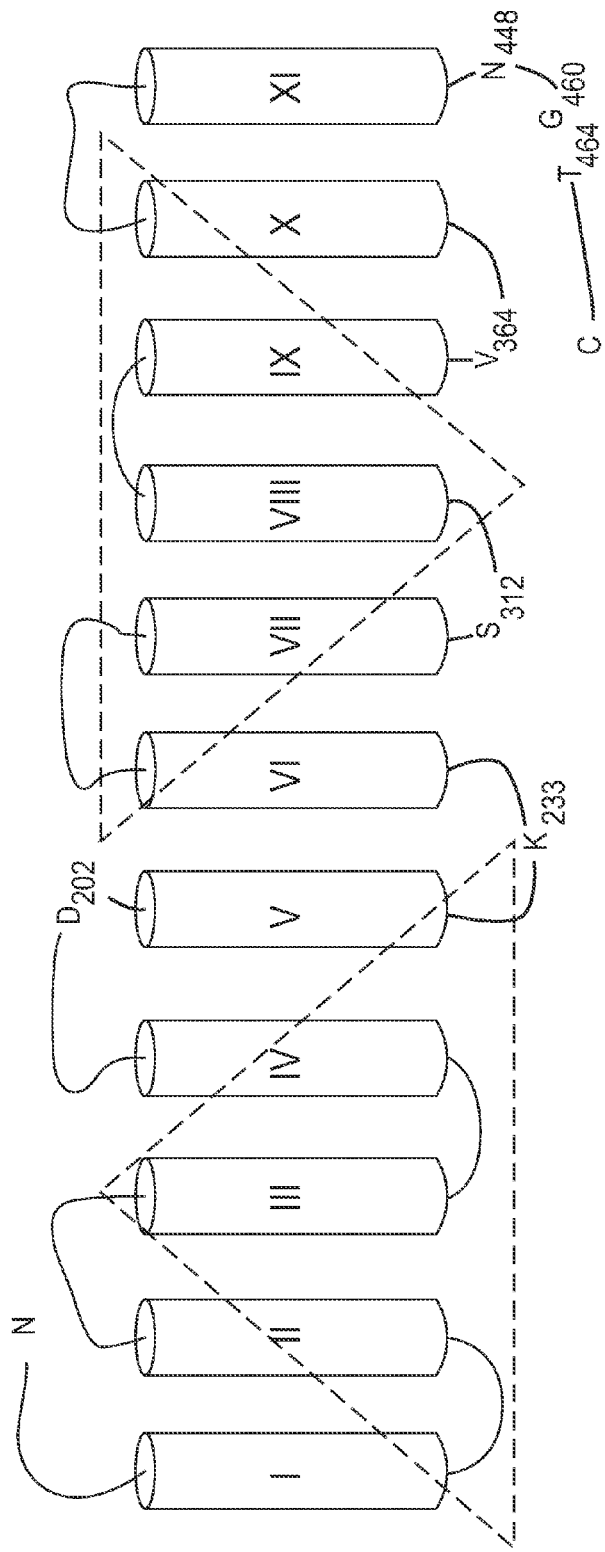
FIG. 1 depicts the design and characterization of one specific ammonium transporter named "AmTrac." (a) Topological representation of AMT1;3 by HMMTOP. 11 Transmembrane helices (TMH) are organized in a pseudo-symmetric structure, i.e., structural inverted repeats, (TMH I-V and TMH VI-X) with an extra terminal TMH-XI that directs the C-terminus to the cytosol. The position of the residues preceding the insertion points of FPs in L5-6, 7-8, 9-10 and in the C-tail are indicated. Residues D202, G460 and T464 are important for the activity of the transporter and are also shown. (b) Schematic representation of AmTrac transporter. Linkers between AMT1;3 and mcpGFP are indicated. (c) Three-dimensional model of AmTrac based on the crystal structures of Af-AMT1 (2B2H) and cpGFP (3evp). One monomer is shown in cartoon and the rest of the trimer complex is represented as a shaded surface in the background. mcpGFP (bottom) was inserted in position 233 of L5-6 of AMT1;3, connecting TMH-V and -VI. (d) Substrate specificity of the fluorescent response of AmTrac. Yeast cells expressing the sensor were treated with the indicated salts at 1 mM concentration. Data are normalized to water-treated control (0) (mean±SD; n=3). Only the ammonium treatments were significantly different from control (SNK test: *$P<0.01$). (e) Titration of the fluorescent response of AmTrac (circles and left y-axis) and of ammonium uptake of AMT1;3 (squares right y-axis). Data are normalized to water-treated controls (0) (mean±s.d.; n=3). (f) Response of a single yeast cell expressing AmTrac to square pulses of $NH_4Cl$.
Figure 1C:
Figure 1D:
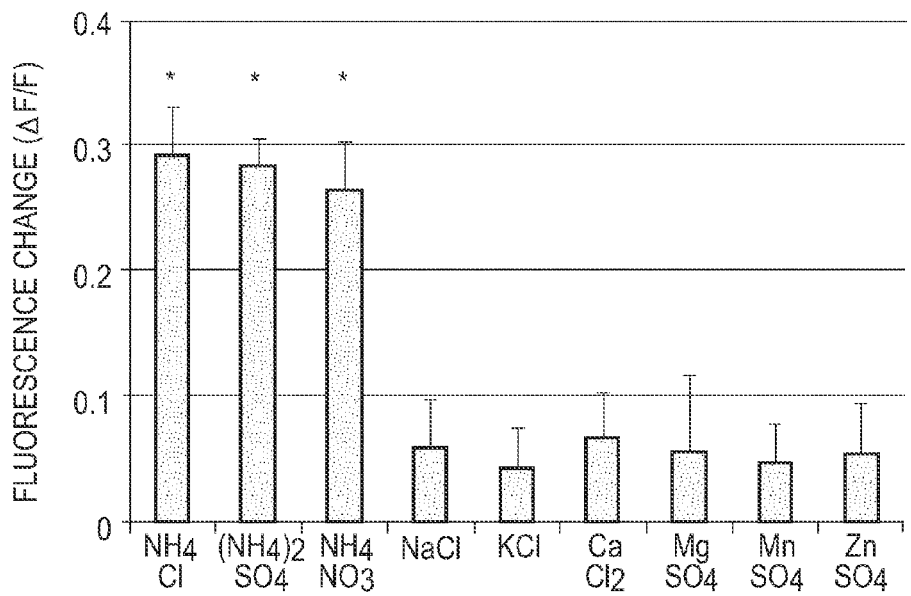
Figure 1E:
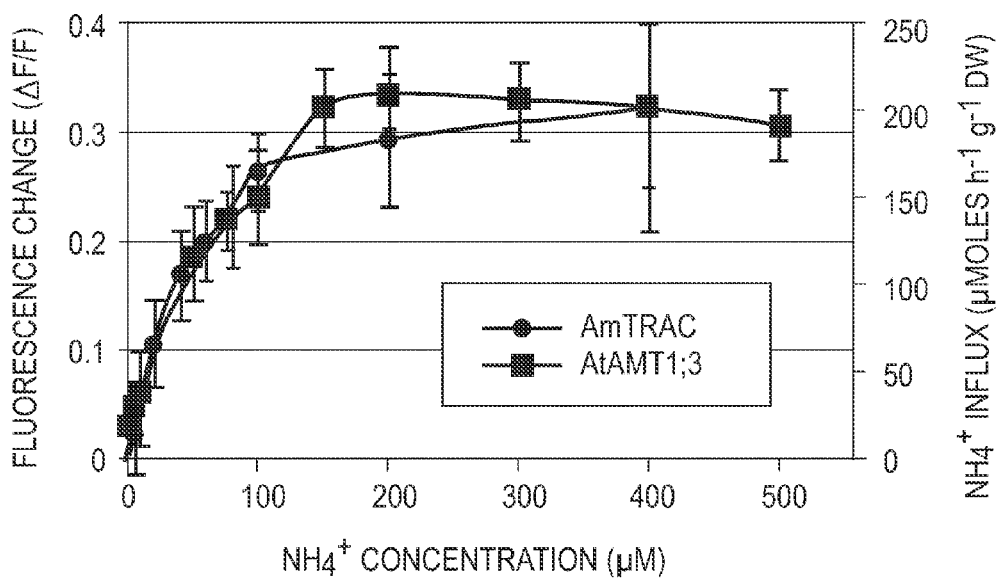
Figure 1F:
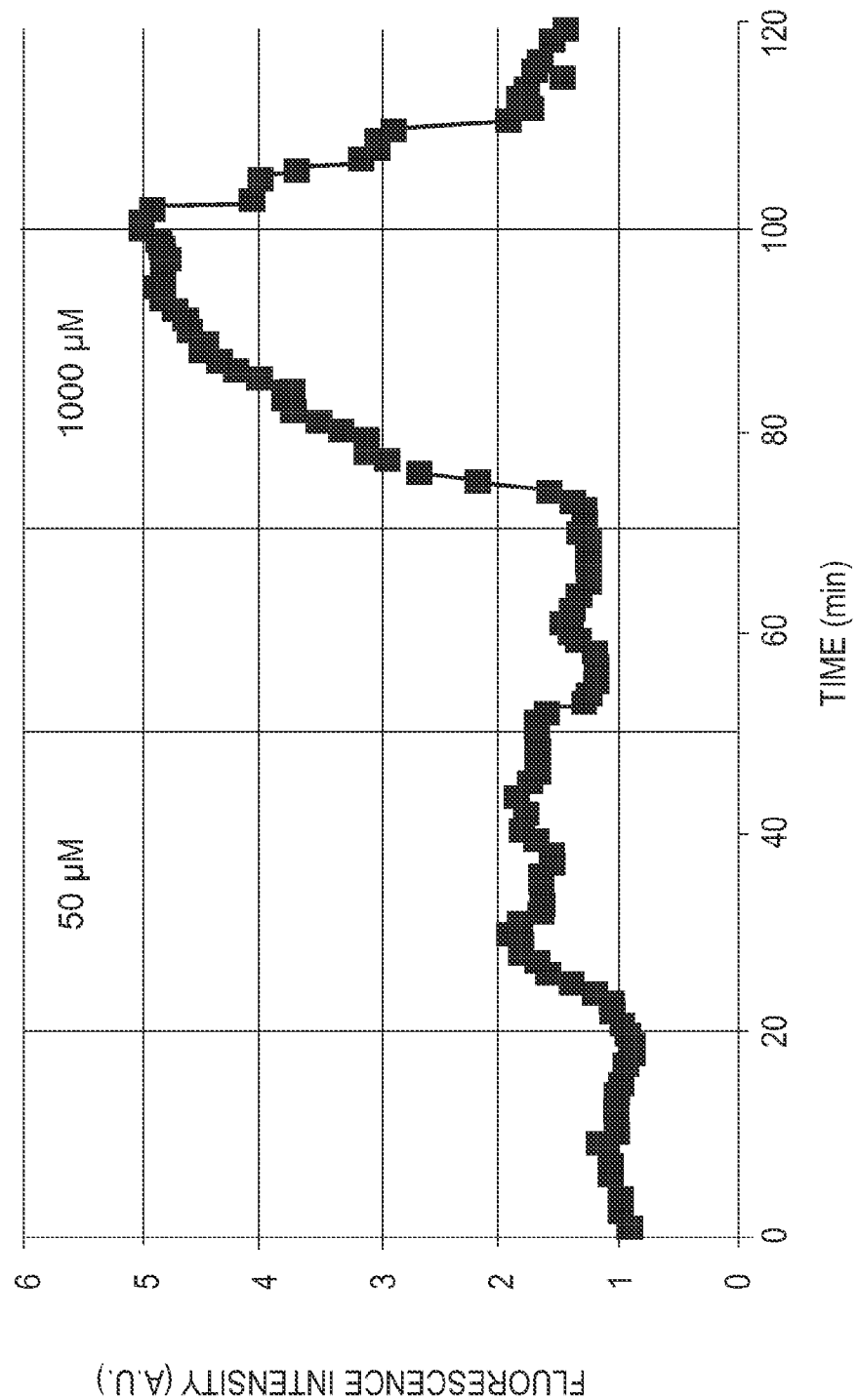

The invention relates to engineered transporter proteins comprising at least one fluorescent reporter covalently bound to the transporter protein. The transporter proteins of the present invention must comprise at least one "structural inverted repeat motif." As used herein, a structural inverted repeat motif refers to a specific arrangement of secondary and tertiary structures of a protein. In particular a transporter protein with a "structural inverted repeat" is a protein that has multiple alpha helices as part of its secondary structure, and many, but not necessarily all, of these alpha helices are arranged in such a manner that they span a plasma membrane ("transmembrane helices") when the protein occurs in its natural environment. Furthermore, a "structural inverted repeat" indicates that there is an "approximate axis of symmetry" dividing the transmembrane helices into two set of helices. Each set of transmembrane helices on either half of the approximate axis of symmetry is considered a "subunit" for the purposes of the present invention. In transporter proteins containing an inverted structural repeat, the alpha-carbon atoms of the residues making up the first set ("first subunit") of transmembrane helices can be superimposed on the alpha-carbon atoms of the residues making up the second set ("second subunit") of transmembrane helices by a rotation of about 180 degrees. The ability to superimpose the alpha-carbon atoms of the transmembrane helices between the two subunits provides the "structural repeat" aspect of the transporter protein. The approximate 180 degree rotation of one subunit relative to the other subunit such that the alpha-carbon atoms between the two subunits can be superimposed on one another provides "inverted" aspect of the inverted structural repeat.

The first and second subunits that make up the structural inverted repeat need not be rotated exactly 180 degrees relative to one another. For example, in the Na$^+$/Cl$^-$ transporter protein in *Aquifex aeolicus*, the second subunit is rotated about 176.5 degrees relative to the first subunit. See Yamashita, A., et al. *Nature*, 437:215-223 (2005), which is incorporated by reference. In another example, the Mhp1 transporter (indolyl-methyl- and benzyl-hydantions), which is a member of the nucleobase-cation-symport (NCS1) family of proteins, from *M. liquifaciens* is a transporter protein with a structural inverted repeat in which the second subunit is rotated about 168 degree relative to the first subunit. See Weyand, S. et al., *Science*, 322:709-713 (2008), which is incorporated by reference. For the purposes of the present invention, the rotation needed to superimpose the two halves of the repeat structure such that the protein is said to have a "structural inverted repeat" can be any angle from about 90 degrees to about 270 degrees. In one specific embodiment, the rotation needed to superimpose the two halves of the repeat structure such that the protein is said to have a "structural inverted repeat" can be any angle from about 100 degrees to about 260 degrees. In another specific embodiment, the rotation needed to superimpose the two halves of the repeat structure such that the protein is said to have a "structural inverted repeat" can be any angle from about 110 degrees to about 250 degrees. In another specific embodiment, the rotation needed to superimpose the two halves of the repeat structure such that the protein is said to have a "structural inverted repeat" can be any angle from about 120 degrees to about 240 degrees. In another specific embodiment, the rotation needed to superimpose the two halves of the repeat structure such that the protein is said to have a "structural inverted repeat" can be any angle from about 130 degrees to about 230 degrees. In another specific embodiment, the rotation needed to superimpose the two halves of the repeat structure such that the protein is said to have a "structural inverted repeat" can be any angle from about 140 degrees to about 220 degrees. In another specific embodiment, the rotation needed to superimpose the two halves of the repeat structure such that the protein is said to have a "structural inverted repeat" can be any angle from about 150 degrees to about 210 degrees. In another specific embodiment, the rotation needed to superimpose the two halves of the repeat structure such that the protein is said to have a "structural inverted repeat" can be any angle from about 160 degrees to about 200 degrees. In another specific embodiment, the rotation needed to superimpose the two halves of the repeat structure such that the protein is said to have a "structural inverted repeat" can be any angle from about 170 degrees to about 190 degrees.

Proteins said to have a structural inverted repeat can have any number transmembrane helices in each subunit, and the number of transmembrane helices need not be the same in the two subunits. In general, the first and second subunits can each independently have 2, 3, 4, 5, 6, 7, 8, 9 or even 10 transmembrane helices. Thus, as an example, one subunit may have 5 transmembrane helices in its first subunit and 5 transmembrane helices in its second subunit. As another example, one subunit may have 5 transmembrane helices in its first subunit and 6 transmembrane helices in its second subunit. In general, however, the number of transmembrane helices that are rotated in the second subunit, relative to the first subunit, will define the number of transmembrane helices in the subunits. For example, the Na$^+$/Cl$^-$ transporter protein in *Aquifex aeolicus* has 5 transmembrane helices in the first subunit and 5 transmembrane helices in the second subunit.

In addition, the transporter porter protein may have additional secondary structures that are not part of the structural inverted repeat motif. For example, the transporter proteins may have additional alpha helical structures, and these alpha helices may even be transmembrane helices. But these additional transmembrane helices would not necessarily be part of the structural inverted repeat motif. For example, the Na$^+$/Cl$^-$ transporter protein in *Aquifex aeolicus* has 12 total transmembrane alpha helices, numbered 1-12. The alpha helices numbered 1-5 in the Na$^+$/Cl$^-$ transporter protein in *Aquifex aeolicus* are considered to make up the first subunit of the structural inverted repeat motif, and helices 6-10 make up the second subunit of the structural inverted repeat motif. Alpha helices 11 and 12 in the Na$^+$/Cl$^-$ transporter protein in *Aquifex aeolicus* span the membrane but do not belong to either the first or second subunit of the structural inverted repeat motif.

Moreover, the transmembrane helices in the subunits need not be continuous such that there may be a break helical structure along the transmembrane helix. For example, the transmembrane helices numbered 1 and 6 of the Na$^+$/Cl$^-$ transporter protein in *Aquifex aeolicus* are both discontinuous transmembrane helices, yet each helix would be considered a single transmembrane helix that is part of their respective subunit.

The transmembrane helices are connected to one another by a chain of amino acids. Often, two helices are connected to one another with a chain of amino acids that do not possess a secondary structure. On the other hand, the chain of amino acids connecting two transmembrane helices may have a secondary structure, e.g., an alpha helix, occurring along its length. For example, one subunit of the structural inverted repeat may have a transmembrane helix connected to a second transmembrane helix through a chain of amino acids ("polypeptide loop"). The transmembrane helices connected by the polypeptide loop may or may not be physically located beside each other in the protein structure. The helices are said to be "connected to one another" based upon the overall amino acid sequence of the protein. For example, amino acid residues 41-70 of the linear amino acid sequence may form one transmembrane helix and amino acid residues 88-124 may form another transmembrane helix. The two helices would be connected to one another through the polypeptide chain on amino acid residues 71-87, although the two transmembrane helices are necessarily physically beside one another in the overall three-dimensional structure of the protein. Continuing the example, amino acid residues 71-87 of the polypeptide loop connecting the two transmembrane helices may themselves form an alpha helical structure, but this alpha-helical structure would not be considered one of the transmembrane helices of that form the structural inverted repeat structure if the alpha helix of the polypeptide loop did not span the membrane when normally expressed.

Moreover, the polypeptide loop connecting the two helices may be external to the plasma membrane ("extracellular") or in may be internal to the plasma membrane ("intracellular"). Of course, any reference herein to any portion of the transporter protein relative to a cell or plasma membrane is for illustrative purposes only. The proteins may be synthesized and formed ex vivo and subsequently folded into a three dimensional structure that resembles or is the same as the properly folded protein if it were to be expressed natively in a cell.

Based on the three dimensional arrangement of the transporter protein and the linearity of the amino acid sequence, there will be a polypeptide loop that connects two transmembrane helices, where the two transmembrane helices are in different subunits of the structural inverted repeat. This polypeptide loop is considered to be the polypeptide loop that connects the two subunits of the structural inverted repeat motif of the transporter peptide. For example, FIG. 1a shows a cartoon diagram of an ammonium transporter protein comprising a structural inverted repeat motif. Each subunit of the structural inverted repeat in the ammonium transporter comprises 5 transmembrane helices, with helices 1-5 belonging to the first subunit and helices 6-10 belonging to the second subunit. Each helix is connected to the "next" helix in the amino acid chain through a polypeptide loop as defined herein. Transmembrane helix 5 is joined to transmembrane helix 6 through a polypeptide loop, and helix 5 and helix 6 belong to two different subunits of the structural inverted repeat motif. The polypeptide loop that connects the first and second subunits of the structural inverted repeat is the loop that joins transmembrane helices 5 and 6 to one another. The polypeptide loop that connects the first and second subunits of the structural inverted repeat can be extracellular or it can be intracellular.

Examples of transporter proteins include but are not limited to members of the APC (amino acid, polyamine and organocation) superfamily of transporter proteins that have a structural inverted repeat, the AMT/MEP/RH superfamily of transporters, the Neurotransmitter:Sodium Symporter (NSS) superfamily of transporters, such as but not limited to the LeuT, Tyt1 and TnaT transporters, the Betaine/Carnitine/Choline superfamily of transporters (BCCT), such as but not limited to BetP, the The Amino Acid/Auxin Permease (AAAP) superfamily of transports, the Solute:Sodium Symporter (SSS) superfamily of transporters, the Alanine or Glycine:Cation Symporter (AGCS) superfamily of transporters, the Cation-Chloride Cotransporter (CCC) superfamily of transporters, the Nucleobase:Cation Symporter-1 (NCS1) superfamily of transporters and the Hydroxy/Aromatic Amino Acid Permease (HAAAP) superfamily of transporters.

Determining if a transporter protein contains a structural inverted repeat can be performed by resolving the crystal structure of the proteins through for example, X-ray crystallography and NMR-spectroscopy. The topology of protein transporters can efficiently and reliably be predicted using programs such as TMHMM (available on the internet at www.cbs.dtu.dk/services/TMHMM/) the current version of which is "Server 2.0." Determining if a transporter protein contains repeated elements can be performed by alignment of the protein sequence to itself, or by algorithms such as Motif-Scan, Radar (de novo repeat detection in protein sequences), REP (searches a protein sequence for repeats), REPRO (de novo repeat detection in protein sequences, T-REKS (de novo detection and alignment of repeats in protein sequences), TRUST (de novo repeat detection in protein sequences), XSTREAM (de novo tandem repeat detection and architecture modeling in protein sequences. All such tools are accessible through the internet at www.expasy.org/tools/. Other systems may include but are not limited to automated systems for modeling proteins based on its amino acid sequence, for example, ModPipe (available on the internet at: www.salilab.org), CPHmodels (available on the internet at: www.cbs.dtu.dk/services/CPHmodels/), 3D-JIGSAW (available on the internet at: www.bmm.icnet.uk/~3 djigsaw/), ESyPred3D (available on the internet at: www.fundp.ac.be/urbm/bioinfo/esypred/), or SDSC1 (available on the internet at: cl.sdsc.edu/hm.html). The invention is not limited to the specific methods used to of determine the three dimensional structure of the transporter protein.

The fluorophore, i.e., the fluorescent reporter, can be covalently bound to any one of the polypeptide loops that connect two transmembrane helices. In one embodiment, the fluorescent reporter is bound to the polypeptide loop that connects the first and second subunits of the structural inverted repeat of the transporter peptide. In another embodiment, the fluorescent reporter is bound to the polypeptide loop that does not connect the first and second subunits of the structural inverted repeat of the transporter peptide.

As used herein, "fluorophore" is used as it is in the art and refers to a molecule that emits light upon the absorption of energy. In general, a fluorophore of the present invention is any chemical moiety that exhibits an absorption maximum at or beyond 280 nm, and when covalently attached to a protein or other reagent retains its spectral properties. Fluorophores of the present invention include, without limitation; a pyrene (including any of the corresponding derivative compounds disclosed in U.S. Pat. No. 5,132,432, incorporated by reference), an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine (including any corresponding compounds in U.S. Pat. Nos. 4,981,977; 5,268,486; 5,569,587; 5,569,766; 5,486,616; 5,627,027; 5,808,044; 5,877,310; 6,002,003; 6,004,536; 6,008,373; 6,043,025; 6,127,134; 6,130,094; 6,133,445; 6,664,047; 6,974,873 and 6,977,305; and publications WO 02/26891, WO 97/40104, WO 99/51702, WO 01/21624; EP 1 065 250 A1, incorporated by reference), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896, incorporated by reference), a xanthene (including any corresponding compounds disclosed in U.S. Pat. Nos. 6,162,931; 6,130,101; 6,229,055; 6,339,392; 5,451,343 and 6,716,979, incorporated by reference), an oxazine (including any corresponding compounds disclosed in U.S. Pat. No. 4,714,763, incorporated by reference) or a benzoxazine, a carbazine (including any corresponding compounds disclosed in U.S. Pat. No. 4,810,636, incorporated by reference), a phenalenone, a coumarin (including an corresponding compounds disclosed in U.S. Pat. Nos. 5,696,157; 5,459,276; 5,501,980 and 5,830,912, incorporated by reference), a benzofuran (including an corresponding compounds disclosed in U.S. Pat. Nos. 4,603,209 and 4,849,362, incorporated by reference) and benzphenalenone (including any corresponding compounds disclosed in U.S. Pat. No. 4,812,409, incorporated by reference) and derivatives thereof. As used herein, oxazines include resorufins (including any corresponding compounds disclosed in U.S. Pat. No. 5,242,805, incorporated by reference), aminooxazinones, diaminooxazines, and their benzo-substituted analogs. Additional labeling moieties include, but are not limited to, those compounds that are described in United States Patent Publication No. 2006/0280652, published 14 Dec. 2006 and PCT Publication No. WO 2006/025887, which are incorporated by reference. Other fluorophores are described in RICHARD P. HAUGLAND, MOLECULAR PROBES HANDBOOK OF FLUORESCENT PROBES AND RESEARCH PRODUCTS (9th edition, CD-ROM, (September 2002), which is herein incorporated by reference.

When the fluorophore is a xanthene, the fluorophore is optionally a fluorescein, a rhodol (including any corresponding compounds disclosed in U.S. Pat. Nos. 5,227,487 and 5,442,045, incorporated by reference), or a rhodamine (including any corresponding compounds in U.S. Pat. Nos. 5,798,276; 5,846,737 and 6,562,632, incorporated by reference). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171, incorporated by reference). Alternatively, the fluorophore is a xanthene that is bound via a linkage that is a single covalent bond at the 9-position of the xanthene. Xanthenes also include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position.

Fluorophores for use in the present invention include, but are not limited to, xanthene (rhodol, rhodamine, fluorescein and derivatives thereof) coumarin, cyanine, pyrene, oxazine and borapolyazaindacene. Examples of xanthenes are sulfonated xanthenes, fluorinated xanthenes, sulfonated coumarins, fluorinated coumarins and sulfonated cyanines. The choice of the fluorophore will determine the absorption and fluorescence emission properties of the transporter protein or other labeling reagent complex. Physical properties of a fluorophore label include spectral characteristics (absorption, emission and stokes shift), fluorescence intensity, lifetime, polarization and photo-bleaching rate all of which can be used to distinguish one fluorophore from another.

Typically the fluorophore contains one or more aromatic or heteroaromatic rings, that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on fluorophores known in the art.

Non-limiting examples of fluorophores useful as reporter groups in this invention include acrylodan, fluorescein, coumarins, rhodamines, 5-TMRIA (tetramethylrhodamine-5-iodoacetamide), Quantum Red™ (R-phycoerythrin coupled to (9-(2(or4)-(N-(2-maleimdylethyl)-sulfonamidyl)-4(or 2)-sulfophenyl)-2,3,6,7,12,13,16,17-octahydro-(1H,5H, 11H,15H-xantheno(2,3,4-ij:5,6,7-i'j')diquinolizin-18-ium salt), Texas Red™ (9-(2(or4)-(N-(2-maleimdylethyl)-sulfonamidyl)-4(or 2)-sulfophenyl)-2,3,6,7,12,13,16,17-octahydro-(1H,5H,11H,15H-xantheno(2,3,4-ij:5,6,7-i'j') diquinolizin-18-ium salt), Cy™3 (2-(5-(1-(6-(N-(2-maleimdylethyl)-amino)-6-oxohexyl)-1,3-dihydro-3,3-dimethyl-5-sulfo-2H-indol-2-ylidene)-1,3-propyldienyl)-1-ethyl-3,3-dimethyl-5-sulfo-3H-indolium salt), N-((2-iodoacetoxy)ethyl)-N-methyl)amino-7-nitrobenzoxadiazole (IANBD), 6-acryloyl-2-dimethylaminonaphthalene (acrylodan), pyrene, Lucifer Yellow (6-amino-2,3-dihydro-2-(2-((iodoacetyl)amino)ethyl)-1,3-dioxo-1H-benz(de)isoquinoline-5,8-disulfonic acid salt), Cy™5 (2-(5-(1-(6-(N-(2-maleimdylethyl)-amino)-6-oxohexyl)-1,3-dihydro-3,3-dimethyl-5-sulfo-2H-indol-2-ylidene)-1,3-pentadienyl)-1-ethyl-3,3-dimethyl-5-sulfo-3H-indolium salt), Dapoxyl® (2-bromoacetamidoethyl)sulfonamide(4-(5-(4-dimethylaminophenyl)oxazol-2-yl)phenyl-N-(2-bromoacetamidoethyl)sulfonamide), (N-(4,4-difluoro-1,3,5,7-tetramethyl-4-bora-3a,4a-diaza-s-indacene-2-yl)-iodoacetamide (Bodipy507/545 IA), N-(4,4-difluoro-5,7-diphenyl-4-bora-3a,4a-diaza-s-indacene-3-propionyl)-N'-iodoacetylethylenediamine (BODIPY®. 530/550 IA), 5-((((2-iodoacetyl) amino)ethyl)amino)naphthalene-1-sulfonic acid (1,5-IAEDANS), carboxy-X-rhodamine, 5/6-iodoacetamide (XRIA 5,6), eosin, acridine orange, Alexa Fluor 350™, Alexa Fluor 405™, Alexa Fluor 430™, Alexa Fluor 488™, Alexa Fluor 500™, Alexa Fluor 514™, Alexa Fluor 532™, Alexa Fluor 546™, Alexa Fluor 555™, Alexa Fluor 568™, Alexa Fluor 594™, Alexa Fluor 610™, Alexa Fluor 633™, Alexa Fluor 635™, Alexa Fluor 647™, Alexa Fluor 660™, Alexa Fluor 680™, Alexa Fluor 700™ and Alexa Fluor 750™ Other fluorophores that exhibit environmentally-sensitive fluorescence properties include squaraines, coumarins, aza-coumarins, IAZCO, benzodiaxoazoles, and dyes derived from Nile Red such as INR. These fluorophores are described in pending U.S. Pregrant Publication No. 2006/0280652, which is incorporated herein by reference. Additional fluorophores are described in U.S. application Ser. No. 12/250,953, filed 14 Oct. 2008 and Ser. No. 12/124,553, filed 21 May 2008, respectively, both of which are incorporated by reference.

In one embodiment, the fluorescent reporter is a fluorescent protein. In a more specific embodiment, when a fluorescent protein is used as the reporter, the invention can also provide for fusion proteins comprising the transporter protein and a fluorescent protein as the reporter. The term "fluorescent protein" is readily understood in the art and simply means a protein that emits fluorescence at a detectable wavelength. Examples of fluorescent proteins that are part of fusion proteins of the current invention include, but are not limited to, green fluorescent proteins (GFP, AcGFP, ZsGreen), red-shifted GFP (rs-GFP), red fluorescent proteins (RFP, including DsRed2, HcRed1, dsRed-Express, cherry, tdTomato), yellow fluorescent proteins (YFP, Zsyellow), cyan fluorescent proteins (CFP, AmCyan), a blue fluorescent protein (BFP), ametrine, citrine, cerulean, turquoise, VENUS, teal fluorescent protein (TFP), LOV (light, oxygen or voltage) domains, and the phycobiliproteins, as well as the enhanced versions and mutations of these proteins. Fluorescent proteins as well as enhanced versions thereof are well known in the art and are commercially available. For some fluorescent proteins, "enhancement" indicates optimization of emission by increasing the protein's brightness, creating proteins that have faster chromophore maturation and/or alteration of dimerization properties. These enhancements can be achieved through engineering mutations into the fluorescent proteins.

The reporter group may be attached to the transporter protein by any conventional means known in the art. For example, the reporter group may be attached via amines or carboxyl residues on the protein. In one embodiment, N-hydroxy-succinimide (NHS) esters are used to crosslink the reporter group to primary amino groups on the transporter protein. Alternatively, cysteine or other amino acid groups may be engineered into the transporter protein to provide sites of attachment for the reporter group. Any thiol-reactive group known in the art may be used for attaching reporter groups such as fluorophores to a native, engineered, or mutated protein's cysteine. For example, acrylates, an iodoacetamide, bromoacetamide, or maleimide are well known thiol-reactive moieties that may be used for this purpose.

The fluorescent reporters, for example the phycobiliproteins, may be particularly useful for creating tandem dye labeled labeling reagents. In one embodiment of the current invention, therefore, the measurable signal of the fusion protein is actually a transfer of excitation energy (resonance energy transfer) from a donor molecule (e.g., a first fluorescent protein) to an acceptor molecule (e.g., a second fluorescent protein). In particular, the resonance energy transfer is in the form of fluorescence resonance energy transfer (FRET). When the fusion proteins of the present invention utilize FRET to measure or quantify analyte(s), one fluorescent protein of the fusion protein construct can be the donor, and the second fluorescent protein of the fusion protein construct can be the acceptor. The terms "donor" and "acceptor," when used in relation to FRET, are readily understood in the art. Namely, a donor is the molecule that will absorb a photon of light and subsequently initiate energy transfer to the acceptor molecule. The acceptor molecule is the molecule that receives the energy transfer initiated by the donor and, in turn, emits a photon of light. The efficiency of FRET is dependent upon the distance between the two fluorescent partners and can be expressed mathematically by: $E=R_0^6/(R_0^6+r^6)$, where "E" is the efficiency of energy transfer, "r" is the distance (in Angstroms) between the fluorescent donor/acceptor pair and "$R_0$" is the Förster distance (in Angstroms). The Förster distance, which can be determined experimentally by readily available techniques in the art, is the distance at which FRET is half of the maximum possible FRET value for a given donor/acceptor pair. A particularly useful combination is the phycobiliproteins disclosed in U.S. Pat. Nos. 4,520,110; 4,859,582; 5,055,556, incorporated by reference, and the sulforhodamine fluorophores disclosed in U.S. Pat. No. 5,798,276, or the sulfonated cyanine fluorophores disclosed in U.S. Pat. Nos. 6,977,305 and 6,974,873; or the sulfonated xanthene derivatives disclosed in U.S. Pat. No. 6,130,101, incorporated by reference and those combinations disclosed in U.S. Pat. No. 4,542,104, incorporated by reference.

A "spectral change" in a fluorophore reporter group may be monitored to detect analyte movement through the transporter protein. The "spectral change" that occurs upon analyte movement can be, but is not limited to, a change in fluorescence lifetime, fluorescence intensity, fluorescence polarization, and spectral shifts of fluorescence emission. Such spectral changes may result from changes in the local environment of the fluorophore, such as those resulting from changes in protein conformation. Environmentally-sensitive dyes such as acrylodan and IANBD are particularly useful in this respect. Other spectral changes may result from interactions with the analyte itself or from interactions with a second reporter group, for example when FRET (fluorescence resonance energy transfer) is used to monitor changes in distance between two fluorophores.

The term "detector" as used herein refers to any component, portion thereof, or system of components that can detect the detectable signal generated by the reporter group. In one specific embodiment, the detector can detect at least one property of light including, but not limited to, a charged coupled device (CCD), back-side thin-cooled CCD, front-side illuminated CCD, a CCD array, a photodiode, a photodiode array, a photo-multiplier tube (PMT), a PMT array, complimentary metal-oxide semiconductor (CMOS) sensors, CMOS arrays, a charge-injection device (CID), CID arrays, etc. The detector can be adapted to relay information to a data collection device for storage, correlation, and/or manipulation of data, for example, a computer, or other signal processing system.

The detected signal from the fluorescent reporter may simply be the measured signal, e.g., fluorescence, without any additional measurements or manipulations. Alternatively, the signal may be expressed as a difference, percentage or ratio of the measured value to a different measured value such as, but not limited to, a standard, baseline or response to another analyte. The signal when compared to another value may be negative, indicating a decrease in the amount of measured analyte(s). The quantities may also be expressed as a difference or ratio of the analyte(s) to itself, measured at a different point in time. The quantities of analytes may be determined directly from a generated signal, or the generated signal may be used in an algorithm, with the algorithm designed to correlate the value of the generated signals to the quantity of analyte(s) in the sample.

In one embodiment, the polypeptide loop connecting two transmembrane helices is linked to a fluorescent reporter without a linker peptide. In another embodiment, the polypeptide loop connecting two transmembrane helices is linked to the fluorescent reporter with at least one linker peptide, for example one or two peptide linkers. As used herein, a peptide linker is used to mean a polypeptide typically ranging from about 1 to about 120 amino acids in length that is designed to facilitate the functional connection of two distinct entities, such as the transporter protein and a fluorescent reporter. To be clear, a single amino acid can be considered a peptide linker peptide for the purposes of the present invention. In specific embodiments, the peptide linker comprises or in the alternative consists of amino acids numbering 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119 or 120 residues in length. Of course, the peptide linkers used in the fusion proteins of the present invention may comprise or in the alternative consist of amino acids numbering more than 120 residues in length. The length of the peptide linker(s), if present, are not necessarily critical to the function of the engineered protein, provided that the peptide linker permits a functional connection between the transporter protein and any fusion partner thereof, e.g., a fluorescent protein.

The term "functional connection" in the context of a linker peptide indicates a connection that facilitates folding of the polypeptides into a three dimensional structure that allows the linked fusion polypeptide to mimic some or all of the functional aspects or biological activities of the protein or portion thereof. For example, in the case of a labeled transporter protein, the linker may be used to create a single-chain fusion of a three dimensional structure that mimics the structure of the transporter and the fluorescent reporter. The term functional connection also indicates that the linked portions possess at least a minimal degree of stability, flexibility and/or tension that would be required for the transporter protein to function as desired.

In one embodiment of the present invention, when more than one linker peptide is used, each of the linker peptides comprises or consists of the same amino acid sequence. In another embodiment, when more than one linker peptide is used, each of the amino acid sequences of the peptide linkers are different from one another.

The transporter proteins that contain a structural inverted repeat can be from any plant source and the invention is not limited by the source of the transporter protein, i.e., the invention is not limited to the plant species from which transporter proteins that contain a structural inverted repeat normally occurs or is obtained. Examples of sources from which the transporter proteins that contain a structural inverted repeat may be derived include but are not limited to monocotyledonous plants that include, for example, Lolium, Zea, Triticum, Sorghum, Triticale, Saccharum, Bromus, Oryzae, Avena, Hordeum, Secale and Setaria. Other sources from which the transporter proteins that contain a structural inverted repeat may be derived include but are not limited to maize, wheat, barley, rye, rice, oat, sorghum and millet. Additional sources from which the transporter proteins that contain a structural inverted repeat may be derived include but are not limited to dicotyledenous plants that include but are not limited to Fabaceae, Solanum, Brassicaceae, especially potatoes, beans, cabbages, forest trees, roses, clematis, oilseed rape, sunflower, chrysanthemum, poinsettia, *arabidopsis*, tobacco, tomato, and antirrhinum (snapdragon), soybean, canola, sunflower and even basal land plant species, (the moss *Physcomitrella patens*). Additional sources also include gymnosperms.

It is understood that the invention is not limited to transporter proteins that contain a structural inverted repeat from the plant species listed herein, and that the invention encompasses proteins encoded by orthologous of genes in other species. As used herein, orthologous genes are genes from different species that perform the same or similar function and are believed to descend from a common ancestral gene. Proteins from orthologous genes, in turn, are the proteins encoded by the orthologs. As such the term "ortholog" may be to refer to a gene or a protein. Often, proteins encoded by orthologous genes have similar or nearly identical amino acid sequence identities to one another, and the orthologous genes themselves have similar nucleotide sequences, particularly when the redundancy of the genetic code is taken into account. Thus, by way of example, the ortholog of the Amt1 transporter would be an Amt1 transporter in another species of plant, regardless of the amino acid sequence of the two proteins.

In another aspect, the invention provides deletion variants wherein one or more amino acid residues in the transporter proteins that contain a structural inverted repeat or one or more fluorescent protein(s) are removed. Deletions can be effected at one or both termini of the transporter protein or one or more fluorescent protein(s), or with removal of one or more non-terminal amino acid residues of the transporter protein or one or more fluorescent protein(s).

The proteins of the present invention may also comprise substitution variants of a transporter protein that contain a structural inverted repeat of the fluorescent proteins used herein. Substitution variants include those polypeptides wherein one or more amino acid residues of the transporter proteins that contain a structural inverted repeat are removed and replaced with alternative residues. In general, the substitutions are conservative in nature. Conservative substitutions for this purpose may be defined as set out in the tables below. Amino acids can be classified according to physical properties and contribution to secondary and tertiary protein structure. A conservative substitution is recognized in the art as a substitution of one amino acid for another amino acid that has similar properties. Exemplary conservative substitutions are set out in below.

TABLE I

| Conservative Substitutions | |
|---|---|
| Side Chain Characteristic | Amino Acid |
| Aliphatic | |
| Non-polar | Gly, Ala, Pro, Iso, Leu, Val |
| Polar-uncharged | Cys, Ser, Thr, Met, Asn, Gln |
| Polar-charged | Asp, Glu, Lys, Arg |
| Aromatic | His, Phe, Trp, Tyr |
| Other | Asn, Gln, Asp, Glu |

Alternatively, conservative amino acids can be grouped as described in Lehninger (1975) Biochemistry, Second Edition; Worth Publishers, pp. 71-77, as set forth below.

TABLE II

Conservative Substitutions

| Side Chain Characteristic | Amino Acid |
|---|---|
| Non-polar (hydrophobic) | |
| Aliphatic: | Ala, Leu, Iso, Val, Pro |
| Aromatic: | Phe, Trp |
| Sulfur-containing: | Met |
| Borderline: | Gly |
| Uncharged-polar | |
| Hydroxyl: | Ser, Thr, Tyr |
| Amides: | Asn, Gln |
| Sulfhydryl: | Cys |
| Borderline: | Gly |
| Positively Charged (Basic): | Lys, Arg, His |
| Negatively Charged (Acidic): | Asp, Glu |

And still other alternative, exemplary conservative substitutions are set out below.

TABLE III

Conservative Substitutions

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

The invention therefore provides isolated peptides, with the peptides comprising an amino acid sequence at least about 75%, 80%, 85%, 86%, 87%, 88%, 89%, 90%, 91%, 92%, 93%, 94%, 95%, 96%, 97%, 98%, 99% or 100% identical to the amino acid sequences disclosed herein. For example, the invention provides for polypeptides comprising or consist of amino acid sequences that are 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:31.

A polypeptide having an amino acid sequence at least, for example, about 95% "identical" to a reference an amino acid sequence is understood to mean that the amino acid sequence of the polypeptide is identical to the reference sequence except that the amino acid sequence may include up to about five modifications per each 100 amino acids of the reference amino acid sequence. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using well known techniques. While there are several methods to measure identity between two polynucleotide or polypeptide sequences, the term "identity" is well known to skilled artisans (Carillo (1988) J. Applied Math. 48, 1073). Examples of computer program methods to determine identity and similarity between two sequences include, but are not limited to, GCG program package (Devereux (1984) Nucleic Acids Research 12, 387), BLASTP, ExPASy, BLASTN, FASTA (Atschul (1990) J. Mol. Biol. 215, 403) and FASTDB. Examples of methods to determine identity and similarity are discussed in Michaels (2011) Current Protocols in Protein Science, Vol. 1, John Wiley & Sons.

In one embodiment of the present invention, the algorithm used to determine identity between two or more polypeptides is BLASTP. In another embodiment of the present invention, the algorithm used to determine identity between two or more polypeptides is FASTDB, which is based upon the algorithm of Brutlag (1990) Comp. App. Biosci. 6, 237-245). In a FASTDB sequence alignment, the query and reference sequences are amino sequences. The result of sequence alignment is in percent identity. In one embodiment, parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the reference sequence is shorter or longer than the query sequence because of N-terminus or C-terminus additions or deletions, but not because of internal additions or deletions, a manual correction can be made, because the FASTDB program does not account for N-terminus and C-terminus truncations or additions of the reference sequence when calculating percent identity. For query sequences truncated at the N- or C-termini, relative to the reference sequence, the percent identity is corrected by calculating the number of residues of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the reference sequence that extend past the N- or C-termini of the query sequence may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue query sequence is aligned with a 100 residue reference sequence to determine percent identity. The deletion occurs at the N-terminus of the query sequence and therefore, the FASTDB alignment does not show a match/alignment of the first 10 residues at the N-terminus. The 10 unpaired residues represent 10% of the reference sequence (number of residues at the N- and C-termini not matched/total number of residues in the reference sequence) so 10% is subtracted from the percent identity score calculated by the FASTDB program. If the remaining 90 residues were perfectly matched (100% alignment) the final percent identity would be 90% (100% alignment—10% unmatched overhang). In another example, a 90 residue query sequence is compared with a 100 reference sequence, except that the deletions are internal deletions. In this case the percent identity calculated by FASTDB is not manually corrected, since there are no residues at the N- or C-termini of the subject sequence that are not matched/aligned with the query. In still another example, a 110 amino acid query sequence is aligned with a 100 residue reference sequence to determine percent identity. The addition in the query occurs at the N-terminus of the query sequence and therefore, the FASTDB alignment may not show a match/alignment of the first 10 residues at the N-terminus. If the remaining 100 amino acid residues of the query sequence have 95% identity to the entire length of the reference sequence, the N-terminal addition of the query would be ignored and the percent identity of the query to the reference sequence would be 95%.

As used herein, the terms "correspond(s) to" and "corresponding to," as they relate to sequence alignment, are intended to mean enumerated positions within a reference protein, e.g., wild-type Amt1, and those positions in a modified Amt1 that align with the positions on the reference protein. Thus, when the amino acid sequence of a subject protein is aligned with the amino acid sequence of a reference protein, the amino acids in the subject sequence that "correspond to" certain enumerated positions of the reference sequence are those that align with these positions of the reference sequence, but are not necessarily in these exact numerical positions of the reference sequence. Methods for aligning sequences for determining corresponding amino acids between sequences are described herein.

The use of 'tweakable' fluorophores that are sensitive to conformational changes in the recognition element may also be used. For example, GFP is an extraordinarily stable protein, and it is protected from bulk medium by a soda can-like cage formed by a β-barrel that consists of 11 β-strands. The chromophore, a p-hydroxybenzylidene-imidazolidone, develops by autocatalysis from a hexapeptide. The chromophore interacts with residues inside the cage for example by hydrogen bonding (H148 interaction with the hydroxyl of Y66, R96 with the imidazolidone, Y145 stabilizes the chromophore by an edge-face interaction with Y66, and E222 with the hydroxyl of S65). GFP exists in two ground-state forms, called A and B, and these states interconvert depending on the environment such as local pH. The two states have different spectral properties, i.e., have two visible absorption bands at 478 and 398 nm (508 nm emission). In the ground state, interconversion of the states is relatively slow, but occurs much faster in the excited state. Further analysis indicates that the interconversion involves proton transfer followed by structural rearrangements. Interestingly, mutation at S65 or E222 result in a loss of the absorption maximum at 398 nm, supporting a role of protonation of the chromophore or adjacent residues in determining the 'state' of the chromophores and thus its absorption properties.

One example of a GFP protein is enhanced GFP ("eGFP") from

```
                                              (SEQ ID NO: 32)
MVSKGEELFT  GVVPILVELD  GDVNGHKFSV  SGEGEGDATY

GKLTLKFICT  TGKLPVPWPT  LVTTLTYGVQ  CFSRYPDHMK

QHDFFKSAMP  EGYVQERTIF  FKDDGNYKTR  AEVKFEGDTL

VNRIELKGID  FKEDGNILGH  KLEYNYNSHN  VYIMADKQKN

GIKVNFKIRH  NIEDGSVQLA  DHYQQNTPIG  DGPVLLPDNH

YLSTQSALSK  DPNEKRDHMV  LLEFVTAAGI  TLGMDELYK
```

This observation opens the possibility to generating fluorophores that are environmentally sensitive and that can report conformational changes in a recognition element. Interestingly, an earlier reported mutant has in the positions of Y145 in the β-barrel contained six additional residues, yet the mutant protein retained fluorescence. Previous studies generated circularly permuted GFP and fused various polypeptides at this site. The circular permuted forms were sensitive to acidification, potentially caused by protonation of a non-chromophoric site leading to a conformational change, changes in hydrogen bonds, or electrostatic repulsion displacing a proton from the phenolic hydroxyl of the chromophores. With the idea that fusion of a recognition element acid quenching may be affected by the presence of polypeptides that depending on their conformation may protect the chromophores from bulk medium access, a calmodulin sensor was develop with a single fluorophore to detect calcium. In a similar approach, the same group also constructed a functional zinc sensor by fusing the circular permuted GFP to a zinc finger domain.

Many groups further improved this type of sensor in several steps. See for example, Nagai T, Sawano A, Park E S, Miyawaki A. 2001. Circularly permuted green fluorescent proteins engineered to sense Ca2+. *Proc. Natl. Acad. Sci. USA* 98:3197-202. These optimizations have lead to calcium sensors with a significantly improved dynamic range (ΔF/F0) of over 10-fold. The dynamic range is important in the context of high signal-to-noise ratio (SNR), which is required for in vivo applications. The SNR of these sensors is ~N1/2 ΔF/F. SNR increases with the square root of the number of photons collected and with the dynamic range ΔF/F. One group lab carried out a careful in vivo comparison of FRET and cpGFP calcium sensors and showed that for example the FRET sensor TN-XL was significantly brighter compared with GCaMP2, thus providing higher SNR (See, Mao T, O'Connor D H, Scheuss V, Nakai J, Svoboda K. 2008. Characterization and subcellular targeting of GCaMP-type genetically-encoded calcium indicators. PLoS ONE 3:e1796). Comparison of performance indicates that in order to achieve high signal to noise and being able to detect action potentials with high confidence further improvements is necessary. SNR is apparently a moving target since the sensors are continuously improved regarding both brightness and dynamic range. Similar as for several FRET sensors, CpGFP sensor can be used for monitoring local calcium levels, e.g. GCaMP2 has been targeted to plasma membrane subdomains by fusion to Na+ pump isoforms (Lee M Y, Song H, Nakai J, Ohkura M, Kotlikoff M I, et al. 2006. Local subplasma membrane Ca2+ signals detected by a tethered Ca2+ sensor. *Proc. Natl. Acad. Sci. USA* 103:13232-7).

Circular permutation of EGFP and deletion of several residues resulted in a significant opening of ~5 Å×10 Å in the barrel providing bulk solvent access. (Akerboom J, Rivera J D, Guilbe M M, Malave E C, Hernandez H H, et al. 2009. Crystal structures of the GCaMP calcium sensor reveal the mechanism of fluorescence signal change and aid rational design. *J. Biol. Chem.* 284:6455-64). The tyrosine side chain at the tip of the chromophore pointed towards the opening. A dimer was discovered in which the M13 calmodulin-binding peptides interact with the calcium-loaded calmodulin of the other subunit in the dimer, respectively. Biochemical characterization showed that in the absence of calcium GCaMP2 predominantly existed in the monomeric form while in the presence of calcium, both monomeric and dimeric were observed. While in the dimer, channels provide solvent access, the opening is occluded in the monomeric conformation by the linkers of the fusion with calmodulin. As discussed above the main differences between open and closed forms will affect solvent access and thus affect protonation of the phenolate oxygen of the chromophores.

The concept of using circular permuted GFP variants has successfully been used to construct sensors for inositol-1,3,4,5-tetrakisphosphate (Sakaguchi R, Endoh T, Yamamoto S, Tainaka K, Sugimoto K, et al. 2009. A single circularly permuted GFP sensor for inositol-1,3,4,5-tetrakisphosphate based on a split PH domain. Bioorg Med Chem 17:7381-6), for the ATP/ADP ratio (Berg J, Hung Y P, Yellen G. 2009. A genetically encoded fluorescent reporter of ATP:ADP ratio. Nat Methods 6:161-6) as well as for the transition metals Cu2+/Zn2+(Mizuno T, Murao K, Tanabe Y, Oda M, Tanaka T. 2007. Metal-ion-dependent GFP emission in vivo by combining a circularly permutated green fluorescent protein with an engineered metal-ion-binding coiled-coil. J. Am. Chem. Soc. 129:11378-83). Another group used a similar approach to construct cpGFP-based voltage sensors (Gautam S G, Perron A, Mutoh H, Knopfel T. 2009. Exploration of fluorescent protein voltage probes based on circularly permuted fluorescent proteins. Front Neuroeng 2:14). Besides green cpGFP, cyan cpCFP, and yellow cpYFP-Venus variants, now also red cpTomato variants are available expanding the possibility to develop such sensors and for multiplexing analysis, e.g., for the parallel use of affinity mutants in a single cells or for measuring multiple analytes in parallel (Li Y, Sierra A M, Ai H W, Campbell R E. 2008. Identification of sites within a monomeric red fluorescent protein that tolerate peptide insertion and testing of corresponding circular permutations. Photochem. Photobiol. 84:111-9). Circular permuted fluorescent reporters can thus be used in the methods of the present invention.

One example of the engineered proteins of the present invention is seen in the amino acid sequence of SEQ ID NO:28. SEQ ID NO:28 is an engineered ammonium transporter protein fused with a cpGFP. In the amino acid sequence of SEQ ID NO:28, the portion with the sequence below is the cpGFP portion of the engineered protein.

```
                                         (SEQ ID NO: 31)
NVYIKADKQK NGIKANFKIR HNIEDGGVQL AYHYQQNTPI

GDGPVLLPDN HYLSVQSKLS KDPNEKRDHM VLLEFVTAAG

ITLGMDELYK GGTGGSMVSK GEELFTGVVP ILVELDGDVN

GHKFSVSGEG EGDATYGKLT LKFICTTGKL PVPWPTLVTT

LTYGVQCFSR YPDHMKQHDF FKSAMPEGYI QERTIFFKDD

GNYKTRAEVK FEGDTLVNRI ELKGIDFKED GNILGHKLEY

N
```

The invention also provides isolated nucleic acids, with the nucleic acids comprising polynucleotide sequence at least about 75%, 80%, 85%, 86%, 87%, 88%, 89%, 90%, 91%, 92%, 93%, 94%, 95%, 96%, 97%, 98%, 99% or 100% identical to the polynucleotide sequences disclosed herein.

As a practical matter, whether any particular nucleic acid molecule is at least 80%, 85%, 90%, 92%, 95%, 96%, 97%, 98% or 99% identical to a disclosed nucleic acid can be determined conventionally using known computer programs a discussed herein. For example, percent identity can be determined using the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, Advances in Applied Mathematics 2: 482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed. Methods for correcting percent identity of the of polynucleotides are the same as those described and disclosed herein with respect to polypeptides.

The engineered proteins of the present invention may or may not contain additional elements that, for example, may include but are not limited to regions to facilitate purification. For example, "histidine tags" ("his tags") or "lysine tags" may be appended to the engineered protein. Examples of histidine tags include, but are not limited to hexaH, heptaH and hexaHN. Examples of lysine tags include, but are not limited to pentaL, heptaL and FLAG. Such regions may be removed prior to final preparation of the engineered protein. Other examples of a fusion partner for the engineered proteins of the present invention include, but are not limited to, glutathione S-transferase (GST) and alkaline phosphatase (AP).

The addition of peptide moieties to engineered proteins, whether to engender secretion or excretion, to improve stability and to facilitate purification or translocation, among others, is a familiar and routine technique in the art and may include modifying amino acids at the terminus to accommodate the tags. For example the N-terminus amino acid may be modified to, for example, arginine and/or serine to accommodate a tag. Of course, the amino acid residues of the C-terminus may also be modified to accommodate tags. One particularly useful fusion protein comprises a heterologous region from immunoglobulin that can be used solubilize proteins.

Other types of fusion proteins provided by the present invention include but are not limited to, fusions with secretion signals and other heterologous functional regions. Thus, for instance, a region of additional amino acids, particularly charged amino acids, may be added to the N-terminus of the engineered protein to improve stability and persistence in the host cell, during purification or during subsequent handling and storage.

The engineered proteins of the current invention may be recovered and purified from recombinant cell cultures by well-known methods including, but not limited to, ammonium sulfate or ethanol precipitation, acid extraction, anion or cation exchange chromatography, phosphocellulose chromatography, hydrophobic interaction chromatography, affinity chromatography, e.g., immobilized metal affinity chromatography (IMAC), hydroxylapatite chromatography and lectin chromatography. High performance liquid chromatography ("HPLC") may also be employed for purification. Well-known techniques for refolding protein may be employed to regenerate active conformation when the fusion protein is denatured during isolation and/or purification.

Engineered proteins of the present invention include, but are not limited to, products of chemical synthetic procedures and products produced by recombinant techniques from a prokaryotic or eukaryotic host, including, for example, bacterial, yeast, higher plant, insect and mammalian cells. Depending upon the host employed in a recombinant production procedure, the engineered proteins of the present invention may be glycosylated or may be non-glycosylated. In addition, engineered proteins of the invention may also include an initial modified methionine residue, in some cases as a result of host-mediated processes.

The present invention also provides for nucleic acids encoding some of the engineered proteins of the present invention.

The invention also relates to isolated nucleic acids and to constructs comprising these nucleic acids. The nucleic acids of the invention can be DNA or RNA, for example, mRNA. The nucleic acid molecules can be double-stranded or single-stranded; single stranded RNA or DNA can be the coding, or sense, strand or the non-coding, or antisense, strand. In particular, the nucleic acids may encode any engineered protein of the invention. For example, the nucleic acids of the invention include polynucleotide sequences that encode the engineered proteins that contain or comprise glutathione-S-transferase (GST) fusion protein, poly-histidine (e.g., $His_6$), poly-HN, poly-lysine, etc. If desired, the nucleotide sequence of the isolated nucleic acid can include additional non-coding sequences such as non-coding 3' and 5' sequences (including regulatory sequences, for example).

Examples of some of the nucleic acids of the present invention include bit are not limited to those sequences exemplified in the nucleic acid sequences of SEQ ID NO:29 and SEQ ID NO:30, where the nucleic acid sequence of SEQ ID NO:29 encodes the amino acid sequence of SEQ ID NO:28.

The present invention also comprises vectors containing the nucleic acids encoding the engineered proteins of the present invention. As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Examples of vectors include but are not limited to those capable of autonomous replication and expression of the structural gene products present in the DNA segments to which they are operably joined.

In certain respects, the vectors to be used are those for expression of polynucleotides and proteins of the present invention. Generally, such vectors comprise cis-acting control regions effective for expression in a host operatively linked to the polynucleotide to be expressed. Appropriate trans-acting factors are supplied by the host, supplied by a complementing vector or supplied by the vector itself upon introduction into the host.

A great variety of expression vectors can be used to express the proteins of the invention. Such vectors include chromosomal, episomal and virus-derived vectors, e.g., vectors derived from bacterial plasmids, from bacteriophage, from yeast episomes, from yeast chromosomal elements, from viruses such as adeno-associated virus, lentivirus, baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. All may be used for expression in accordance with this aspect of the present invention. Generally, any vector suitable to maintain, propagate or the fusion proteins in a host may be used for expression in this regard.

The DNA sequence in the expression vector is operatively linked to appropriate expression control sequence(s) including, for instance, a promoter to direct mRNA transcription. Representatives of such promoters include, but are not limited to, the phage lambda PL promoter, the E. coli lac, trp and tac promoters, HIV promoters, the SV40 early and late promoters and promoters of retroviral LTRs, to name just a few of the well-known promoters. In general, expression constructs will contain sites for transcription, initiation and termination and, in the transcribed region, a ribosome binding site for translation. The coding portion of the mature transcripts expressed by the constructs will include a translation initiating AUG at the beginning and a termination codon (UAA, UGA or UAG) appropriately positioned at the end of the polypeptide to be translated.

In addition, the constructs may contain control regions that regulate, as well as engender expression. Generally, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors may contain one or more selectable marker genes to provide a phenotypic trait for selection of transformed host cells. Preferred markers include dihydrofolate reductase or neomycin resistance for eukaryotic cell culture, and tetracycline, kanamycin or ampicillin resistance genes for culturing E. coli and other bacteria.

Examples of vectors that may be useful for engineered proteins include, but are not limited to, pPZP, pZPuFLIPs, pCAMBIA, and pRT to name a few.

Examples of vectors for expression in yeast S. cerevisiae include pDRFLIP,s, pDR196, pYepSecl (Baldari (1987) EMBO J. 6, 229-234), pMFa (Kurjan (1982) Cell 30, 933-943), pJRY88 (Schultz (1987) Gene 54, 115-123), pYES2 (Invitrogen) and picZ (Invitrogen).

Alternatively, the engineered proteins can be expressed in insect cells using baculovirus expression vectors. Baculovirus vectors available for expression of proteins in cultured insect cells (e.g., SF9 cells) include the pAc series (Smith (1983) Mol. Cell. Biol. 3, 2156 2165) and the pVL series (Lucklow (1989) Virology 170, 31-39).

The nucleic acid molecules of the invention can be "isolated." As used herein, an "isolated" nucleic acid molecule or nucleotide sequence is intended to mean a nucleic acid molecule or nucleotide sequence that is not flanked by nucleotide sequences normally flanking the gene or nucleotide sequence (as in genomic sequences) and/or has been completely or partially removed from its native environment (e.g., a cell, tissue). For example, nucleic acid molecules that have been removed or purified from cells are considered isolated. In some instances, the isolated material will form part of a composition (for example, a crude extract containing other substances), buffer system or reagent mix. In other circumstances, the material may be purified to near homogeneity, for example as determined by PAGE or column chromatography such as HPLC. Thus, an isolated nucleic acid molecule or nucleotide sequence can includes a nucleic acid molecule or nucleotide sequence which is synthesized chemically, using recombinant DNA technology or using any other suitable method. To be clear, a nucleic acid contained in a vector would be included in the definition of "isolated" as used herein. Also, isolated nucleotide sequences include recombinant nucleic acid molecules (e.g., DNA, RNA) in heterologous organisms, as well as partially or substantially purified nucleic acids in solution. "Purified," on the other hand is well understood in the art and generally means that the nucleic acid molecules are substantially free of cellular material, cellular components, chemical precursors or other chemicals beyond, perhaps, buffer or solvent. "Substantially free" is not intended to mean that other components beyond the novel nucleic acid molecules are undetectable. The nucleic acid molecules of the present invention may be isolated or purified. Both in vivo and in vitro RNA transcripts of a DNA molecule of the present invention are also encompassed by "isolated" nucleotide sequences.

The invention also provides nucleic acid molecules that hybridize under high stringency hybridization conditions, such as for selective hybridization, to the nucleotide sequences described herein (e.g., nucleic acid molecules which specifically hybridize to a nucleotide sequence encoding engineered proteins described herein). Hybridization probes include synthetic oligonucleotides which bind in a base-specific manner to a complementary strand of nucleic acid.

Such nucleic acid molecules can be detected and/or isolated by specific hybridization e.g., under high stringency conditions. "Stringency conditions" for hybridization is a term of art that refers to the incubation and wash conditions, e.g., conditions of temperature and buffer concentration, which permit hybridization of a particular nucleic acid to a second nucleic acid; the first nucleic acid may be perfectly complementary, i.e., 100%, to the second, or the first and second may share some degree of complementarity, which is less than perfect, e.g., 60%, 75%, 85%, 95% or more. For example, certain high stringency conditions can be used which distinguish perfectly complementary nucleic acids from those of less complementarity.

"High stringency conditions", "moderate stringency conditions" and "low stringency conditions" for nucleic acid hybridizations are explained in Current Protocols in Molecular Biology, John Wiley & Sons). The exact conditions which determine the stringency of hybridization depend not only on ionic strength, e.g., 0.2×SSC, 0.1×SSC of the wash buffers, temperature, e.g., room temperature, 42° C., 68° C., etc., and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions may be determined empirically.

By varying hybridization conditions from a level of stringency at which no hybridization occurs to a level at which hybridization is first observed, conditions which will allow a given sequence to hybridize with the most similar sequences in the sample can be determined. Exemplary conditions are described in Krause (1991) Methods in Enzymology, 200: 546-556. Washing is the step in which conditions are usually set so as to determine a minimum level of complementarity of the hybrids. Generally, starting from the lowest temperature at which only homologous hybridization occurs, each degree (° C.) by which the final wash temperature is reduced, while holding SSC concentration constant, allows an increase by 1% in the maximum extent of mismatching among the sequences that hybridize. Generally, doubling the concentration of SSC results in an increase in Tm. Using these guidelines, the washing temperature can be determined empirically for high, moderate or low stringency, depending on the level of mismatch sought. Exemplary high stringency conditions include, but are not limited to, hybridization in 50% formamide, 1 M NaCl, 1% SDS at 37° C., and a wash in 0.1×SSC at 60° C. Example of progressively higher stringency conditions include, after hybridization, washing with 0.2×SSC and 0.1% SDS at about room temperature (low stringency conditions); washing with 0.2×SSC, and 0.1% SDS at about 42° C. (moderate stringency conditions); and washing with 0.1×SSC at about 68° C. (high stringency conditions). Washing can be carried out using only one of these conditions, e.g., high stringency conditions, washing may encompass two or more of the stringency conditions in order of increasing stringency. Optimal conditions will vary, depending on the particular hybridization reaction involved, and can be determined empirically.

Equivalent conditions can be determined by varying one or more of the parameters given as an example, as known in the art, while maintaining a similar degree of identity or similarity between the target nucleic acid molecule and the primer or probe used. Hybridizable nucleotide sequences are useful as probes and primers for identification of organisms comprising a nucleic acid of the invention and/or to isolate a nucleic acid of the invention, for example. The term "primer" is used herein as it is in the art and refers to a single-stranded oligonucleotide which acts as a point of initiation of template-directed DNA synthesis under appropriate conditions in an appropriate buffer and at a suitable temperature. The appropriate length of a primer depends on the intended use of the primer, but typically ranges from about 15 to about 30 nucleotides. Short primer molecules generally require cooler temperatures to form sufficiently stable hybrid complexes with the template. A primer need not reflect the exact sequence of the template, but must be sufficiently complementary to hybridize with a template. The term "primer site" refers to the area of the target DNA to which a primer hybridizes. The term "primer pair" refers to a set of primers including a 5' (upstream) primer that hybridizes with the 5' end of the DNA sequence to be amplified and a 3' (downstream) primer that hybridizes with the complement of the 3' end of the sequence to be amplified.

The present invention also relates to host cells containing the above-described constructs. The host cell can be a eukaryotic cell, such as a plant cell or yeast cell, or the host cell can be a prokaryotic cell, such as a bacterial cell. The host cell can be stably or transiently transfected with the construct. The polynucleotides may be introduced alone or with other polynucleotides. Such other polynucleotides may be introduced independently, co-introduced or introduced joined to the polynucleotides of the invention. As used herein, a "host cell" is a cell that normally does not contain any of the nucleotides of the present invention and contains at least one copy of the nucleotides of the present invention. Thus, a host cell as used herein can be a cell in a culture setting or the host cell can be in an organism setting where the host cell is part of an organism, organ or tissue.

If a prokaryotic expression vector is employed, then the appropriate host cell would be any prokaryotic cell capable of expressing the cloned sequences. Suitable prokaryotic cells include, but are not limited to, bacteria of the genera *Escherichia, Bacillus, Pseudomonas, Staphylococcus*, and *Streptomyces*.

If a eukaryotic expression vector is employed, then the appropriate host cell would be any eukaryotic cell capable of expressing the cloned sequence. In one embodiment, eukaryotic cells are the host cells. Eukaryotic host cells include, but are not limited to, insect cells, HeLa cells, Chinese hamster ovary cells (CHO cells), African green monkey kidney cells (COS cells), human 293 cells, and murine 3T3 fibroblasts.

In addition, a yeast cell may be employed as a host cell. Yeast cells include, but are not limited to, the genera *Saccharomyces, Pichia* and *Kluveromyces*. In one embodiment, the yeast hosts are *S. cerevisiae* or *P. pastoris*. Yeast vectors may contain an origin of replication sequence from a 2T yeast plasmid, an autonomously replication sequence (ARS), a promoter region, sequences for polyadenylation, sequences for transcription termination and a selectable marker gene. Shuttle vectors for replication in both yeast and *E. coli* are also included herein.

Introduction of a construct into the host cell can be affected by calcium phosphate transfection, DEAE-dextran mediated transfection, cationic lipid-mediated transfection, electroporation, transduction, infection or other methods.

Other examples of methods of introducing nucleic acids into host organisms take advantage TALEN technology to effectuate site-specific insertion of nucleic actions. TALENs are proteins that have been engineered to cleave nucleic acids at a specific site in the sequence. The cleavage sites of TALENs are extremely customizable and pairs of TALENs can be generated to create double-stranded breaks (DSBs) in nucleic acids at virtually any site in the nucleic acid. See Bogdanove and Voytas, Scienc, 333:1843-1846 (2011), which incorporated by reference herein Transformants carrying the expression vectors are selected based on the above-mentioned selectable markers. Repeated clonal selection of the transformants using the selectable markers allows selection of stable cell lines expressing the fusion proteins constructs. Increased concentrations in the selection medium allows gene amplification and greater expression of the desired fusion proteins. The host cells, for example *E. coli* cells, containing the recombinant fusion proteins can be produced by cultivating the cells containing the fusion proteins expression vectors constitutively expressing the engineered proteins constructs.

The present invention also provides for transgenic organisms, including but not limited to plants, animals and prokaryotic organisms. The transgenic animals, all of whose germ and somatic cells would contain the DNA construct of the invention, would include vertebrates in general. Examples of transgenic animals include but are not limited to mammals such as non-human primates, mice, sheep, pigs, cattle, goats, guinea pigs, rodents, e.g., rats, and the like. The term transgenic animal also includes animals in all stages of development, including embryonic and fetal stages.

Such transgenic animals may be obtained, for example, by injecting the DNA constructs of the present invention into a fertilized egg which is allowed to develop into an adult animal. To prepare a transgenic animal, a few hundred DNA molecules are injected into the pro-nucleus of a fertilized one cell egg. The micro injected eggs are then transferred into the oviducts of pseudopregnant foster mothers and allowed to develop. It has been reported by Brinster et al., Proc. Natl. Acad. Sci. USA 82:4438-4442 (1985), that about 25% of mice which develop will inherit one or more copies of the micro injected DNA. Alternatively, the transgenic animals may be obtained by utilizing recombinant ES cells for the generation of the transgenes, as described by Gossler et al., Proc. Natl. Acad. Sci. USA 83:9065-9069 (1986). The offspring may be analyzed for the integration of the transgene by isolating genomic DNA from tail tissue and the fragment coding for the engineered proteins identified by conventional DNA-hybridization techniques (Southern, J. Mol. Biol. 98:503-517 (1975)). Animals positive for the nucleic acid encoding the engineered protein are further bred to expand the colonies of transgenic mice. General and specific examples of methods of preparing transgenic animals are disclosed in U.S. Pat. Nos. 5,602,299, 5,366,894, 5,464,758, 5,569,827, WO96/40896 (U.S. application Ser. No. 08/480, 653); WO96/40895 (U.S. application Ser. Nos. 08/486,018 and 08/486,536); WO93/14200 (U.S. application Ser. Nos. 07/817,584 and 07/915,469); WO95/03397 (U.S. application Ser. No. 08/096,944); WO95/25792 (U.S. application Ser. No. 08/215,083); EP 0 717 105 (U.S. application Ser. No. 08/358,627); and Hogan et al., Manipulating the Mouse Embryo, Cold Spring Harbor Laboratory, Cold Spring Harbor, N.Y., 1986); Hammer et al., Cell 63:1099-1112 (1990). Once obtained, the transgenic animals which contain the nucleic acid encoding the engineered protein may be analyzed by immunohistology for evidence of the engineered protein expression.

The present invention also provides for transgenic plants or plant tissue comprising transgenic plant cells, i.e. comprising stably integrated into their genome, an above-described nucleic acid molecule, expression cassette or vector of the invention. The present invention also provides transgenic plants, plant cells or plant tissue obtainable by a method for their production as outlined below.

In one embodiment, the present invention provides a method for producing transgenic plants, plant tissue or plant cells comprising the introduction of a nucleic acid molecule, expression cassette or vector of the invention into a plant cell and, optionally, regenerating a transgenic plant or plant tissue therefrom. The transgenic plants expressing the engineered protein can be of use in monitoring the transport or movement of analytes throughout and between the organs of an organism, such as to or from the soil. The transgenic plants expressing transporters of the invention can be of use for investigating metabolic or transport processes of, e.g., organic compounds with a timely and spatial resolution.

Examples of species of plants that may be used for generating transgenic plants include but are not limited to monocotyledonous plants including seed and the progeny or propagules thereof, for example Lolium, Zea, Triticum, Sorghum, Triticale, Saccharum, Bromus, Oryzae, Avena, Hordeum, Secale and Setaria. Especially useful transgenic plants are maize, wheat, barley plants and seed thereof. Dicotyledenous plants are also within the scope of the present invention include but are not limited to the species Fabaceae, Solanum, Brassicaceae, especially potatoes, beans, cabbages, forest trees, roses, clematis, oilseed rape, sunflower, chrysanthemum, poinsettia and antirrhinum (snapdragon). The plant may be crops, such as a food crops, feed crops or biofuels crops. Exemplary important crops may include soybean, cotton, rice, millet, sorghum, sugarcane, sugar beet, tomato, grapevine, citrus (orange, lemon, grapefruit, etc), lettuce, alfalfa, fava bean and strawberries, rapeseed, cassava, miscanthus and switchgrass to name a few.

Methods for the introduction of foreign nucleic acid molecules into plants are well-known in the art. For example, plant transformation may be carried out using Agrobacterium-mediated gene transfer, microinjection, electroporation or biolistic methods as it is, e.g., described in Potrykus and Spangenberg (Eds.), Gene Transfer to Plants. Springer Verlag, Berlin, N.Y., 1995. Therein, and in numerous other references, useful plant transformation vectors, selection methods for transformed cells and tissue as well as regeneration techniques are described which are known to the person skilled in the art and may be applied for the purposes of the present invention.

In another aspect, the invention provides harvestable parts and methods to propagation material of the transgenic plants according to the invention which contain transgenic plant cells as described above. Harvestable parts can be in principle any useful part of a plant, for example, leaves, stems, fruit, seeds, roots etc. Propagation material includes, for example, seeds, fruits, cuttings, seedlings, tubers, rootstocks etc.

The present invention also provides methods of producing any of the engineered proteins of the present invention, the method comprising culturing a host cell in conditions that promote protein expression and recovering the engineered protein from the culture, wherein the host cell comprises a vector encoding the engineered protein.

The protein production methods generally comprise culturing the host cells of the invention under conditions such that the engineered protein is expressed, and recovering said protein. The culture conditions required to express the proteins of the current invention are dependent upon the host cells that are harboring the polynucleotides of the current invention. The culture conditions for each cell type are well-known in the art and can be easily optimized, if necessary. For example, a nucleic acid encoding an engineered protein of the invention, or a construct comprising such nucleic acid, can be introduced into a suitable host cell by a method appropriate to the host cell selected, e.g., transformation, transfection, electroporation, infection, such that the nucleic acid is operably linked to one or more expression control elements as described herein. Host cells can be maintained under conditions suitable for expression in vitro or in vivo, whereby the encoded engineered protein is produced. For example host cells may be maintained in the presence of an inducer, suitable media supplemented with appropriate salts, growth factors, antibiotic, nutritional supplements, etc., which may facilitate protein expression. In additional embodiments, the engineered proteins of the invention can be produced by in vitro translation of a nucleic acid that encodes the engineered protein, by chemical synthesis or by any other suitable method. If desired, the engineered protein can be isolated from the host cell or other environment in which the protein is produced or secreted. It should therefore be appreciated that the methods of producing the engineered proteins encompass expression of the polypeptides in a host cell of a transgenic plant. See U.S. Pat. Nos. 6,013,857, 5,990,385, and 5,994,616.

The invention also provides for methods of monitoring analyte movement in a sample, comprising contacting the sample with an engineered protein of the present invention and subsequently measuring the fluorescent signal, which may or may not include FRET. Accordingly, the engineered proteins can be used in sensors for measuring a target analytes in a sample, with the sensors comprising the engineered proteins of the present invention.

The target analytes can be any molecule or compound where the movement or concentration is desired to be measured or monitored. Whichever molecule or ion that the transporter peptide normally transports is capable of being monitored or measured. For example, if ammonium transporter is being engineered, then ammonium can be monitored or measured. Examples of classes of analytes that might be measured, depending on the transporter protein being engineered, include, but are not limited to amino acids, peptides, polypeptides, proteins, carbohydrates, lipids, nucleotides, oligonucleotides, polynucleotides, glycoproteins or proteoglycans, lipoproteins, lipopolysaccharides, drugs, drug metabolites, small organic molecules, inorganic molecules and natural or synthetic polymers. As used herein, "carbohydrate" includes, but is not limited to monosaccharides, disaccharides, oligosaccharides and polysaccharides. "Carbohydrate" also includes, but is not limited to, molecules comprising carbon, hydrogen and oxygen that do not fall within the traditional definition of a saccharide—i.e., an aldehyde or ketone derivative of a straight chain polyhydroxyl alcohol, containing at least three carbon atoms. Thus, for example, a carbohydrate may contain fewer than three carbon atoms. As used herein, the term "lipid" is used it is in the art, i.e., substances of biological origin that are made up primarily or exclusively of nonpolar chemical groups such that they are readily soluble in most organic solvents, but only sparingly soluble in aqueous solvents. Examples of lipids include, but are not limited to, fatty acids, triacylglycerols, glycerophospholipids, sphingolipids, cholesterol, steroids and derivatives thereof. For example, "lipids" include but are not limited to, the ceramides, which are derivatives of sphingolipids and derivatives of ceramides, such as sphingomyelins, cerebrosides and gangliosides. "Lipids" also include, but are not limited to, the common classes of glycerophospholipds (or phospholipids), such as phosphatidic acid, phosphatidylethanolamine, phosphatidylcholine, phosphatidylserine, phosphatidylinositol, phosphatidylglycerol and the like. As used herein, a "drug" can be a known drug or a drug candidate, whose activity or effects on a particular cell type are not yet known. A "drug metabolite" is any of the by-products or the breakdown products of a drug that is changed chemically into another compound or compounds. As used herein, "small organic molecule" includes, but is not limited to, an organic molecule or compound that does not fit precisely into other classifications highlighted herein.

The engineered proteins of the current invention can be used to assess or measure the concentrations of more than one target analyte. As used herein, concentration is used as it is in the art. The concentration may be expressed as a qualitative value, or more likely as a quantitative value. As used herein, the quantification of the analytes can be a relative or absolute quantity. Of course, the quantity (concentration) of any of the analytes may be equal to zero, indicating the absence of the particular analyte sought. The quantity may simply be the measured signal, e.g., fluorescence, without any additional measurements or manipulations. Alternatively, the quantity may be expressed as a difference, percentage or ratio of the measured value of the particular analyte to a measured value of another compound including, but not limited to, a standard or another analyte. The difference may be negative, indicating a decrease in the amount of measured analyte(s). The quantities may also be expressed as a difference or ratio of the analyte(s) to itself, measured at a different point in time. The quantities of analytes may be determined directly from a generated signal, or the generated signal may be used in an algorithm, with the algorithm designed to correlate the value of the generated signals to the quantity of analyte(s) in the sample.

The engineered proteins of the current invention are designed to possess capabilities of continuously measuring the concentrations an analyte. As used herein, the term "continuously," in conjunction with the measuring of an analyte, is used to mean the engineered protein either generates or is capable of generating a detectable signal at any time during the life span of the engineered protein. The detectable signal may be constant in that the engineered protein is always generating a signal, even if the signal is not detected. Alternatively, the engineered protein may be used episodically, such that a detectable signal may be generated, and detected, at any desired time.

While not a requirement of the present invention, the engineered proteins are particularly useful in an in vivo setting for measuring target analytes as they occur or appear in a host organism or tissue or cell. As such, the target analytes need not be labeled. Of course, unlabeled target analytes may also be measured in an in vitro or in situ setting as well. In another embodiment, the target analytes may be labeled. Labeled target analytes can be measured in an in vivo, in vitro or in situ setting.

The samples would require minimal processing, thus the engineered proteins allow high-throughput measurements in complex samples using an appropriate plate fluorometer (e.g. TECAN M1000). This type of analysis can be used to measure the analyte content in different tissues, different individuals or different populations of, for example, crop plants experiencing drought. Purification of bulk amounts of engineered proteins can be achieved after expression in *Pichia pastoris*, using pPinkFLIP vectors and a protease deficient strain of *Pichia*.

The examples herein are provided for illustrative purposed and are not intended to limit the scope of the invention in any way.

EXAMPLES

Example 1

Generation of Multiple Engineered Ammonium Transporter Proteins

Crystal structures of AMTs from *Escherichia coli* and *Archaeoglobus fulgidus* did not reveal obvious conformational changes, leading to the proposition that AMTs are rigid gas channels. Other studies, however, challenged this hypothesis by demonstrating an allosteric feedback inhibition of transport activity by phosphorylation of residues in the trans-activating cytosolic C-terminus. Thus the mode of operation of these transporters was entirely unclear and unsettled.

Figure 4A:
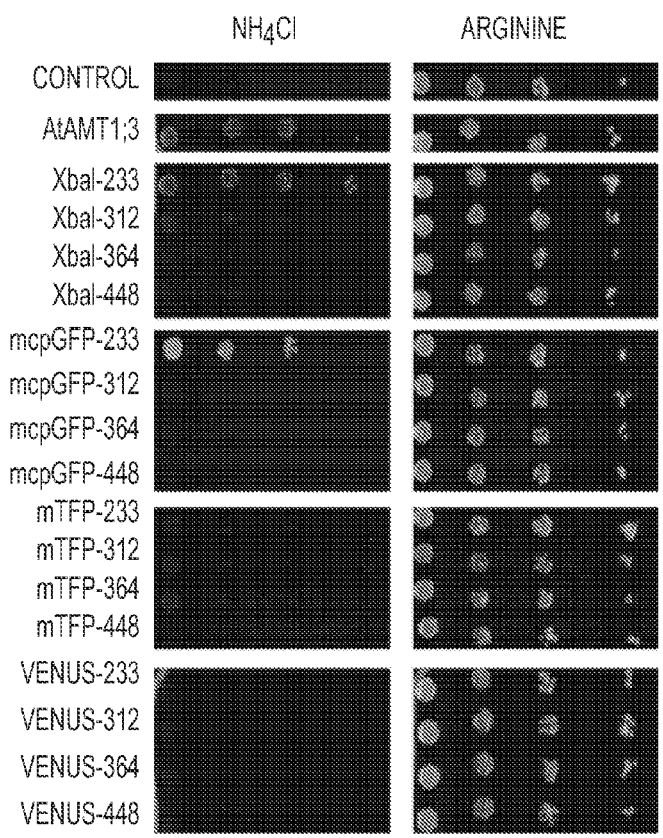
FIG. 4 depicts the characterization of constructs with FP insertions. (a) The functionality of the transporters was measured as growth of the yeast Δmep1,2,3 mutant transformed with AMT-FP fusions and grown on solid media containing 2 mM $NH_4Cl$ or 1 mM arginine (growth control) as the sole nitrogen source for three days. Numbers indicate the position in AtAMT1;3 preceding the insertion site. Control: empty vector. (b) Fluorescence emission spectra of the fusion construct AMT1;3-mcpGFP-233 expressed in yeast.
Figure 4B:
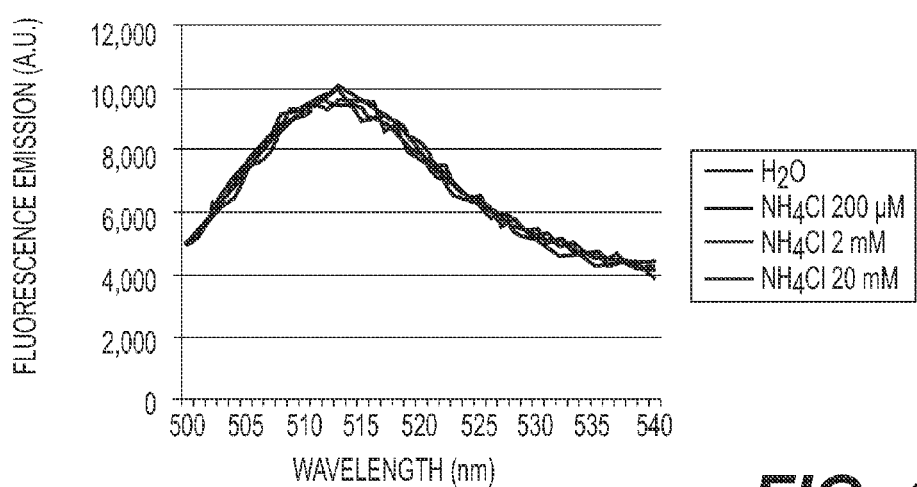

To engineer a transporter that reports substrate-dependent changes in conformation, conformation-sensitive fluorescent proteins (FP) was inserted into *Arabidopsis thaliana* ammonium transporter (AMT1;3) (FIGS. 1 and 4). Monomeric teal fluorescent protein (mTFP), yellow fluorescent protein (YFP) Venus or a modified circularly permuted GFP (mcpGFP) were inserted into intracellular loops of AMT1;3. The constructs were inserted in the yeast expression vector pDRf1-GW, containing the fl replication origin, GATEWAY™ cassette, PMA1 promoter fragment, ADH terminator, and the URA cassette for selection in yeast. The XbaI restriction site (tctaga) was inserted in different positions of AtAMT1;3 (after amino acids 233, 312, 364 and 448) via Kunkel mutagenesis.

mcpGFP was generated by amplifying the domains of EGFP corresponding to amino acids 150-239 and 1-144 with the primers:

```
EGFP-150-for:
                                        (SEQ ID NO: 1)
aacgtctatatcatggcc EGFP-239-rev:
                                        (SEQ ID NO: 2)
ttttt accggt accacc cttgtacagctcgtcca EGFP-1-for:
                                        (SEQ ID NO: 3)
ttttt accggt ggatct atggtgagcaagggcg EGFP-144-rev:
                                        (SEQ ID NO: 4)
agttgtactccagcttgtgc
```

Primers EGFP-239-rev and EGFP-1-for contained an AgeI restriction site (in bold) and additional nucleotides coding for Gly-Gly and Gly-Ser, respectively (underlined). The two amplified bands were gel-purified by a commercial kit (Machery-Nagel), digested by AgeI (New England Biolabs) and ligated by T4 DNA ligase (New England Biolabs). The resulting cpGFP, where the domains 150-239 and 1-144 were connected by the linker coding GGTGGS (SEQ ID NO: 32), was cloned into a pGEM-Teasy (Promega). The additional internal mutations M66K, V76A, S88G, D93Y, T116V, A119K, V251I, which were known to improve stability of cpGFP, were introduced by Kunkel mutagenesis.

Finally, the mcpGFP was amplified with the primers below and contained the XbaI restriction site (in bold):

```
cpGFP-for:
                                        (SEQ ID NO: 5)
ttttt tctaga aacgtctatatcatggcc cpGFP-rev:
                                        (SEQ ID NO: 6)
ttttt tctaga agttgtactccagcttgtgc
```

Similarly, mTFP and Venus were amplified with primers containing the XbaI site:

```
mTFP-for:
                                        (SEQ ID NO: 7)
ttttt tctaga atggtgagcaagggcgagg mTFP-rev:
                                        (SEQ ID NO: 8)
ttttt tctaga cttgtacagctcgtccatg Venus-for:
                                        (SEQ ID NO: 9)
ttttt tctaga aagggcgaggagctgttca Venus-rev:
                                        (SEQ ID NO: 10)
ttttt tctaga cttgtacagctcgtccatg
```

The purified mcpGFP, mTFP and Venus encoding fragments were digested by XbaI (New England Biolabs) and ligated into digested pDRf1-GW vectors containing AtAMT1;3, to generate the fusion constructs AtAMT1;3-mcpGFP, AtAMT1;3-TFP and AtAMT1;3-Venus in positions 233, 312, 364 and 448 (FIG. 4).

Figure 6A:
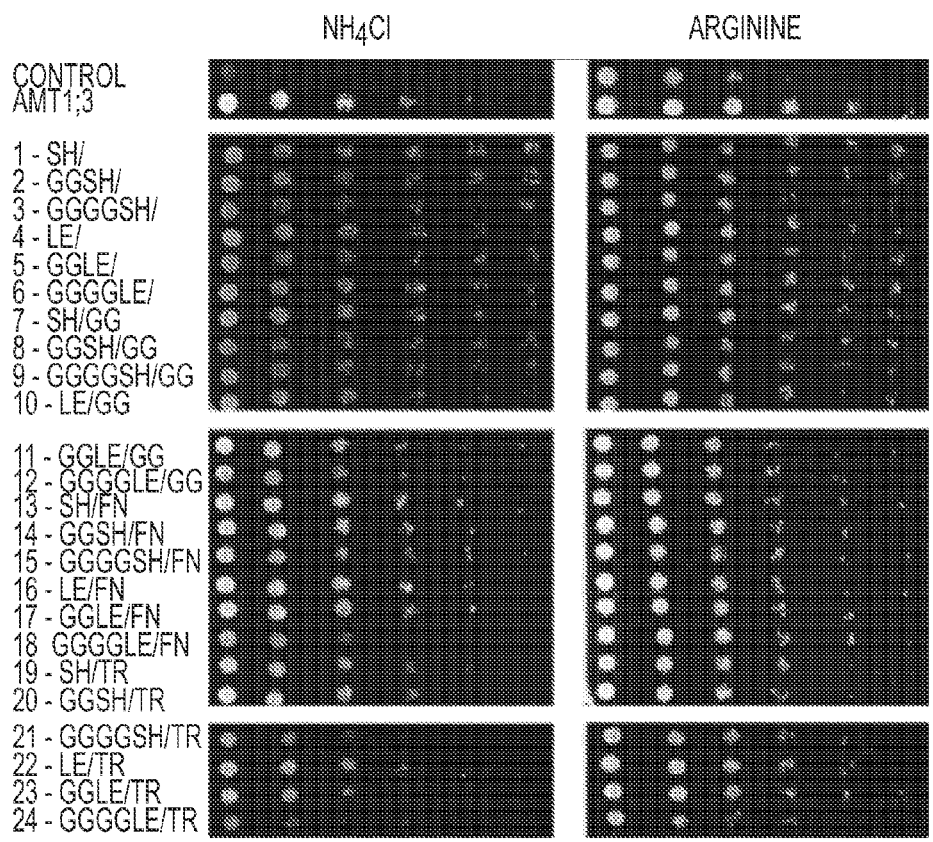
FIG. 6 depicts a screen of linker variants for identifying a AMT1;3-mcpGFP sensor. To create an AMT-mcpGFP fusion that responded to addition of ammonium with a fluorescence change, the composition and length of the peptide linker was varied. (a) Growth of the yeast Δmep1,2,3 mutant transformed with fusion variants on solid media containing 2 mM $NH_4Cl$ or 1 mM arginine (growth control) as the sole nitrogen source for three days. All variants retained transport activity. Composition of linkers connecting AtAMT1;3 and mcpGFP are indicated. Linkers at the N- and C-termini of mcpGFP are indicated in letter code and separated by a slash. In the cases of variants 1-6, no linkers were inserted between the C-terminal sequence of mcpGFP and the second part of AtAMT1;3. Control, empty vector. (b) Fluorescence intensity before addition of ammonium and fluorescence intensity change after addition of 1 mM $NH_4Cl$ for the 24 linker variants (mean±s.d.; n=3). Most variants showed at least some change in intensity, but variant 16, carrying LE/FN as linkers, named AmTrac, showed the highest change in fluorescence intensity.
Figure 6B:
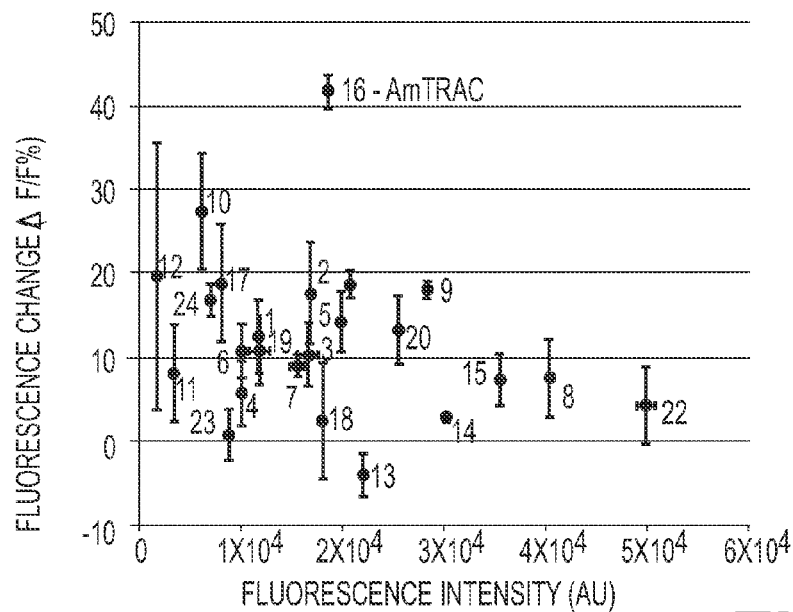

To vary the linker regions between mcpGFP and AtAMT1;3 in position 233 (FIG. 6), homologous recombination was employed in the yeast between two DNA fragments sharing sequence homology. The yeast were co-transformed with the pDR-AtAMT1;3 opened at position 233 by XbaI digestion, and the mcpGFP fragments amplified by PCR with the primers:

cpGFP-for-SH:
(SEQ ID NO: 11)
ggtcctcgtcgtggtcggttcgagaaa tctcat
aacgtctatatcaag cGFP-for-GGSH:
(SEQ ID NO: 12)
ggtcctcgtcgtggtcggttcgagaaa ggtggttctcat
aacgtctatatcaag cGFP-for-GGGGSH:
(SEQ ID NO: 13)
ggtcctcgtcgtggtcggttcgagaaa ggtggtggtggttctcat
aacgtctatatcaag cGFP-for-LE:
(SEQ ID NO: 14)
ggtcctcgtcgtggtcggttcgagaaa ctcgag
aacgtctatatcaag cGFP-for-GGLE:
(SEQ ID NO: 15)
ggtcctcgtcgtggtcggttcgagaaa ggtggtctcgag
aacgtctatatcaag cGFP-for-GGGGLE:
(SEQ ID NO: 16)
ggtcctcgtcgtggtcggttcgagaaa ggtggtggtggtctcgag
aacgtctatatcaag cGFP-rev:
(SEQ ID NO: 17)
gtggccgcgcagagcaatagcgcgaccacc
gttgtactccagcttg cGFP-rev-GG:
(SEQ ID NO: 18)
gtggccgcgcagagcaatagcgcgaccacc tcctcc
gttgtactccagcttg cGFP-rev-FN:
(SEQ ID NO: 19)
gtggccgcgcagagcaatagcgcgaccacc attaaa
gttgtactccagcttg cGFP-rev-TR:
(SEQ ID NO: 20)
gtggccgcgcagagcaatagcgcgaccacc tcttgt
gttgtactccagcttg The amplification products contained the mcpGFP flanked by the variable linker sequences (underlined) and about 30 bp homologous to the region around the insertion point 233 of AtAMT1;3 (in bold). The transformed yeast contained the pDR-AMT-mcpGFP vectors resulting from insertion of the ~800 bp mcpGFPs with linkers into the vector backbone, as confirmed by DNA sequencing.

Figure 14A:
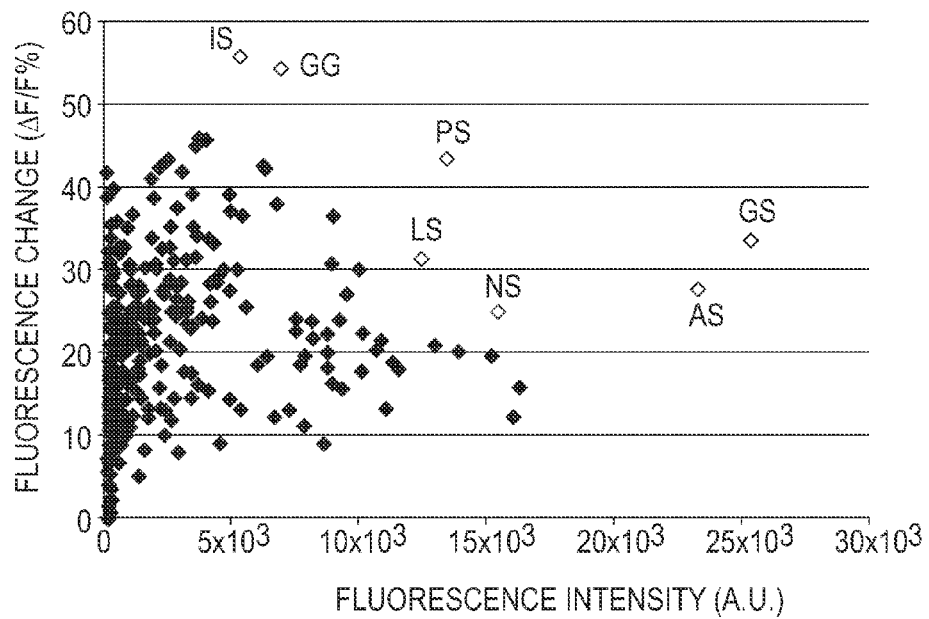
FIG. 14 depicts a screen for sensor variants. (a) Fluorescence intensity and fluorescence response of ~350 random variants of the C-terminal linker of mcpGFP to addition of 1 mM $NH_4Cl$. The brightest and most responsive variants (open squares) were sequenced and composition of the linker is reported. (b) Fluorescence intensity and fluorescence response after addition of 1 mM $NH_4Cl$, normalized to values of AmTrac (100%) of yeast expressing the best variants identified in (A) (mean±s.d.; n=3).
Figure 14B:
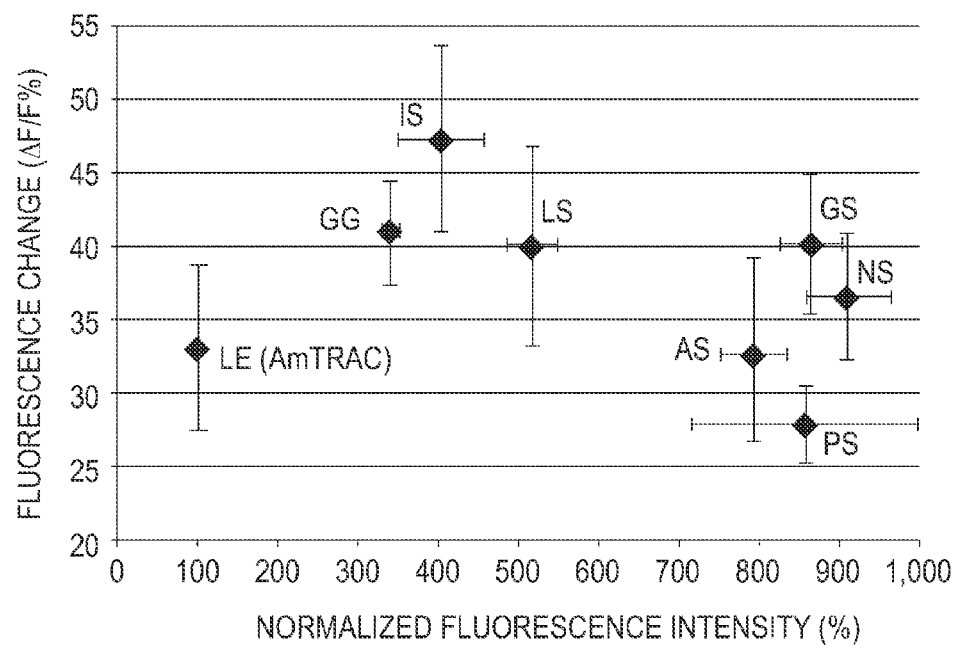

Homologous recombination was also used to generate variants of the linker preceding mcpGFP (FIG. 14). For this case, mcpGFP was amplified with the primers below (where N indicates any nucleotide).

cGFP-for-deg:
(SEQ ID NO: 21)
ggtcctcgtcgtggtcggttcgagaaa NNNNNN
aacgtctatatcaag cGFP-rev-FN:
(SEQ ID NO: 22)
gtggccgcgcagagcaatagcgcgaccacc attaaa
gttgtactccagcttg Homologous recombination was also used to insert the mcpGFP in different positions along L5-6 (FIG. 9) and to generate deletions in the loop. In this case, the 30 bp-long regions of the primers that overlapped the AtAMT1;3 sequence flanked the different insertion points (228 to 236) and contained the appropriate deletions.

Figures 2A, 2B:
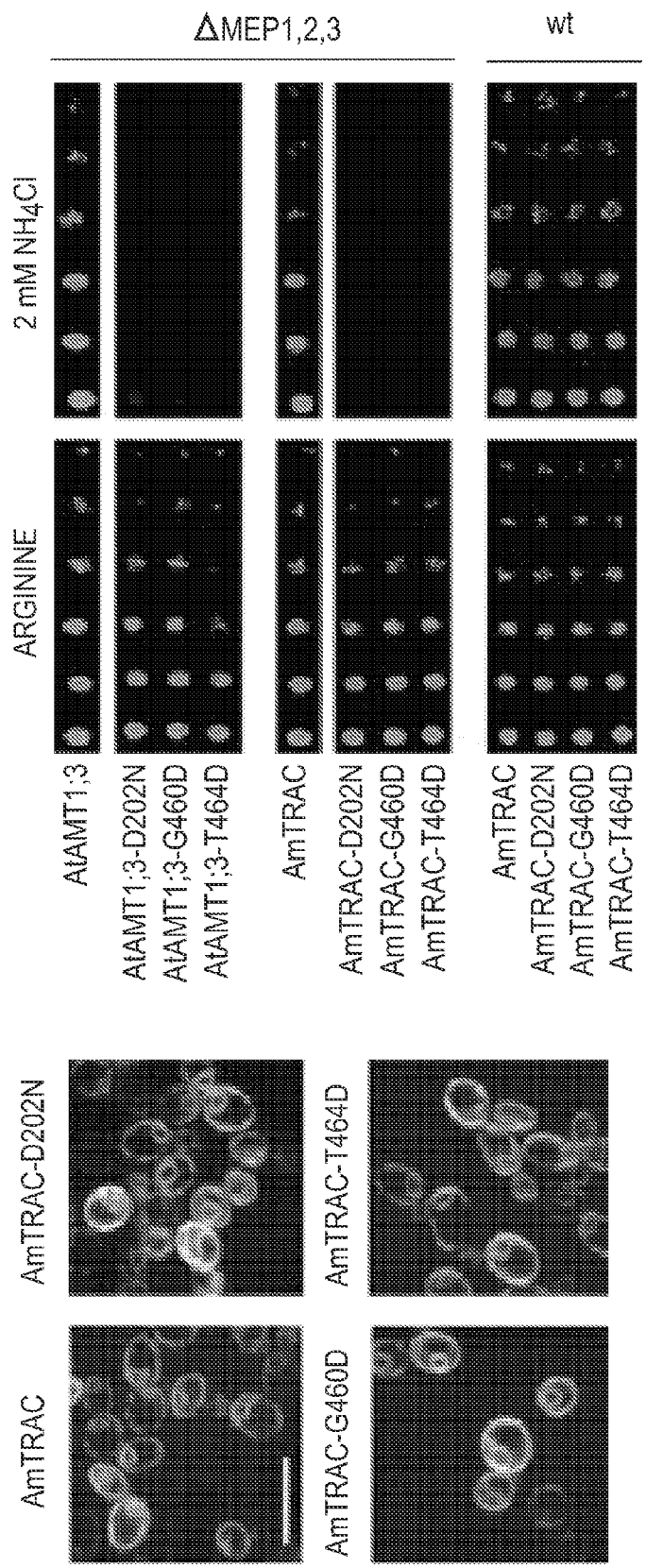
FIG. 2 depicts AmTrac mutant analysis. (a) Confocal section of yeast expressing AmTrac or its inactive variants D202N, G460D or T464D. Bar=10 µm. (b) Growth of the Δmep1,2,3 or wt yeast expressing AmTrac or its inactive variants on solid media containing 2 mM $NH_4Cl$ or 1 mM arginine (growth control) as sole nitrogen source for 3 days. Endogenous MEPs in wt strain are not affected by expression of mutant variants. (c) Fluorescence response of Δmep1,2,3 and wt yeast expressing AmTrac or its inactive variants to 1 mM $NH_4Cl$ (mean±s.d.; n=3). Only the yeast cells expressing AmTrac showed a response significantly different from control (SNK test: *$P<0.01$). (d) Growth complementation of Δmep1,2,3 expressing suppressor mutants grown on solid media containing the indicated concentrations of $NH_4Cl$ or 1 mM arginine. AmTrac-T464D-A141E expressing cells grow poorly at high ammonium concentrations. (e) Correlation between transport efficiency (growth in 2 mM $NH_4Cl$) and fluorescence change after addition of 1 mM $NH_4Cl$ of the suppressor mutants. Data are normalized by values of AmTrac (=100) (mean±s.d.; n=3). (f) Titration of the fluorescent response of AmTrac (circles) and of the high capacity variant AmTrac-100µ (squares). Data are normalized to water-treated controls (0) (mean±s.d.: n=3).
Figure 2C:
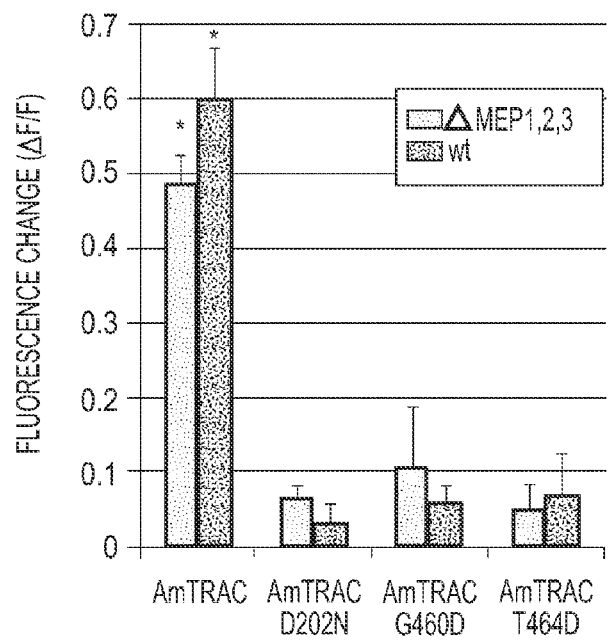
Figure 2D:
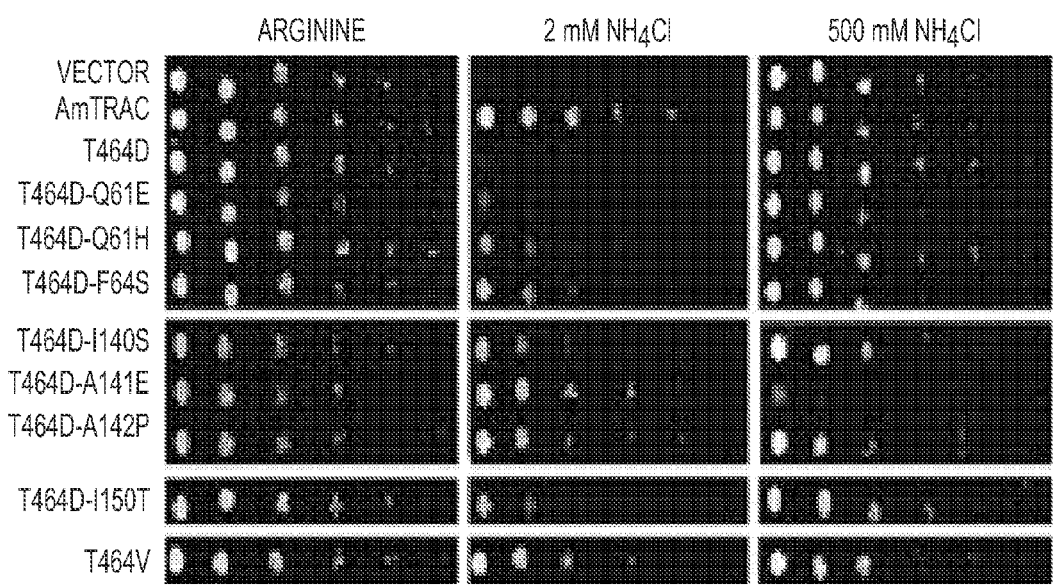
Figure 11A:
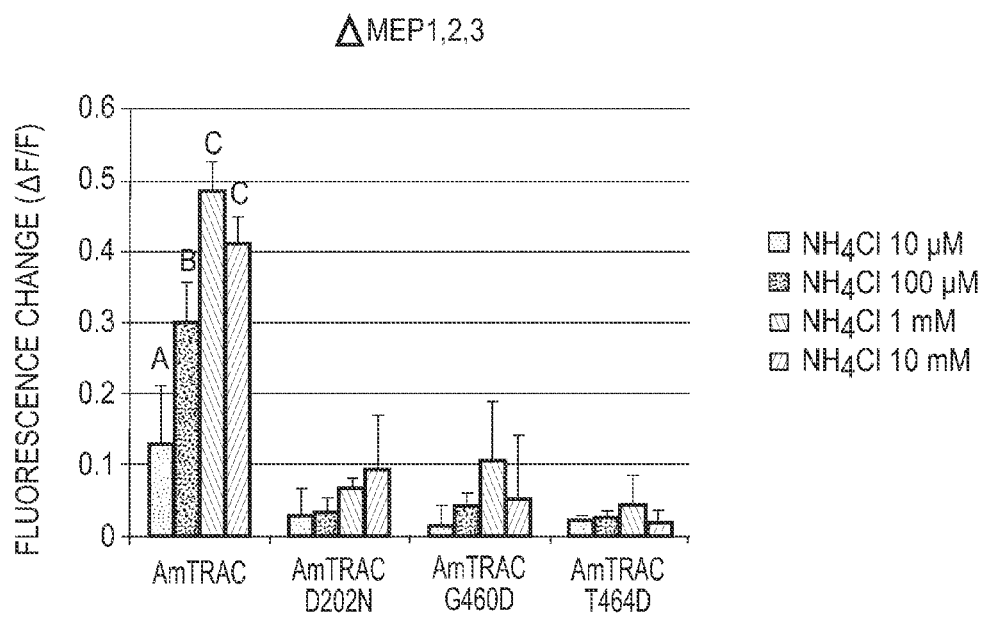
FIG. 11 depicts the fluorescence response of transport-deficient AmTrac mutants to increasing ammonium concentrations. Fluorescence response of Δmep1,2,3 (a) or wt (b) yeast expressing AmTrac or the transport-inactive variants D202N, G460D or T464D. Data were normalized to water-treated controls (0) (mean±s.d.; n=3). Only yeast cells expressing AmTrac showed significantly different responses (SNK test: P<0.01).
Figure 11B:
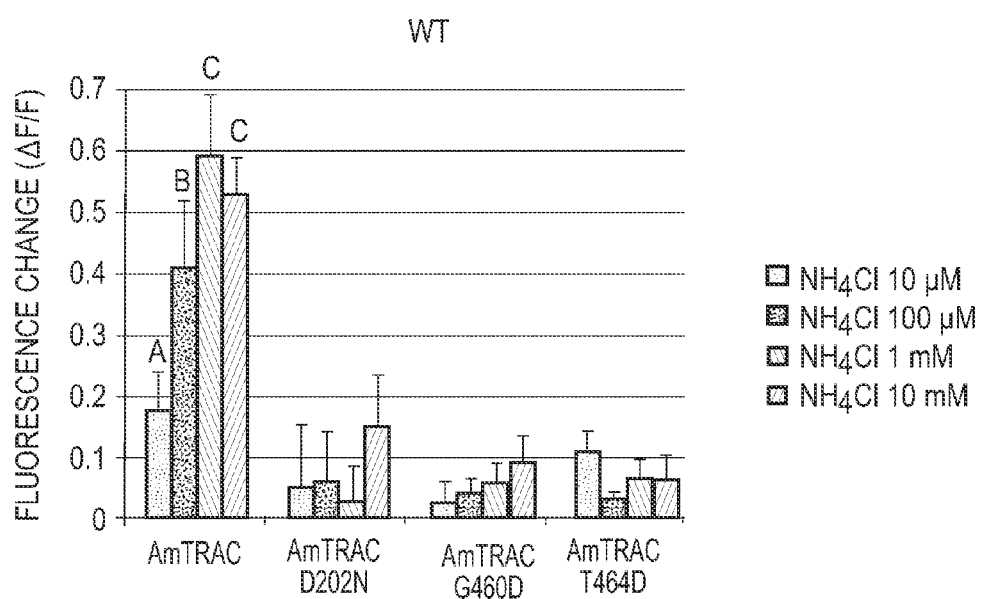

Point mutations for inactivation of AtAMT1;3 and AmTrac were generated by we used Kunkel mutagenesis (D202N, G460D, T464D; FIGS. 2 and 11).

Example 2

Functional Testing of the Engineered Ammonium Transporter Proteins

The functionality of the constructs was tested by complementation of ammonium uptake in a yeast mutant lacking endogenous ammonium transporters. Yeast strains 31019b [mep1Δ mep2Δ::LEU2 mep3Δ::KanMX2 ura3], a strain in which all three endogenous MEP ammonium transporter genes had been deleted, and its parental strain 23344c [ura3], were transformed using the lithium acetate method and selected on solid YNB (minimal yeast medium without nitrogen; Difco) supplemented with 3% glucose and 1 mM arginine. Single colonies were grown in 5 mL liquid YNB supplemented with 3% glucose and 0.1% proline under agitation (230 rpm) at 30° C. until $OD_{600nm}$ ~0.8. The liquid cultures were diluted $10^{-1}$, $10^{-2}$, $10^{-3}$, $10^{-4}$, $10^{-5}$ and $10^{-6}$ in water and 5 μL of each dilution were spotted on solid YNB medium buffered with 50 mM MES/Tris, pH 5.2 and supplemented with 3% glucose and either $NH_4Cl$, $(NH_4)_2SO_4$ or 1 mM arginine as the sole nitrogen source.

After 3 d of incubation at 30° C., cell growth was documented by scanning the plate at 300 dpi in grayscale mode. For fluorimetric analyses, yeast cultures were washed twice in 50 mM MES buffer, pH 6.0, and resuspended to $OD_{600nm}$ ~0.5 in MES buffer supplemented with 5% glycerol to delay cell sedimentation. Fluorescence was measured by a fluorescence plate reader (Safire, Tecan), in bottom reading mode using a 7.5 nm bandwidth for both excitation and emission.

Figure 7:
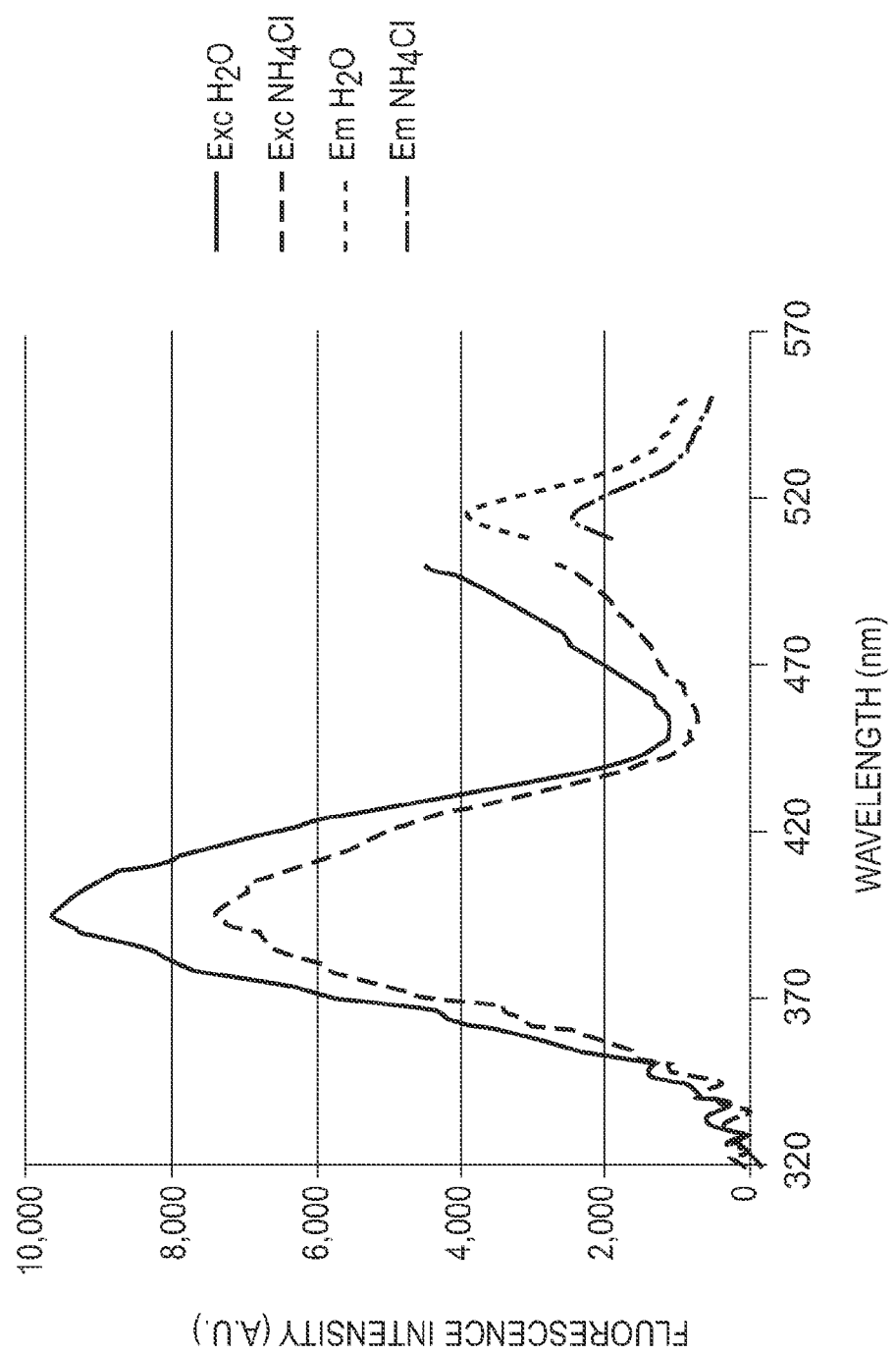
FIG. 7 depicts the fluorescence spectra of AmTrac (variant 16 from FIG. 6). Excitation spectra (left curves) were recorded at an emission wavelength of 520 nm. Emission spectra (right curves) were recorded with excitation of 488 nm. Data were background-subtracted using data from yeast cells carrying an empty vector. Exc=excitation scan, Em=emission scan. Note that ammonium treatment triggers a decrease in fluorescence.

Yeast cultures were washed twice in 50 mM MES buffer, pH 6.0, and resuspended to $OD_{600nm}$ ~0.5 in MES buffer supplemented with 5% glycerol to delay cell sedimentation. Fluorescence was measured by a fluorescence plate reader (Safire, Tecan), in bottom reading mode using a 7.5 nm bandwidth for both excitation and emission. To measure fluorescence response to substrate addition, 504 of substrate (dissolved in water as 500% stock solution) were added to 2004 of cells in a 96-well plate (Greiner). For the spectral recordings of AmTrac (FIGS. 4 and 7), excitation scans were performed at emission wavelength of 520 nm; emissions scans were recorded with excitation at 488 nm. In all other cases, fluorescence was measured as emission at 513 nm using excitation at 488 nm. Response data are presented as $(F_{water} - F_{treatment})/F_{treatment}$.

Figure 5:
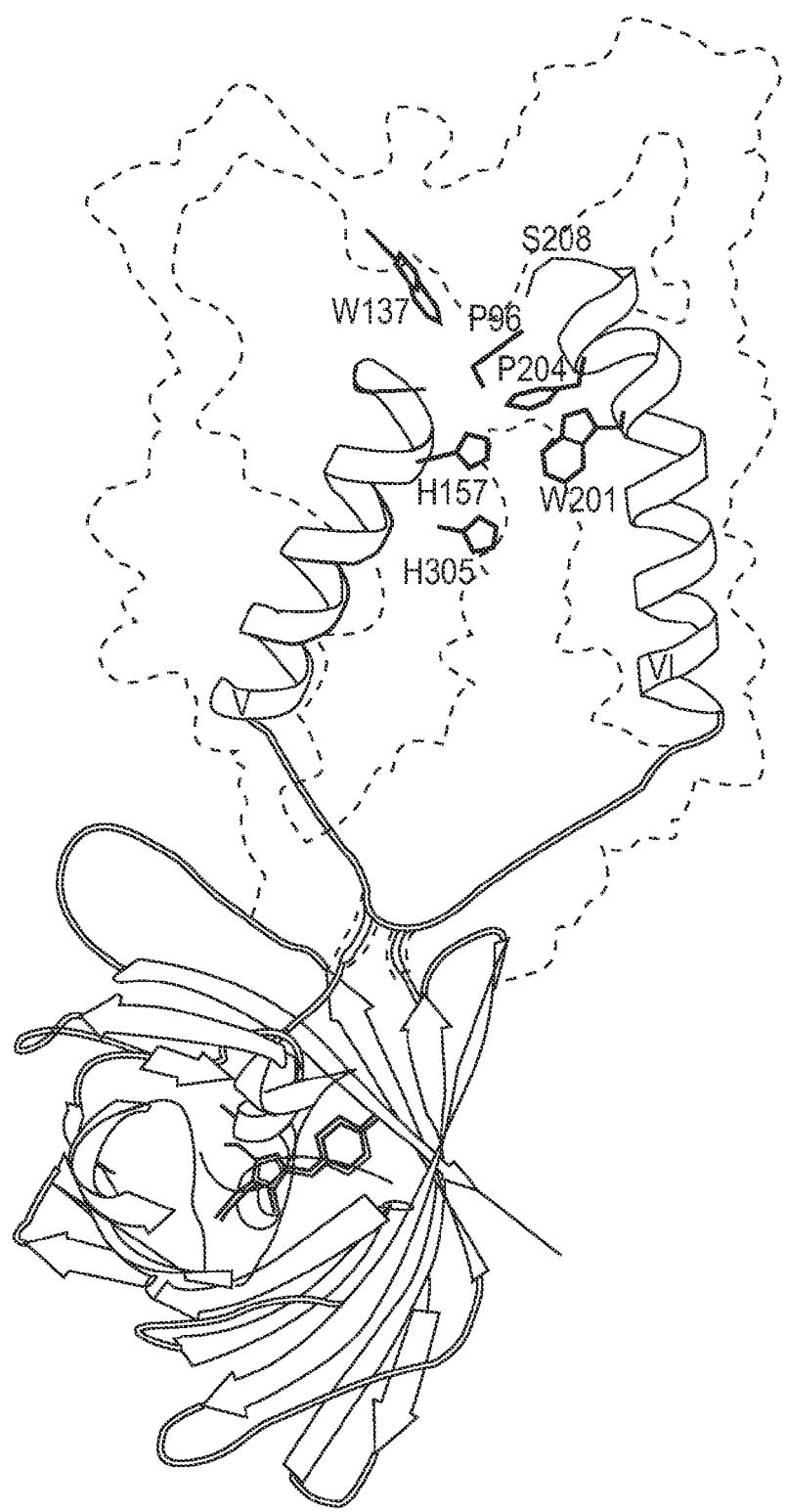
FIG. 5 depicts a model of the AtAMT1;3-mcpGFP fusion. mcpGFP (bottom portion) was fused to the integral membrane protein AtAMT1;3 in position 233 of the cytoplasmic L5-6 bridging TMH-V to TMH-VI. The connection point between the two proteins is shown as dashed line. Residues shown in sticks highlight the location of several residues relevant for transport function, in particular TMH-V-H157 from the twin-His (H157-H305) pair, TMH-VI-S208 (forming the ammonium selectivity and recruitment site together with W137), TMH-VI-P204 from the twin Phe-gate (F96-F204) that close the pore in all known structures. The peptide loop connecting TMH V-VI, L5-6 also connects the two pseudo-symmetric halves of the structural inverted repeat of the protein (TMH I-V and TMH VI-X).

AMT1;3 was extremely sensitive to any manipulation within the loops 7-8 and 9-10 or the cytosolic C-terminus (FIG. 4). However, modification of loop 5-6 (L5-6, position 233) by insertion of either two amino acid residues (encoded by the restriction site XbaI) or mcpGFP was tolerated (FIG. 4). The L5-6 is located between the two pseudo-symmetric halves, i.e., between the two structural inverted repeats, of the protein and connects two transmembrane helices (TMH-V and -VI) that contain residues postulated to be directly involved in recruitment, gating and substrate translocation (FIG. 5).

Figure 10:
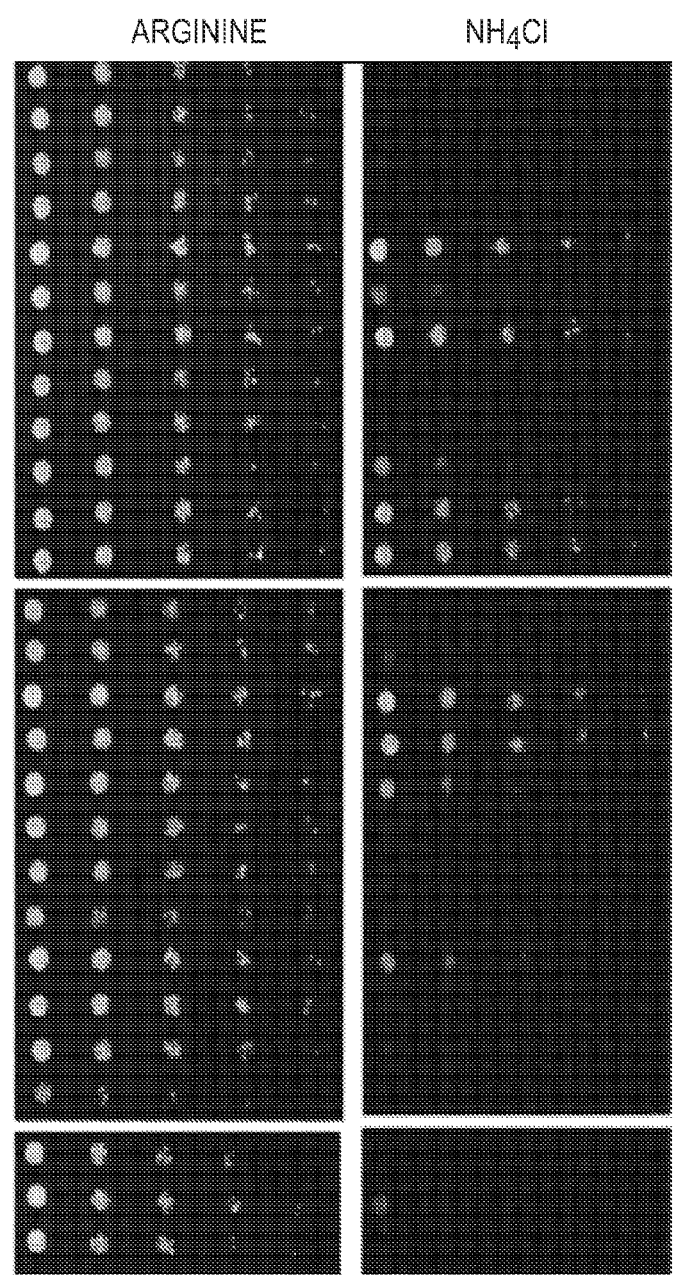
FIG. 10 depicts the growth and response of AmTrac variants with deletions in L5-6. To probe whether the loop length was critical for transport activity and fluorescence response, incremental deletions of the peptide loop L5-6 were generated around the insertion point of mcpGFP. Growth was analyzed as described in FIG. 9. Numbers in the left column indicate the position of the insertion in AtAMT1;3; two numbers indicate residues preceding and following the mcpGFP insertion. Right column indicates whether the corresponding variant responded to addition of 1 mM $NH_4Cl$ with a fluorescence change. The original AmTrac is highlighted in bold. Note that deletions >4 residues abolished transport activity and deletions >3 impaired the fluorescence response.

In initial tests, addition of ammonium to yeast cells expressing the AMT-mcpGFP fusion did not lead to detectable changes in fluorescence intensity (FI; FIG. 4). Providing a linker connecting AMT and mcpGFP permitted detectable changes in FI. One specific linker variant demonstrated a strong response to 1 mM $NH_4Cl$ (40% FI change) (FIGS. 1, 6, 7 and 8). The position of the mcpGFP insertion in L5-6 and the loop-linker length affected changes in FI (FIGS. 9 and 10), although the placement of the mcpGFP at several places in the L5-6 loop were effective. Importantly, all the variants that responded to ammonium with a FI change were functional transporters, indicating that the various constructs were able to accurately report transport activity (FIGS. 9 and 10).

To further corroborate the correlation between transport and ammonium-induced FI change, mutations (D202N, G460D, T464D) known to inactivate AMT1 transporters were introduced into AmTrac. Confocal sections of yeast cells expressing the sensors (FIG. 2) were acquired on an inverted confocal laser scanning microscope (SP5, Leica). To record fluorescence intensities in single cells over time, yeast cells were trapped as a single cell layer in a microfluidic perfusion system (Y04C plate, Onyx, Cellasic) and perfused with either 50 mM MES buffer, pH 6.0, or buffer supplemented with $NH_4Cl$. The setup was imaged at a spinning disk confocal microscope (Yokogawa CSU-X1; Leica DM16000) equipped with a motorized stage (ASI). Fluorescence was excited by a solid state laser at 488 nm; emission was detected using a 525/50 nm filter set (Semrock) and an electron multiplying charge coupled device (EMCCD) camera (Evolve, Photometrics). Measurements were taken every 2 min, with 100 ms exposure time using Slidebook 5.0 image acquisition software (Intelligent Imaging Innovations). To account for lateral shift during imaging, the image stacks were post-registered using the StackReg plugin for ImagaJ. Fluorescence pixel intensity was quantified using Fiji software; single cells were selected and analyzed with the help of the ROI manager tool. Kymograph analysis was performed using the MultipleKymograph plugin for ImageJ (Rietdorf and Seitz) by measuring pixel intensities over time along a 3 pixel wide line.

While these mutations did not affect plasma membrane localization of one of the constructs, named "AmTrac" (FIG. 2), both transport activity and fluorescence response were abolished (FIGS. 2 and 11), demonstrating that transport activity was necessary for the FI response of AmTrac.

Figures 12A, 12B:
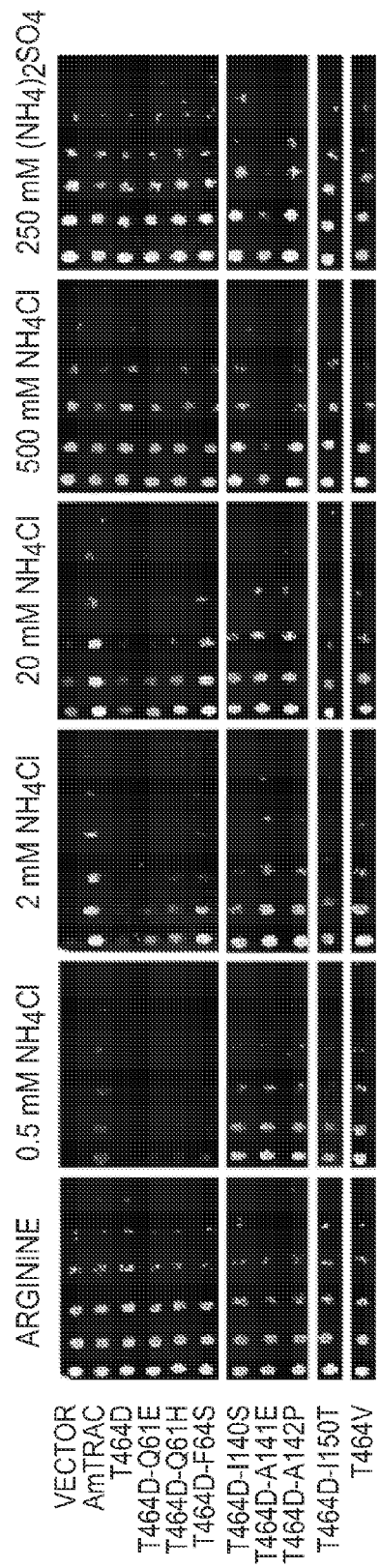
FIG. 12 depicts the reconstitution of the fluorescent response in cis-suppressor mutants of the transport-inactive AmTrac-T464D mutant. (a) Frequency of the occurrence of individual cis-suppressors of the T464D-inactivating mutation in the multicopy screen. A total of 56 colonies were retrieved. Almost half of them carried the A141E mutation. Three suppressors had a pseudo-reversion mutation: D464V. (b) Growth was analyzed as described in FIG. 9, with varying concentrations of $NH_4Cl$, $(NH_4)_2SO_4$ (as anion control) or 1 mM arginine. The yeast expressing AmTrac-T464D-A141E grew poorly at high concentrations of ammonium, suggesting high capacity transport activity leading to ammonium toxicity. (c) Fluorescence response of selected suppressors to addition of the indicated concentrations of $NH_4Cl$. Data were normalized to water-treated controls (0) (mean±s.d.; n=3).
Figure 12C:
Figure 13C:
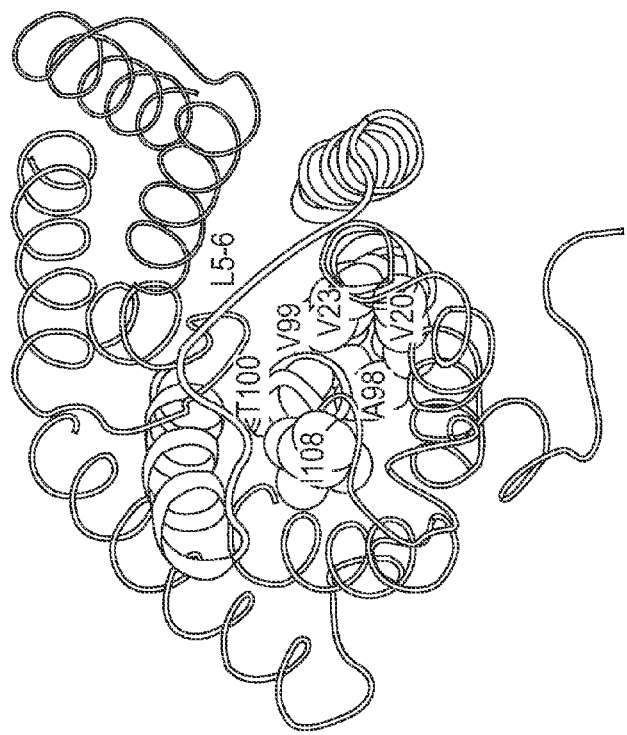
FIG. 13 depicts the position of suppressor mutations in AMTs. (a) Sequence alignment between AtAMT1;3 from *Arabidopsis* and AfAmt-1 from *A. fulgidus*. The residues belonging to TMH domains of the two halves of the structural inverted repeat of AfAMT1 are shown as underlined and speckled, respectively. The corresponding residues identified in the suppressor screen of AmTrac-T464D are indicated in both sequences as bold residues. (b) Lateral view and (c) cytoplasmic side view of AfAMT1 according to the crystal structure. The corresponding residues in AfAMT1 that suppress the T464D mutation in AmTrac are indicated by spheres. The connecting L5-6 is peptide loop labeled.
Figure 13B:

Previous studies have shown that the C-terminus of AMT1 acts as a trans-activation domain in the trimeric AMT1 complex. Mutations in the cytosolic C-terminus block AMT1 activity, which can be restored by suppressor mutations either in the cytosolic loops or in the pore region. A saturating multicopy suppressor screen with the inactive mutant AmTrac-T464D identified eight gain-of-function mutations (FIGS. 2, 12 and 13), seven in the pore region and one pseudo-reversion, D464V. The extent to which the suppressors were able to restore transport activity, as measured by growth, correlated highly with the FI response ($R^2$=0.72) (FIG. 2), giving direct proof of the strict link between transport activity and FI response.

Figure 15:
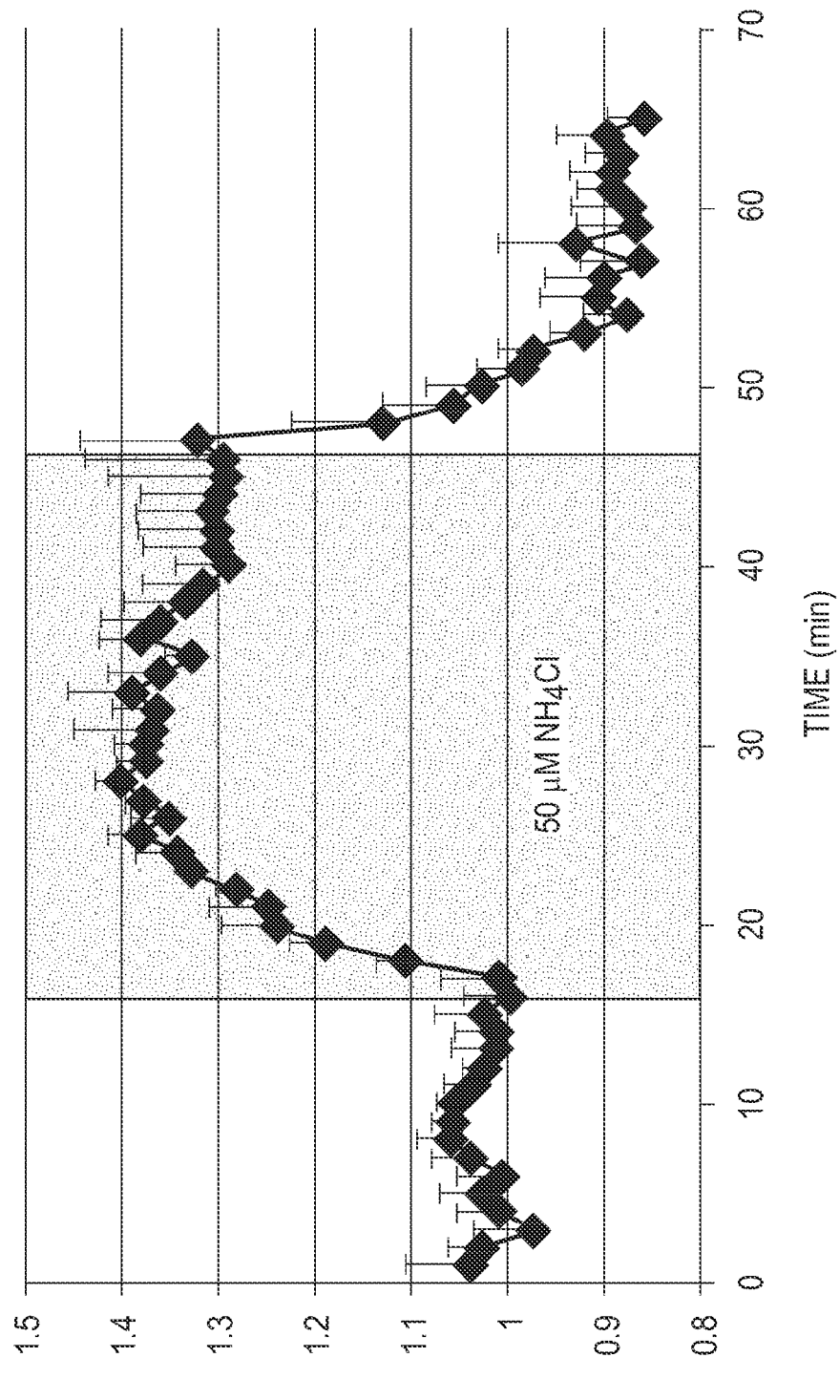
FIG. 15 depicts the single cell responsiveness of AmTrac-LS. Individual cells trapped in a microfluidic plate were perfused with 50 mM MES buffer pH 6.0, or a square pulse of 50 μM NH$_4$Cl in buffer (framed region). Data were normalized to the initial value (mean±s.d.; n=3).

To test the reversibility of the sensor response, the FI of single cells in microfluidic chambers was analyzed after withdrawal of ammonium. AmTrac responses were detectable in single cells, were concentration-dependent, and were readily reversible, demonstrating that AmTrac-LS can be used in vivo to measure transport of ammonium and to observe conformational change kinetics of the chimeric transporter in response to substrate availability (FIG. 1). To create sensors with enhanced SNR, residues were randomly substituted into the two-amino acid linker directly preceding mcpGFP. Mutant versions of the AmTrac that maintained transport activity were selected, and each showed both high FI and high ammonium-induced FI response. Interestingly, the majority of the brightest variants carried a Ser residue instead of a Glu in the position immediately preceding the mcpGFP insertion (FIG. 14). AmTrac-LS, a sensor with a Leu-Ser linker, was as responsive to ammonium as AmTrac (~40% FI change), yet it was 517% brighter (FIG. 14). AmTrac-LS responses were detectable in single cells, were concentration-dependent, and were readily reversible, demonstrating that AmTrac-LS can be used in vivo to measure transport of ammonium and to observe conformational change kinetics of the chimeric transporter in response to substrate availability (FIG. 15).

The fluorescence response of AmTrac transporter demonstrates that AMT1;3 undergoes conformational changes during the transport cycle. Interestingly, the pseudo-symmetry of AMT with an inverted repeat of five TMH is similar to that of the LeuT transporter. LeuT carries a substrate-binding site at the interface of the two repeats and undergoes a transport cycle involving multiple states. Similarly, the transport pore of the AMTs is located between the two pseudo-symmetric halves (or structural inverted repeats), with TMH-V and -VI (connected by L5-6) carrying key residues for ammonium translocation.

Figure 16:
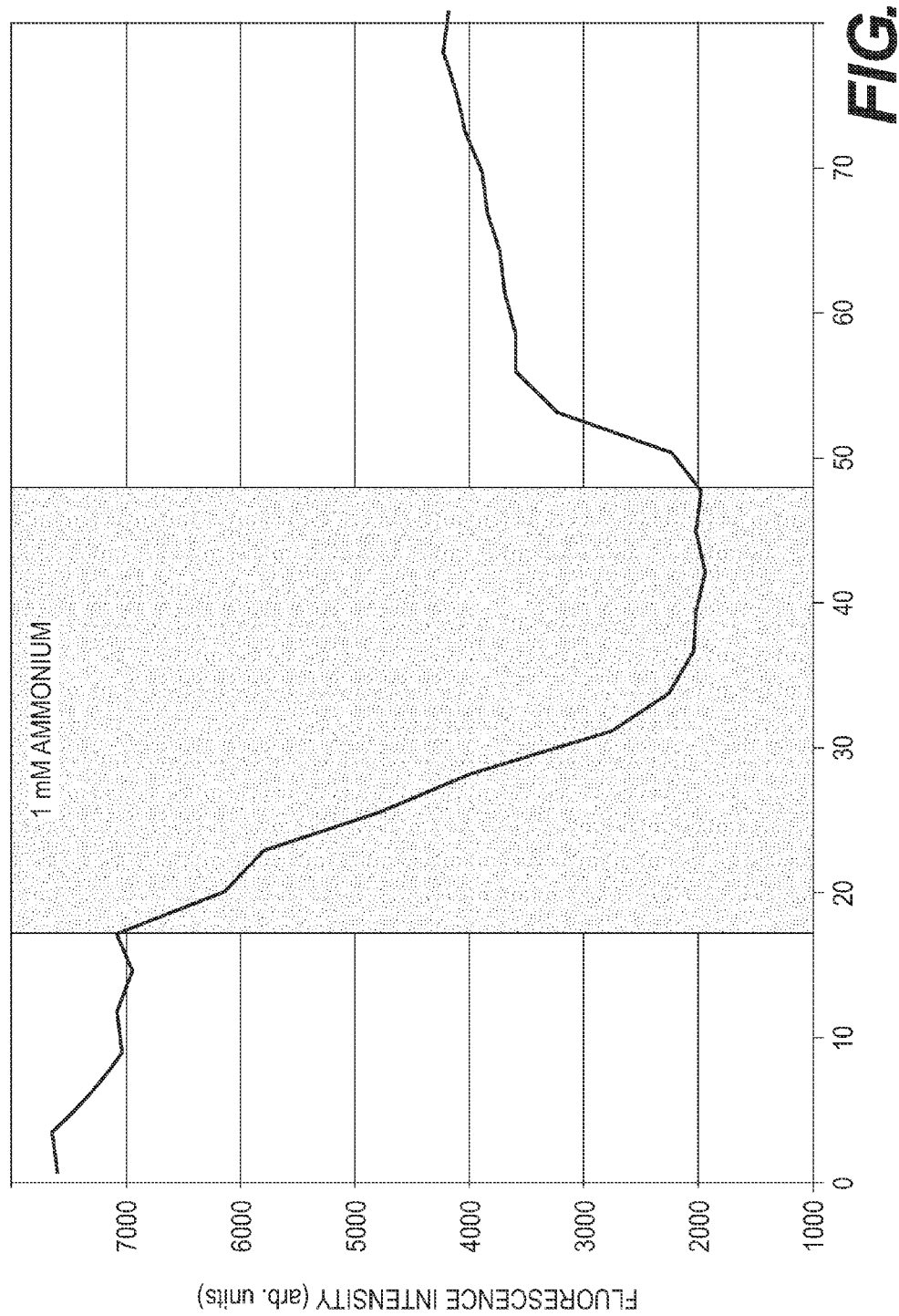
FIG. 16 depicts the responsiveness of AmTrac in root hairs of *Arabidopsis*. Seedlings grown in a microfluidic perfusion system (RootChip) were perfused with 50 mM MES buffer pH 6.0, or a square pulse of 1 mM NH$_4$Cl in buffer.

To test the functionality of AmTrac in systems other than yeast, AmTrac was expressed in *Arabidopsis* plants stably transformed via Agrobacterium by the method of floral dip, by using the vector pEARLEY100 (Earley et al. 2006). AmTrac was expressed under control of the strong promoter 35S. Seeds of heterozygous *Arabidopsis* were surface-sterilized and germinated in growth medium deprived of ammonium in 16 h-8 h light-dark conditions. After 5 days, seedlings were transferred in the microfluidic perfusion system Root-Chip and grown in liquid medium deprived of ammonium for additional 24 h. Roots and root hair from the seedling were then analyzed by inverted confocal microscopy (Yokogawa CSU-X1) and roots were perfused with 50 mM MES buffer or a square pulse of 1 mM ammonium chloride in buffer for 30 minutes. Fluorescence was excited by a solid state laser at 488 nm; emission was detected using a 525/50 nm filter set (Semrock) and an electron multiplying charge coupled device (EMCCD) camera (Evolve, Photometrics). FIG. 16 shows that the engineered proteins were functional in *Arabidopsis* root hairs. Fluorescence pixel intensity from single root hairs was quantified using Fiji software.

To show that the strategy of creating sensors by inserting fluorophores in transmembrane proteins is not limited to AtAMT1;3, the yeast MEP2 was also used as scaffold for creating a new sensor (MEPtrac). MEP2 is only 44% identical to AMT1;3, demonstrating that the invention is not limited by the amino acid sequence of the transporters. Notably, MepTrac was constructed in a single step based on the fluorophore insertion point determined in AMT as well as using the optimized linkers developed for AmTrac. Structural and phylogenetic studies have shown that members of the AMT/MEP/RH (AMT/MEP/RH superfamily (PFAM #PF00909) family have highly similar structures and that regulatory mechanisms are highly conserved. The one step conversion of MEP2, which is evolutionary very distant, but structurally highly conserved, into an engineered protein that is responsive to analyte movement through the sensor demonstrates that transporter proteins with a structural inverted repeat can be converted into sensors using the methods provided herein.

Figure 17A:
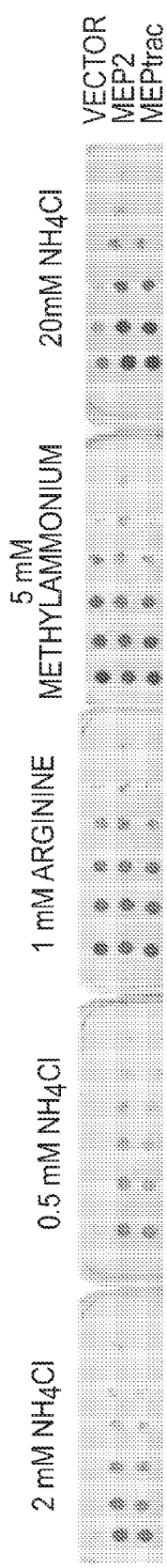
FIG. 17 depicts the characterization of an AmTrac version (named MEPtrac) employing the ammonium transporter MEP2 (methylammonium permease 2) from the yeast *Saccharomyces caerevisiae* instead of AMT1;3 of *Arabidopsis thaliana*. The mcpGFP was inserted in the middle of loop 5 of MEP2 (after amino acid 217) and connected by the linkers coding for amino acids LS (preceding mcpGFP) and FN (following mcpGFP). (a) Growth complementation of Δmep1,2,3 expressing suppressor mutants grown on solid media containing the indicated concentrations of NH$_4$Cl or 1 mM arginine or 5 mM methylammonium plus 0.1% proline. MEPtrac is able to complement growth on ammonium as well as the parent protein MEP2. (b) Fluorescence response of Δmep1,2,3 and wt yeast expressing MEPtrac to the indicated concentrations of NH$_4$Cl or NaCl (mean±s.d.; n=3).
Figure 17B:
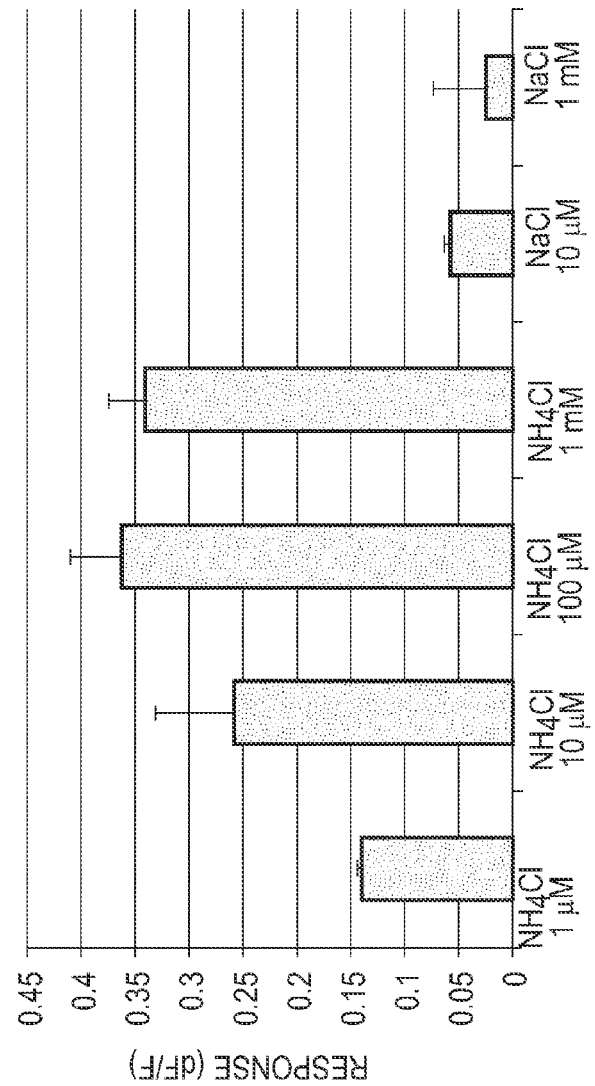

The mcpGFP was inserted in the middle of loop 5 of MEP2 (after amino acid 217) and connected by the linkers coding for amino acids LS (preceding mcpGFP) and FN (following mcpGFP) by using overlapping PCR cloning. The functionality of MEPtrac was tested by growth complementation of the of Δmep1,2,3 yeast strain on ammonium and the response of the sensor was tested by fluorimetric analysis after addition of different concentrations of ammonium chloride or sodium chloride as a control. See FIG. 17.

Figure 18A:
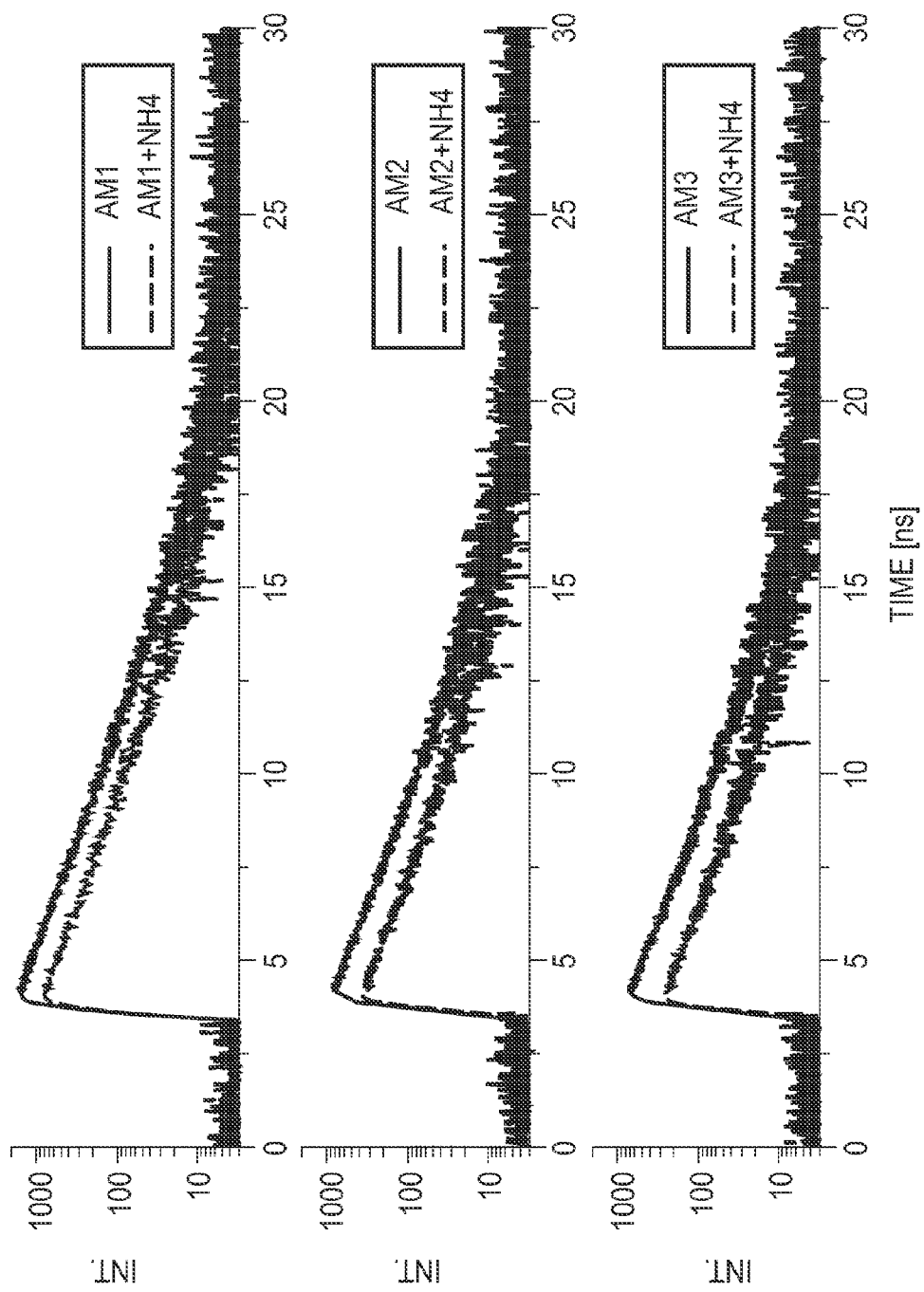
FIG. 18 depicts the time-resolved fluorescence lifetime measurements and analysis of intact yeast cells expressing three improved AmTrac variants, AmTrac-GS, AmTrac-LS and AmTrac-IS with and without addition of 1 mM NH$_4$Cl.
Figure 18B:
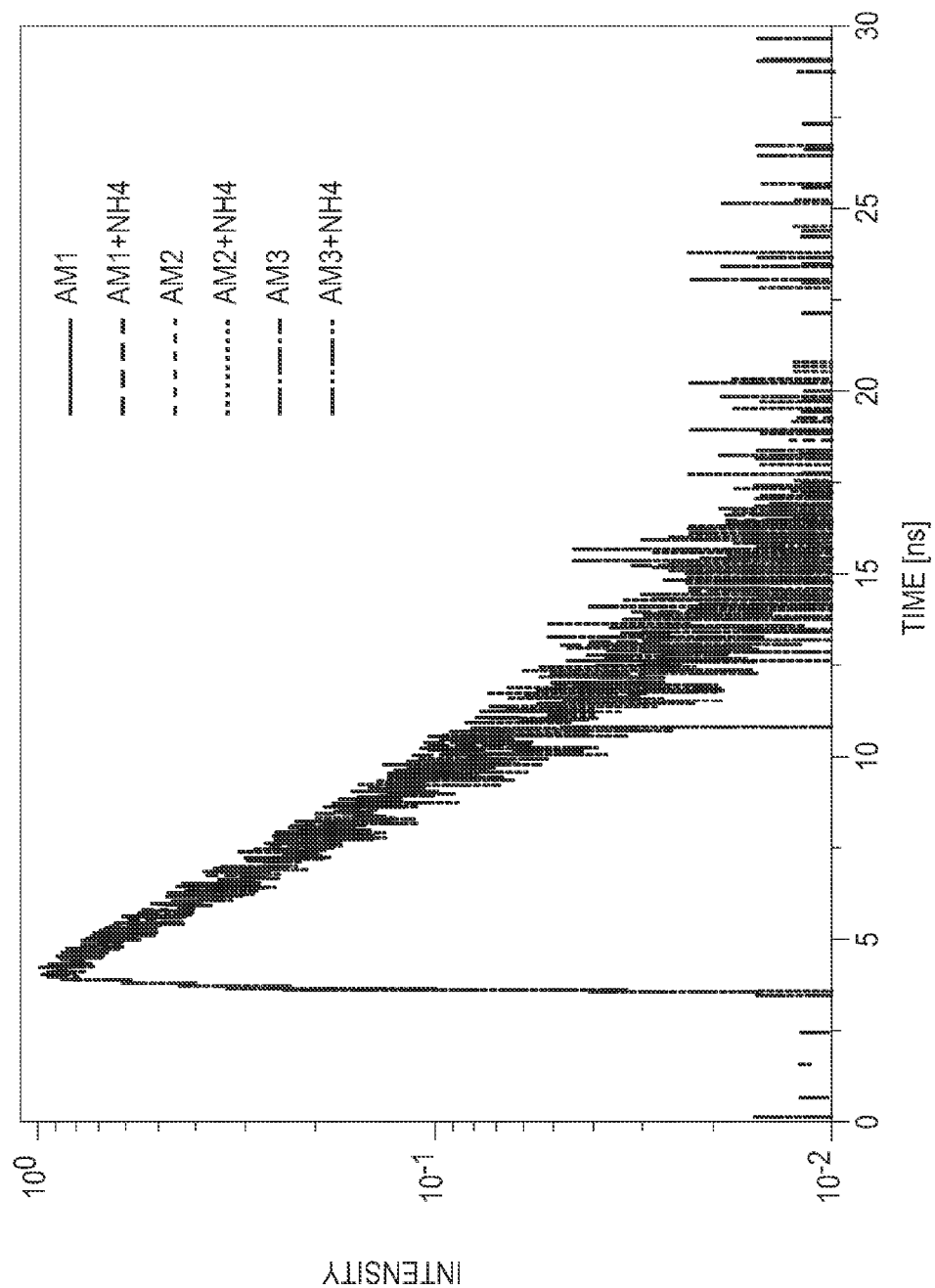

Fluorescence lifetime was also measured in AmTrac variations. Briefly, cells were cultivated with proline as sole source of nitrogen. Before measurements, the cells were washed 3× and resuspended in 50 mM MES, pH 6+5% Glycerol. The total volume in each cuvette was 2.5 mL (2 ml cells of OD=0.5+0.5 ml 5 mM NH$_4$Cl). Measurements were performed for 5 minutes each. After addition of NH$_4$Cl, sufficient time was given, to achieve saturation of the sensor. As control the same concentration of NaCl was used. Lifetime decays were recorded on a FL920 spectrometer (Edinburgh Instruments, UK), for 5 minutes each, using 3.5 mL silica cuvettes (Helima Analytics). Excitation and emission were set to 475 nm and 514 nm, respectively. Graphs were created by the software Origin (OriginLab). FIG. 18a is a plot of fluorescence lifetime decays, plotted with a logarithmic scale, and shows a single exponential decay for all the variants tested with and without addition of saturating ammonium concentrations. While the lifetime was not altered, the FI decrease triggered by ammonium addition was visible. FIG. 18b shows normalized fluorescence lifetime decays of all the variants tested with and without the addition of ammonium. Data were plotted to show that lifetime decays in a similar manner after addition of ammonium.

Using a monoexponential function, the single fluorescence decay times can be calculated according to the formula below. The results are presented in Table IV, which shows that the decay times remain the same for each sensor tested.

$$y = y_0 + A_1 \cdot \exp(-t/\tau)$$

$y_0$=backround (noise)
$A_1$=amplitude (max Int.)
$\tau$=fluorescence decay.

TABLE IV

| Variant | $y_0$ | $A_1$ | $\tau$ [ns] |
|---|---|---|---|
| AmTrac-GS | 3.72 | 1607.22 | 2.5 |
| AmTrac-GS + 1 mM NH$_4$Cl | 3.61 | 825.40 | 2.5 |
| AmTrac-LS | 3.74 | 810.61 | 2.4 |
| AmTrac-LS + 1 mM NH$_4$Cl | 3.68 | 351.62 | 2.4 |
| AmTrac-IS | 3.57 | 664.76 | 2.4 |
| AmTrac-IS + 1 mM NH$_4$Cl | 3.71 | 250.97 | 2.4 |

The measurement of flux through a transporter by reporting state changes, as shown here, is applicable to other transporters or enzymes for monitoring in vivo fluxes, e.g., in the context of neurotransmitter transport, for transporters that have structural inverted repeats as the AMT protein does.

Figure 19A:
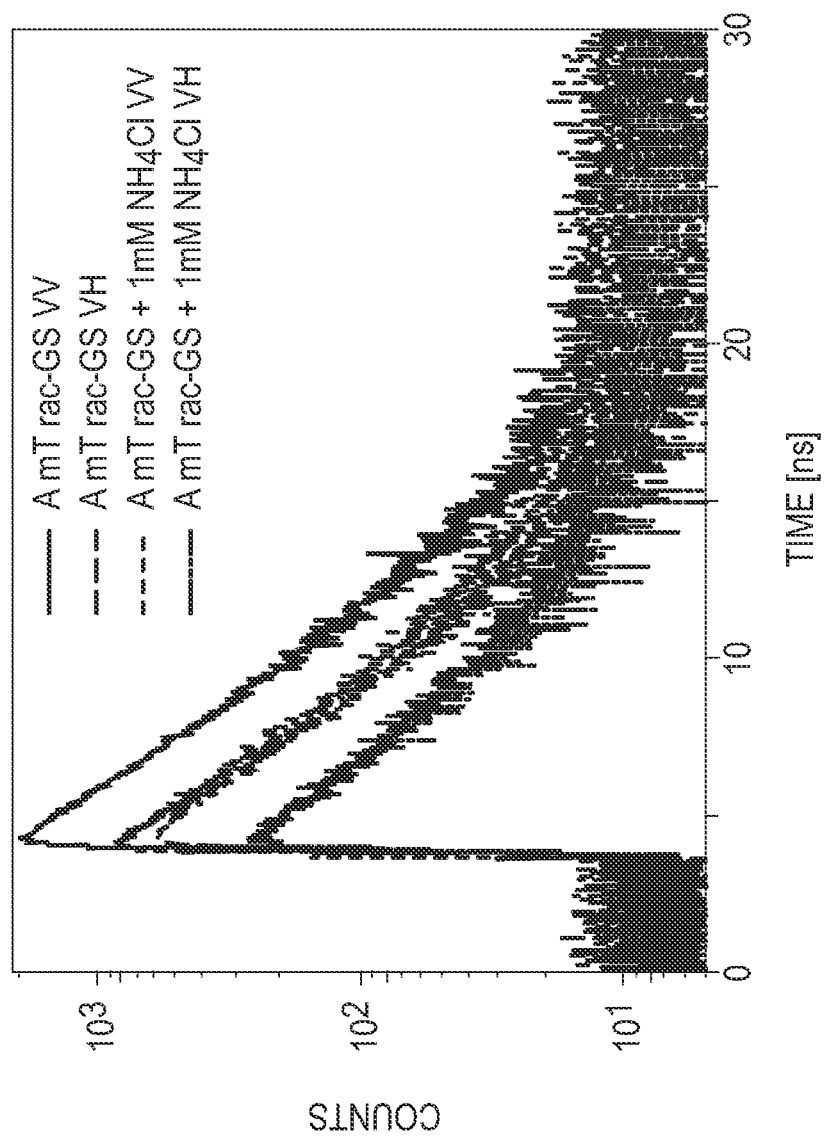
FIG. 19 depicts the time-resolved anisotropy measurements of intact yeast cells expressing AmTrac-GS to elucidate the relevance of homo-FRET in the sensor mechanism.
Figure 19B:
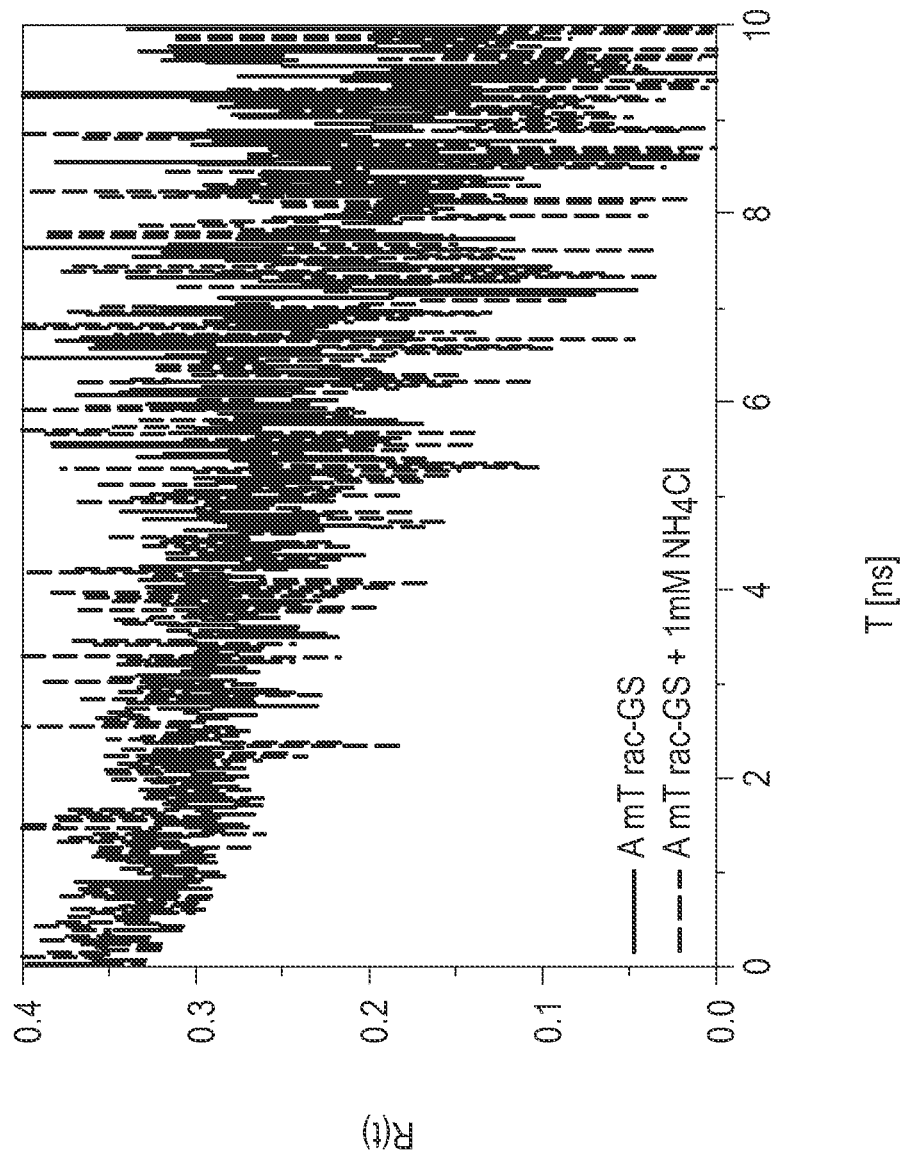

Time-resolved anisotropy was also measured in intact yeast cells expressing AmTrac-GS to elucidate the relevance of homo-FRET in the sensor mechanism. VV—(vertical excitation and vertical emission) and VH—(vertical excitation and horizontal emission) polarized decay curves with and without the addition of 1 mM NH$_4$Cl were recorded for 15 minutes each on a FL920 spectrometer (Edinburgh Instruments, UK) using 3.5 mL silica cuvettes (Hellma Analytics). Excitation and emission were set to 475 nm and 514 nm, respectively. Graphs were created by the software Origin (OriginLab). FIG. 19a shows the single exponential decay of AmTrac-GS's lifetime which is not altered after the addition of ammonium. The lack of an additional fast depolarization in the VV- and VH-decays leads to the conclusion, that homo-FRET cannot be detected for the system tested. FIG. 19b shows a similar decay in anisotropy decay curves for AmTrac-GS, with and without addition of ammonium, which indicates a similar rotation time of the fluorophore mcpGFP in AmTrac-GS.

What is claimed is:

1. An engineered transporter protein comprising at least one fluorescent reporter covalently bound to the transporter protein, with the transporter protein comprising a structural inverted repeat motif comprising a first and second subunit that are structural inverted repeats of one another and that are joined to one another by a polypeptide loop, wherein the at least one fluorescent reporter is covalently bound to the polypeptide loop.

2. The engineered transporter protein of claim 1, wherein the fluorescent reporter is a fluorescent protein.

3. The engineered transporter protein of claim 2, wherein the fluorescent protein is selected from the group consisting of green fluorescent protein (GFP) and circular permutated green fluorescent protein (cpGFP).

4. The engineered transporter protein of claim 1, further comprising at least one linker peptide that links the fluorescent reporter to the polypeptide loop.

5. The engineered transporter protein of claim 4, comprising two linker peptides that link the fluorescent reporter to the polypeptide loop.

6. The engineered transporter protein of claim 5, wherein each of the first and second subunits of the structural inverted repeats independently comprises three, four, five, six or seven alpha helices.

7. The engineered transporter protein of claim 6, wherein the engineered transporter protein is a member of the AMT/MEP/RH superfamily of transporters.

8. A nucleic acid encoding the engineered transporter protein of claim 1.

9. A vector comprising the nucleic acid of claim 8.

10. A host cell comprising the vector of claim 9.

11. The host cell of claim 10 selected from the group consisting of a plant cell and an animal cell.

12. A method of monitoring transport of a target analyte across a cell membrane, the method comprising inserting the engineered transporter protein of claim 1 into the cell membrane to control influx and efflux of the target analyte across the membrane and detecting changes in fluorescence of the fluorescent reporter, wherein a change in fluorescence indicates transport of the target analyte across the membrane through the engineered transporter protein.

13. The method of claim 12, wherein the cell is a eukaryotic cell.

14. The method of claim 12, wherein the target analyte is an amino acid.

* * * * *

SEQUENCE LISTING

<160> NUMBER OF SEQ ID NOS: 32

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
aacgtctata tcatggcc                                                 18

<210> SEQ ID NO 2
<211> LENGTH: 34
<212> TYPE: DNA
<213> ORGANISM: Artificial Sequence
<220> FEATURE:
<223> OTHER INFORMATION: Primer

<400> SEQUENCE: 2
tttttaccgg taccaccctt gtacagctcg tcca                               34

<210> SEQ ID NO 3
<211> LENGTH: 33
<212> TYPE: DNA
<213> ORGANISM: Artificial Sequence

```
<220> FEATURE:
<223> OTHER INFORMATION: Primer

<400> SEQUENCE: 3
tttttaccgg tggatctatg gtgagcaagg gcg                              33

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
agttgtactc cagcttgtgc                                             20

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5 tttttttctag aaacgtctat atcatggcc                                  29

<210> SEQ ID NO 6
<211> LENGTH: 31
<212> TYPE: DNA
<213> ORGANISM: Artificial Sequence
<220> FEATURE:
<223> OTHER INFORMATION: Primer

<400> SEQUENCE: 6 tttttttctag aagttgtact ccagcttgtg c                               31

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7 tttttttctag aatggtgagc aagggcgagg                                 30

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8 tttttttctag acttgtacag ctcgtccatg                                 30

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9 tttttttctag aaagggcgag gagctgttca                                 30
```

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10 tttttctag acttgtacag ctcgtccatg                                30

<210> SEQ ID NO 11
<211> LENGTH: 48
<212> TYPE: DNA
<213> ORGANISM: Artificial Sequence
<220> FEATURE:
<223> OTHER INFORMATION: Primer

<400> SEQUENCE: 11
ggtcctcgtc gtggtcggtt cgagaaatct cataacgtct atatcaag            48

<210> SEQ ID NO 12
<211> LENGTH: 54
<212> TYPE: DNA
<213> ORGANISM: Artificial Sequence
<220> FEATURE:
<223> OTHER INFORMATION: Primer

<400> SEQUENCE: 12
ggtcctcgtc gtggtcggtt cgagaaaggt ggttctcata acgtctatat caag      54

<210> SEQ ID NO 13
<211> LENGTH: 60
<212> TYPE: DNA
<213> ORGANISM: Artificial Sequence
<220> FEATURE:
<223> OTHER INFORMATION: Primer

<400> SEQUENCE: 13
ggtcctcgtc gtggtcggtt cgagaaaggt ggtggtggtt ctcataacgt ctatatcaag   60

<210> SEQ ID NO 14
<211> LENGTH: 48
<212> TYPE: DNA
<213> ORGANISM: Artificial Sequence
<220> FEATURE:
<223> OTHER INFORMATION: Primer

<400> SEQUENCE: 14
ggtcctcgtc gtggtcggtt cgagaaactc gagaacgtct atatcaag            48

<210> SEQ ID NO 15
<211> LENGTH: 54
<212> TYPE: DNA
<213> ORGANISM: Artificial Sequence
<220> FEATURE:
<223> OTHER INFORMATION: Primer

<400> SEQUENCE: 15
ggtcctcgtc gtggtcggtt cgagaaaggt ggtctcgaga acgtctatat caag      54

<210> SEQ ID NO 16
<211> LENGTH: 60
<212> TYPE: DNA
<213> ORGANISM: Artificial Sequence
<220> FEATURE:
<223> OTHER INFORMATION: Primer

<400> SEQUENCE: 16
ggtcctcgtc gtggtcggtt cgagaaaggt ggtggtggtc tcgagaacgt ctatatcaag    60

<210> SEQ ID NO 17
<211> LENGTH: 46
<212> TYPE: DNA
<213> ORGANISM: Artificial Sequence
<220> FEATURE:
<223> OTHER INFORMATION: Primer

<400> SEQUENCE: 17
gtggccgcgc agagcaatag cgcgaccacc gttgtactcc agcttg    46

<210> SEQ ID NO 18
<211> LENGTH: 52
<212> TYPE: DNA
<213> ORGANISM: Artificial Sequence
<220> FEATURE:
<223> OTHER INFORMATION: Primer

<400> SEQUENCE: 18
gtggccgcgc agagcaatag cgcgaccacc tcctccgttg tactccagct tg    52

<210> SEQ ID NO 19
<211> LENGTH: 52
<212> TYPE: DNA
<213> ORGANISM: Artificial Sequence
<220> FEATURE:
<223> OTHER INFORMATION: Primer

<400> SEQUENCE: 19
gtggccgcgc agagcaatag cgcgaccacc attaaagttg tactccagct tg    52

<210> SEQ ID NO 20
<211> LENGTH: 52
<212> TYPE: DNA
<213> ORGANISM: Artificial Sequence
<220> FEATURE:
<223> OTHER INFORMATION: Primer

<400> SEQUENCE: 20
gtggccgcgc agagcaatag cgcgaccacc tcttgtgttg tactccagct tg    52

<210> SEQ ID NO 21
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (28)..(33)
<223> OTHER INFORMATION: n is a, c, g, or t

<400> SEQUENCE: 21
ggtcctcgtc gtggtcggtt cgagaaannn nnnaacgtct atatcaag    48

<210> SEQ ID NO 22
<211> LENGTH: 52
<212> TYPE: DNA
<213> ORGANISM: Artificial Sequence
<220> FEATURE:
<223> OTHER INFORMATION: Primer

<400> SEQUENCE: 22

```
gtggccgcgc agagcaatag cgcgaccacc attaaagttg tactccagct tg            52
```

<210> SEQ ID NO 23
<211> LENGTH: 22
<212> TYPE: PRT
<213> ORGANISM: Artificial Sequence
<220> FEATURE:
<223> OTHER INFORMATION: ER targeting peptide

<400> SEQUENCE: 23

```
His Lys Thr Met Leu Pro Leu Pro Leu Ile Pro Ser Leu Leu Leu Ser
1               5                   10                  15

Leu Ser Ser Ala Glu Phe
            20
```

<210> SEQ ID NO 24
<211> LENGTH: 15
<212> TYPE: PRT
<213> ORGANISM: Nicotiana tabacum

<400> SEQUENCE: 24

```
Gln Pro Ser Leu Lys Arg Met Lys Ile Gln Pro Ser Ser Gln Pro
1               5                   10                  15
```

<210> SEQ ID NO 25
<211> LENGTH: 7
<212> TYPE: PRT
<213> ORGANISM: Artificial Sequence
<220> FEATURE:
<223> OTHER INFORMATION: N-terminal myristate attachment sequence

<400> SEQUENCE: 25

```
Met Gly Ser Ser Lys Ser Lys
1               5
```

<210> SEQ ID NO 26
<211> LENGTH: 7
<212> TYPE: PRT
<213> ORGANISM: Artificial Sequence
<220> FEATURE:
<223> OTHER INFORMATION: SV-40 large T-antigen nuclear localisation
      sequence

<400> SEQUENCE: 26

```
Pro Lys Lys Lys Arg Lys Val
1               5
```

<210> SEQ ID NO 27
<211> LENGTH: 28
<212> TYPE: PRT
<213> ORGANISM: Artificial Sequence
<220> FEATURE:
<223> OTHER INFORMATION: N-terminal targeting sequence

<400> SEQUENCE: 27

```
Met Ser Val Leu Thr Pro Leu Leu Leu Arg Gly Leu Thr Gly Ser Ala
1               5                   10                  15

Arg Arg Leu Pro Val Pro Arg Ala Lys Ile Ser Leu
            20                  25
```

<210> SEQ ID NO 28
<211> LENGTH: 743
<212> TYPE: PRT
<213> ORGANISM: Artificial Sequence
<220> FEATURE:
<223> OTHER INFORMATION: Fusion protein

<400> SEQUENCE: 28

Met Ser Gly Ala Ile Thr Cys Ser Ala Ala Asp Leu Ala Thr Leu Leu
1               5                   10                  15

Gly Pro Asn Ala Thr Ala Ala Asp Tyr Ile Cys Gly Gln Leu Gly
            20                  25                  30

Thr Val Asn Asn Lys Phe Thr Asp Ala Ala Phe Ala Ile Asp Asn Thr
            35                  40                  45

Tyr Leu Leu Phe Ser Ala Tyr Leu Val Phe Ala Met Gln Leu Gly Phe
    50                  55                  60

Ala Met Leu Cys Ala Gly Ser Val Arg Ala Lys Asn Thr Met Asn Ile
65                  70                  75                  80

Met Leu Thr Asn Val Leu Asp Ala Ala Gly Gly Leu Phe Tyr Tyr
                85                  90                  95

Leu Phe Gly Tyr Ala Phe Ala Phe Gly Ser Ser Glu Gly Phe Ile
            100                 105                 110

Gly Arg His Asn Phe Ala Leu Arg Asp Phe Pro Thr Pro Thr Ala Asp
        115                 120                 125

Tyr Ser Phe Phe Leu Tyr Gln Trp Ala Phe Ala Ile Ala Ala Ala Gly
    130                 135                 140

Ile Thr Ser Gly Ser Ile Ala Glu Arg Thr Gln Phe Val Ala Tyr Leu
145                 150                 155                 160

Ile Tyr Ser Ser Phe Leu Thr Gly Phe Val Tyr Pro Val Val Ser His
                165                 170                 175

Trp Phe Trp Ser Pro Asp Gly Trp Ala Ser Pro Phe Arg Ser Ala Asp
            180                 185                 190

Asp Arg Leu Phe Ser Thr Gly Ala Ile Asp Phe Ala Gly Ser Gly Val
        195                 200                 205

Val His Met Val Gly Gly Ile Ala Gly Leu Trp Gly Ala Leu Ile Glu
    210                 215                 220

Gly Pro Arg Arg Gly Arg Phe Glu Lys Leu Glu Asn Val Tyr Ile Lys
225                 230                 235                 240

Ala Asp Lys Gln Lys Asn Gly Ile Lys Ala Asn Phe Lys Ile Arg His
                245                 250                 255

Asn Ile Glu Asp Gly Gly Val Gln Leu Ala Tyr His Tyr Gln Gln Asn
            260                 265                 270

Thr Pro Ile Gly Asp Gly Pro Val Leu Leu Pro Asp Asn His Tyr Leu
        275                 280                 285

Ser Val Gln Ser Lys Leu Ser Lys Asp Pro Asn Glu Lys Arg Asp His
    290                 295                 300

Met Val Leu Leu Glu Phe Val Thr Ala Ala Gly Ile Thr Leu Gly Met
305                 310                 315                 320

Asp Glu Leu Tyr Lys Gly Gly Thr Gly Gly Ser Met Val Ser Lys Gly
                325                 330                 335

Glu Glu Leu Phe Thr Gly Val Val Pro Ile Leu Val Glu Leu Asp Gly
            340                 345                 350

Asp Val Asn Gly His Lys Phe Ser Val Ser Gly Glu Gly Glu Gly Asp
        355                 360                 365

Ala Thr Tyr Gly Lys Leu Thr Leu Lys Phe Ile Cys Thr Thr Gly Lys
    370                 375                 380

Leu Pro Val Pro Trp Pro Thr Leu Val Thr Thr Leu Thr Tyr Gly Val
385                 390                 395                 400

Gln Cys Phe Ser Arg Tyr Pro Asp His Met Lys Gln His Asp Phe Phe

```
                405                 410                 415
Lys Ser Ala Met Pro Glu Gly Tyr Ile Gln Glu Arg Thr Ile Phe Phe
                420                 425                 430

Lys Asp Asp Gly Asn Tyr Lys Thr Arg Ala Glu Val Lys Phe Glu Gly
                435                 440                 445

Asp Thr Leu Val Asn Arg Ile Glu Leu Lys Gly Ile Asp Phe Lys Glu
            450                 455                 460

Asp Gly Asn Ile Leu Gly His Lys Leu Glu Tyr Asn Phe Asn Gly Gly
465                 470                 475                 480

Arg Ala Ile Ala Leu Arg Gly His Ser Ala Ser Leu Val Leu Gly
                485                 490                 495

Thr Phe Leu Leu Trp Phe Gly Trp Tyr Gly Phe Asn Pro Gly Ser Phe
                500                 505                 510

Thr Lys Ile Leu Val Pro Tyr Asn Ser Gly Ser Asn Tyr Gly Gln Trp
                515                 520                 525

Ser Gly Ile Gly Arg Thr Ala Val Asn Thr Thr Leu Ser Gly Cys Thr
                530                 535                 540

Ala Ala Leu Thr Thr Leu Phe Gly Lys Arg Leu Leu Ser Gly His Trp
545                 550                 555                 560

Asn Val Thr Asp Val Cys Asn Gly Leu Leu Gly Gly Phe Ala Ala Ile
                565                 570                 575

Thr Ala Gly Cys Ser Val Val Glu Pro Trp Ala Ala Ile Val Cys Gly
                580                 585                 590

Phe Met Ala Ser Val Val Leu Ile Gly Cys Asn Lys Leu Ala Glu Leu
                595                 600                 605

Val Gln Tyr Asp Asp Pro Leu Glu Ala Ala Gln Leu His Gly Gly Cys
                610                 615                 620

Gly Ala Trp Gly Leu Ile Phe Val Gly Leu Phe Ala Lys Glu Lys Tyr
625                 630                 635                 640

Leu Asn Glu Val Tyr Gly Ala Thr Pro Gly Arg Pro Tyr Gly Leu Phe
                645                 650                 655

Met Gly Gly Gly Lys Leu Leu Gly Ala Gln Leu Val Gln Ile Leu
                660                 665                 670

Val Ile Val Gly Trp Val Ser Ala Thr Met Gly Thr Leu Phe Ile
            675                 680                 685

Leu Lys Arg Leu Asn Leu Leu Arg Ile Ser Glu Gln His Glu Met Gln
                690                 695                 700

Gly Met Asp Met Thr Arg His Gly Gly Phe Ala Tyr Ile Tyr His Asp
705                 710                 715                 720

Asn Asp Asp Glu Ser His Arg Val Asp Pro Gly Ser Pro Phe Pro Arg
                725                 730                 735

Ser Ala Thr Pro Pro Arg Val
                740

<210> SEQ ID NO 29
<211> LENGTH: 2229
<212> TYPE: DNA
<213> ORGANISM: Artificial Sequence
<220> FEATURE:
<223> OTHER INFORMATION: Nucleotide sequence of fusion protein

<400> SEQUENCE: 29
atgtcaggag caataacatg ctctgcggcc gatctcgcca ccctacttgg ccccaacgcc      60
acggcggcgg ccgactacat tgcggccaa ttaggcaccg ttaacaacaa gttcaccgat    120
```

```
gcagccttcg ccatagacaa cacctacctc ctcttctctg cctaccttgt cttcgccatg      180
cagctcggct tcgctatgct ttgtgctggt tctgttagag ccaagaatac gatgaacatc      240
atgcttacca atgtccttga cgctgcagcc ggaggactct tctactatct ctttggttac      300
gcctttgcct ttggaggatc ctccgaaggg ttcattggaa gacacaactt tgctcttaga      360
gactttccga ctcccacagc tgattactct ttcttcctct accaatgggc gttcgcaatc      420
gcggccgctg gaatcacaag tggttcgatc gcagagagga ctcagttcgt ggcttacttg      480
atatactctt ctttcttaac cggatttgtt tacccggttg tctctcactg gttttggtcc      540
ccggatggat gggccagtcc ctttcgttca gcggatgatc gtttgtttag caccggagcc      600
attgactttg ctggctccgg tgttgttcac atggttggtg gcatagcagg tttatggggt      660
gctcttattg aaggtcctcg tcgtggtcgg ttcgagaaac tcgagaacgt ctatatcaag      720
gccgacaagc agaagaacgg catcaaggcg aacttcaaga tccgccacaa catcgaggac      780
ggcggcgtgc agctcgccta ccactaccag cagaacaccc ccatcggcga cggccccgtg      840
ctgctgcccg acaaccacta cctgagcgtc cagtccaagc tgagcaaaga ccccaacgag      900
aagcgcgatc acatggtcct gctggagttc gtgaccgccg ccgggatcac tctcggcatg      960
gacgagctgt acaagggtgg taccggtgga tctatggtga gcaagggcga ggagctgttc     1020
accggggtgg tgcccatcct ggtcgagctg gacggcgacg taaacggcca agttcagc       1080 gtgtccggcg agggcgaggg cgatgccacc tacggcaagc tgaccctgaa gttcatctgc     1140
accaccggca agctgcccgt gccctggccc accctcgtga ccaccctgac ctacggcgtg     1200
cagtgcttca gccgctaccc cgaccacatg aagcagcacg acttcttcaa gtccgccatg     1260
cccgaaggct acatccagga gcgcaccatc ttcttcaagg acgacggcaa ctacaagacc     1320
cgcgccgagg tgaagttcga gggcgacacc ctggtgaacc gcatcgagct gaagggcatc     1380
gacttcaagg aggacggcaa catcctgggg cacaagctgg agtacaactt taatggtggt     1440
cgcgctattg ctctgcgcgg ccactctgcc tcgctagtag tcttaggaac cttcctccta     1500
tggtttggat ggtatggttt caaccccggt tccttcacta agatactcgt tccgtataat     1560
tctggttcca actacggcca atggagcgga atcggccgta cagcggttaa caccacactc     1620
tcaggatgca cagcagctct aaccacactc tttggtaaac gtctcctatc aggccactgg     1680
aacgtaacgg acgtttgcaa cgggttactc ggtgggtttg cggccataac cgcaggttgc     1740
tccgtcgtag agccatgggc agcgattgtg tgcggcttca tggcttctgt cgtccttatc     1800
ggatgcaaca agctcgcgga gcttgtacaa tatgatgatc cactcgaggc agcccaacta     1860
catggagggt gtggcgcgtg ggggttgata ttcgtaggat tgtttgccaa agagaagtat     1920
ctaaacgagg tttatggcgc caccccggga aggccatatg gactatttat gggcggagga     1980
gggaagctgt tgggagcaca attggttcaa atacttgtga ttgtaggatg ggttagtgcc     2040
acaatgggaa cactcttctt catcctcaaa aggctcaatc tgcttaggat ctcggagcag     2100
catgaaatgc aagggatgga tatgacacgt cacggtggct ttgcttatat ctaccatgat     2160
aatgatgatg agtctcatag agtggatcct ggatctcctt tccctcgatc agctactcct     2220
cctcgcgtt                                                             2229
```

<210> SEQ ID NO 30
<211> LENGTH: 2240
<212> TYPE: DNA
<213> ORGANISM: Artificial Sequence
<220> FEATURE:
<223> OTHER INFORMATION: Nucleotide sequence of fusion protein

<400> SEQUENCE: 30

```
atgtcaggag caataacatg ctctgcggcc gatctcgcca ccctacttgg ccccaacgcc      60
acggcggcgg ccgactacat ttgcggccaa ttaggcaccg ttaacaacaa gttcaccgat     120
gcagccttcg ccatagacaa cacctacctc ctcttctctg cctaccttgt cttcgccatg     180
cagctcggct tcgctatgct ttgtgctggt tctgttagag ccaagaatac gatgaacatc     240
atgcttacca atgtccttga cgctgcagcc ggaggactct tctactatct ctttggttac     300
gcctttgcct ttggaggatc tccgaaggg ttcattggaa gacacaactt tgctcttaga      360
gactttccga ctcccacagc tgattactct ttcttcctct accaatgggc gttcgcaatc     420
gcggccgctg aatcacaag tggttcgatc gcagagagga ctcagttcgt ggcttacttg      480
atatactctt ctttcttaac cggatttgtt tacccggttg tctctcactg gttttggtcc     540
ccggatggat gggccagtcc ctttcgttca gcggatgatc gtttgtttag caccggagcc     600
attgactttg ctggctccgg tgttgttcac atggttggtg gcatagcagg tttatggggt     660
gctcttattg aaggtcctcg tcgtggtcgg ttcgagaaag gtggtctcga gaacgtaacg     720
tctatatcaa ggccgacaag cagaagaacg gcatcaaggc gaacttcaag atccgccaca     780
acatcgagga cggcggcgtg cagctcgcct accactacca gcagaacacc cccatcggcg     840
acggccccgt gctgctgccc gacaaccact acctgagcgt ccagtccaag ctgagcaaag     900
accccaacga gaagcgcgat cacatggtcc tgctggagtt cgtgaccgcc gccgggatca     960
ctctcggcat ggacgagctg tacaagggtg gtaccggtgg atctatggtg agcaagggcg    1020
aggagctgtt caccggggtg gtgcccatcc tggtcgagct ggacggcgac gtaaacggcc    1080
acaagttcag cgtgtccggc gagggcgagg gcgatgccac ctacggcaag ctgaccctga    1140
agttcatctg caccaccggc aagctgcccg tgccctggcc caccctcgtg accaccctga    1200
cctacggcgt gcagtgcttc agccgctacc ccgaccacat gaagcagcac gacttcttca    1260
agtccgccat gcccgaaggc tacatccagg agcgcaccat cttcttcaag gacgacggca    1320
actacaagac ccgcgccgag gtgaagttcg agggcgacac cctggtgaac cgcatcgagc    1380
tgaagggcat cgacttcaag gaggacggca acatcctggg gcacaagctg gagtacaact    1440
ttaatggtgg tcgcgctatt gctctgcgcg gccactctgc ctcgctagta gtcttaggaa    1500
ccttcctcct atggtttgga tggtatggtt caaccccgg ttccttcact aagatactcg      1560
ttccgtataa ttctggttcc aactacggcc aatggagcgg aatcggccgt acagcggtta    1620
acaccacact ctcaggatgc acagcagctc taaccacact ctttggtaaa cgtctcctat    1680
caggccactg gaacgtaacg gacgtttgca acgggttact cggtgggttt gcggccataa    1740
ccgcaggttc ctccgtcgta gagccatggg cagcgattgt gtgcggcttc atggcttctg    1800
tcgtccttat cggatgcaac aagctcgcgg agcttgtaca atatgatgat ccactcgagg    1860
cagcccaact acatggaggg tgtggcgcgt ggggttgat attcgtagga ttgtttgcca     1920
aagagaagta tctaaacgag gtttatggcg ccaccccggg aaggccatat ggactattta    1980
tgggcggagg agggaagctg ttgggagcac aattggttca aatacttgtg attgtaggat    2040
gggttagtgc cacaatggga acactcttct tcatcctcaa aaggctcaat ctgcttagga    2100
tctcggagca gcatgaaatg caagggatgg atatgacacg tcacggtggc tttgcttata    2160
tctaccatga taatgatgat gagtctcata gagtggatcc tggatctcct ttccctcgat    2220
cagctactcc tcctcgcgtt                                                 2240
```

```
<210> SEQ ID NO 31
<211> LENGTH: 241
<212> TYPE: PRT
<213> ORGANISM: Artificial Sequence
<220> FEATURE:
<223> OTHER INFORMATION: cpGFP portion

<400> SEQUENCE: 31

Asn Val Tyr Ile Lys Ala Asp Lys Gln Lys Asn Gly Ile Lys Ala Asn
1               5                   10                  15

Phe Lys Ile Arg His Asn Ile Glu Asp Gly Gly Val Gln Leu Ala Tyr
            20                  25                  30

His Tyr Gln Gln Asn Thr Pro Ile Gly Asp Gly Pro Val Leu Leu Pro
        35                  40                  45

Asp Asn His Tyr Leu Ser Val Gln Ser Lys Leu Ser Lys Asp Pro Asn
    50                  55                  60

Glu Lys Arg Asp His Met Val Leu Leu Glu Phe Val Thr Ala Ala Gly
65                  70                  75                  80

Ile Thr Leu Gly Met Asp Glu Leu Tyr Lys Gly Gly Thr Gly Gly Ser
                85                  90                  95

Met Val Ser Lys Gly Glu Glu Leu Phe Thr Gly Val Val Pro Ile Leu
            100                 105                 110

Val Glu Leu Asp Gly Asp Val Asn Gly His Lys Phe Ser Val Ser Gly
        115                 120                 125

Glu Gly Glu Gly Asp Ala Thr Tyr Gly Lys Leu Thr Leu Lys Phe Ile
130                 135                 140

Cys Thr Thr Gly Lys Leu Pro Val Pro Trp Pro Thr Leu Val Thr Thr
145                 150                 155                 160

Leu Thr Tyr Gly Val Gln Cys Phe Ser Arg Tyr Pro Asp His Met Lys
                165                 170                 175

Gln His Asp Phe Phe Lys Ser Ala Met Pro Glu Gly Tyr Ile Gln Glu
            180                 185                 190

Arg Thr Ile Phe Phe Lys Asp Asp Gly Asn Tyr Lys Thr Arg Ala Glu
        195                 200                 205

Val Lys Phe Glu Gly Asp Thr Leu Val Asn Arg Ile Glu Leu Lys Gly
    210                 215                 220

Ile Asp Phe Lys Glu Asp Gly Asn Ile Leu Gly His Lys Leu Glu Tyr
225                 230                 235                 240

Asn

<210> SEQ ID NO 32
<211> LENGTH: 6
<212> TYPE: PRT
<213> ORGANISM: Artificial Sequence
<220> FEATURE:
<223> OTHER INFORMATION: Linker

<400> SEQUENCE: 32

Gly Gly Thr Gly Gly Ser
1               5
```